United States Patent
Long et al.

(10) Patent No.: US 10,946,036 B2
(45) Date of Patent: Mar. 16, 2021

(54) USE OF MYOSTATIN INHIBITORS AND COMBINATION THERAPIES

(71) Applicant: Scholar Rock, Inc., Cambridge, MA (US)

(72) Inventors: Kimberly Long, Boston, MA (US); Adriana Donovan, West Roxbury, MA (US); Yung Chyung, Lexington, MA (US); Michelle Straub, Yarmouth, ME (US)

(73) Assignee: Scholar Rock, Inc., Cambridge, MA (US)

( * ) Notice: Subject to any disclaimer, the term of this patent is extended or adjusted under 35 U.S.C. 154(b) by 15 days.

(21) Appl. No.: 16/308,007

(22) PCT Filed: Jun. 13, 2017

(86) PCT No.: PCT/US2017/037332
§ 371 (c)(1),
(2) Date: Dec. 7, 2018

(87) PCT Pub. No.: WO2017/218592
PCT Pub. Date: Dec. 21, 2017

(65) Prior Publication Data
US 2019/0255093 A1  Aug. 22, 2019

Related U.S. Application Data

(60) Provisional application No. 62/512,254, filed on May 30, 2017, provisional application No. 62/511,702, filed on May 26, 2017, provisional application No. 62/486,934, filed on Apr. 18, 2017, provisional application No. 62/470,157, filed on Mar. 10, 2017, provisional application No. 62/349,596, filed on Jun. 13, 2016.

(51) Int. Cl.
| | |
|---|---|
| *A61K 31/7105* | (2006.01) |
| *C12N 15/113* | (2010.01) |
| *A61P 21/00* | (2006.01) |
| *A61K 9/00* | (2006.01) |
| *C07K 16/22* | (2006.01) |
| *A61K 31/7125* | (2006.01) |
| *A61K 31/501* | (2006.01) |
| *A61K 39/395* | (2006.01) |
| *A61K 31/575* | (2006.01) |
| *A61K 45/06* | (2006.01) |
| *A61K 39/00* | (2006.01) |

(52) U.S. Cl.
CPC ........ *A61K 31/7105* (2013.01); *A61K 9/0019* (2013.01); *A61K 31/501* (2013.01); *A61K 31/575* (2013.01); *A61K 31/7125* (2013.01); *A61K 39/3955* (2013.01); *A61P 21/00* (2018.01); *C07K 16/22* (2013.01); *C12N 15/113* (2013.01); *A61K 45/06* (2013.01); *A61K 2039/505* (2013.01); *C07K 2317/24* (2013.01); *C07K 2317/33* (2013.01); *C07K 2317/567* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 6,096,506 A | 8/2000 | Lee et al. |
| 6,656,475 B1 | 12/2003 | Lee et al. |
| 6,858,208 B2 | 2/2005 | Lee et al. |
| 7,138,501 B2 | 11/2006 | Ruben et al. |
| 7,566,768 B1 | 7/2009 | Lee et al. |
| 10,287,345 B2 | 5/2019 | Donovan et al. |
| 10,307,480 B2 | 6/2019 | Straub et al. |
| 2003/0167492 A1 | 9/2003 | Lee et al. |
| 2005/0049402 A1 | 3/2005 | Babcook et al. |
| 2005/0143306 A1 | 6/2005 | Junker et al. |
| 2007/0218067 A1 | 9/2007 | Buttner et al. |
| 2008/0119426 A1 | 5/2008 | Dale |
| 2008/0213251 A1 | 9/2008 | Sexton et al. |
| 2009/0148436 A1 | 6/2009 | Lavallie et al. |
| 2010/0080811 A1 | 4/2010 | Davies et al. |
| 2010/0183616 A1 | 7/2010 | Green et al. |
| 2010/0221777 A1 | 9/2010 | Choe et al. |
| 2011/0165175 A1 | 7/2011 | Linhard et al. |
| 2011/0239317 A1 | 9/2011 | Lee et al. |
| 2013/0209498 A1 | 8/2013 | Han et al. |
| 2013/0216548 A1 | 8/2013 | Neijssen et al. |

(Continued)

FOREIGN PATENT DOCUMENTS

| | | |
|---|---|---|
| AU | 2011244851 A1 | 11/2011 |
| EP | 2853898 A1 | 4/2015 |

(Continued)

OTHER PUBLICATIONS

Benatar, M., Lost in translation: Treatment trials in the SOD1 mouse and in human ALS, 2006, Neurobiology of Disease 26;1-13 (Year: 2006).*

(Continued)

*Primary Examiner* — John D Ulm

(74) *Attorney, Agent, or Firm* — Finnegan, Henderson, Farabow, Garrett & Dunner, LLP

(57) ABSTRACT

The present disclosure relates to the treatment of muscle conditions, such as SMA, with the use of an agent that inhibits myostatin signaling. The disclosure includes combination therapies that include a myostatin inhibitor and a neuronal corrector.

22 Claims, 14 Drawing Sheets

Specification includes a Sequence Listing.

(56) References Cited

U.S. PATENT DOCUMENTS

| | | |
|---|---|---|
| 2013/0336982 A1 | 12/2013 | Mader et al. |
| 2014/0017262 A1 | 1/2014 | Sanicola-Nadel |
| 2014/0023638 A1 | 1/2014 | LaVallie et al. |
| 2017/0198032 A1 | 7/2017 | Donovan et al. |
| 2017/0333558 A1 | 11/2017 | Straub et al. |

FOREIGN PATENT DOCUMENTS

| | | | |
|---|---|---|---|
| WO | WO 1996/01845 | A2 | 1/1996 |
| WO | WO 2003/027248 | A2 | 4/2003 |
| WO | WO 2004/009776 | A2 | 1/2004 |
| WO | WO 2004/024890 | A2 | 3/2004 |
| WO | WO 2004/037861 | A2 | 5/2004 |
| WO | WO 2005/066204 | A2 | 7/2005 |
| WO | WO 2005/084699 | A1 | 9/2005 |
| WO | WO 2005/103081 | A2 | 11/2005 |
| WO | WO 2005/115439 | A2 | 12/2005 |
| WO | WO 2006/116269 | A2 | 11/2006 |
| WO | WO 2007/024535 | A2 | 3/2007 |
| WO | WO 2007/047112 | A2 | 4/2007 |
| WO | WO 2007/061995 | A2 | 5/2007 |
| WO | WO 2008/067480 | A2 | 6/2008 |
| WO | WO 2008/119426 | A1 | 10/2008 |
| WO | WO 2009/038760 | A2 | 3/2009 |
| WO | WO 2010/070094 | A1 | 6/2010 |
| WO | WO 2010/125003 | A1 | 11/2010 |
| WO | WO 2010/144452 | A1 | 12/2010 |
| WO | WO 2011/150008 | A1 | 12/2011 |
| WO | WO 2012/024242 | A1 | 2/2012 |
| WO | 2013/072902 | A1 | 5/2013 |
| WO | WO 2013/071056 | A2 | 5/2013 |
| WO | WO 2013/148284 | A1 | 10/2013 |
| WO | WO 2013/165972 | A2 | 11/2013 |
| WO | WO 2013/186719 | A1 | 12/2013 |
| WO | WO 2014/074532 | A2 | 5/2014 |
| WO | WO 2014/182676 | A2 | 11/2014 |
| WO | WO 2015/070158 | A1 | 5/2015 |
| WO | WO 2015/195094 | A1 | 12/2015 |
| WO | 2016/073853 | A1 | 5/2016 |
| WO | WO 2016/073879 | A2 | 5/2016 |
| WO | WO 2016/073906 | A2 | 5/2016 |
| WO | WO 2016/098357 | A1 | 6/2016 |
| WO | WO 2017/049011 | A1 | 3/2017 |
| WO | WO 2017/120523 | A2 | 7/2017 |
| WO | WO 2018/116201 | A1 | 6/2018 |

OTHER PUBLICATIONS

DiBernardo et al., Translating preclinical insights into effective human trials in ALS, 2006, / Biochimica et Biophysica Acta 1762: 1139-1149 (Year: 2006).*
Gogliotti et al., Characterization of a commonly used mouse model of SMA reveals increased seizure susceptibility and heightened fear response in FVB/N mice, 2011, Neurobiol Dis. 43(1):142-151 (Year: 2011).*
Liu et al., The Smn-Independent Beneficial Effects of Trichostatin A on an Intermediate Mouse Model of Spinal Muscular Atrophy, Jul. 2014, PLOS ONE 9 (7) e101225, 9 pages (Year: 2014).*
Burch et al., (2017) "Reduced serum myostatin concentrations associated with genetic muscle disease progression", Journal of Neurology, 264(3):541-553.
Gonzalez et al., (2005) "BMP-1/Tolloid-like Metalloproteases Process Endorepellin, the Angiostatic C-terminal Fragment of Perlecan", Journal of Biological Chemistry, 280(8):7080-7087.
Latres et al., (2015) "Myostatin blockade with a fully human monoclonal antibody induces muscle hypertrophy and reverses muscle atrophy in young and aged mice", Skeletal Muscle, 5:34, 13 pages, DOI 10.1186/s 13396-015-0060-8.
Long et al., (2019) "Specific inhibition of myostatin activation is beneficial in mouse models of SMA therapy", Human Molecular Genetics, 28(7):1076-1089.

Mariot et al., (2017) "Downregulation of myostatin pathway in neuromuscular diseases may explain challenges of anti-myostatin therapeutic approaches", Nature Communications, 8(1):1859.
Whittemore et al., (2003) "Inhibition of myostatin in adult mice increases skeletal muscle mass and strength", Biochem Biophys Res Commun, 300(4):965-971.
Anonymous (2017) "SC 2. Anterolateral Systems—Deficits" [online]. Retrieved from: http://www.neuroanatomy.wisc.edu/sc97/text/p2/deficits.htm; on Jul. 11, 2017 (1 page).
Anonymous (2019) "GDF-11/BMP-11 Mouse anti-Human, Clone: 743833, R&D Systems(TM)" [online]. Retrieved from: http://www.fishersci.co.uk/shop/products/gdf-11bpm-11-mouse-anti-human-clone-743833-r-d-systems/15724724; on Feb. 28, 2019 (4 pages).
Baranello et al., (2020) "Evaluation of body composition as a potential biomarker in spinal muscular atrophy", Muscle & Nerve, 61(4):530-534.
Bräuninger et al., (2003) "Epstein-Barr virus (EBV)-positive lymphoproliferations in post-transplant patients show immunoglobulin V gene mutation patterns suggesting interference of EBV with normal B cell differentiation processes", Eur J Immunol., 33(6):1593-1602.
Breitbart et al., (2013) "Highly specific detection of myostatin prodomain by an immunoradiometric sandwich assay in serum of healthy individuals and patients", PLoS One, 8(11):e80454 (10 pages).
Brown et al., (1996) "Tolerance of single, but not multiple, amino acid replacements in antibody VH CDR 2: a means of minimizing B cell wastage from somatic hypermutation?", J Immunol., 156(9):3285-3291.
Ciciliot et al., (2013) "Muscle type and fiber type specificity in muscle wasting", Int J Biochem Cell Biol., 45(10):2191-2199.
Cohen et al., (2015) "Muscle wasting in disease: molecular mechanisms and promising therapies", Nat Rev Drug Discov., 14(1):58-74.
Egerman et al., (2015) "GDF11 Increases with Age and Inhibits Skeletal Muscle Regeneration", Cell Metabolism, 22(1):164-174.
European Patent Application No. 16828657.3, by Scholar Rock, Inc: Supplementary European Search Report and Opinion, dated Mar. 20, 2019.
Ferrara et al., (2015) "Recombinant renewable polyclonal antibodies", MAbs, 7(1):32-41.
Ge et al., (2005) "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858.
Giangregorio et al., (2006) "Bone Loss and Muscle Atrophy in Spinal Cord Injury: Epidemiology, Fracture Prediction, and Rehabilitation Strategies", J Spinal Cord Med., 29(5):489-500.
Graham et al., (2015) "A Soluble Myostatin Inhibitor Does Not Prevent Sublesional Muscle Atrophy 56 Days After Spinal Cord Injury in Mice", Medicine & Science in Sports & Exercise, Abstract No. 2219:587.
Guo et al., (2009) "Myostatin Inhibition in Muscle, but Not Adipose Tissue, Decreases Fat Mass and Improves Insulin Sensitivity", PLoS One, 4(3):e4937 (11 pages).
Holzbaur et al., (2006) "Myostatin inhibition slows muscle atrophy in rodent models of amyotrophic lateral sclerosis", Neurobiol Dis., 23(3):697-707.
International Application No. PCT/US2016/043712, by Scholar Rock, Inc., International Search Report and Written Opinion, dated Jan. 13, 2017.
International Application No. PCT/US2017/012606, by Scholar Rock, Inc., International Search Report and Written Opinion, dated Jul. 24, 2017.
International Application No. PCT/US2017/012606, by Scholar Rock, Inc., Written Opinion dated Jan. 3, 2018 (18 pages).
International Application No. PCT/US2018/012686, by Scholar Rock, Inc., International Search Report and Written Opinion, dated Apr. 3, 2018.
International Preliminary Report on Patentability for Application No. PCT/US2015/059468, dated May 9, 2017 (12 pages).
International Preliminary Report on Patentability for Application No. PCT/US2016/052014, dated Mar. 29, 2018 (11 pages).

(56) References Cited

OTHER PUBLICATIONS

International Search Report and Written Opinion for Application No. PCT/US2016/052014, dated Jan. 9, 2017 (17 pages).
International Search Report for Application No. PCT/US20151059468, dated Apr. 4, 2016 (6 pages).
International Search Report for Application No. PCT/US2015/059515, dated Mar. 25, 2016 (8 pages).
Jiang et al., (2019) "Genomic analysis of a spinal muscular atrophy (SMA) discordant family identifies a novel mutation in TLL2, an activator of growth differentiation factor 8 (myostatin): a case report", BMC Medical Genetics, 20(1):204.
Kariya et al., (2014) "Requirement of enhanced Survival Motoneuron protein imposed during neuromuscular junction maturation", The Journal of Clinical Investigation, 124(2):785-800.
Latres et al., (2017) "Activin A more prominently regulates muscle mass in primates than does GDF8", Nature Communications, 8:15153.
Loffredo et al., (2013) "Growth differentiation factor 11 is a circulating factor that reverses age-related cardiac hypertrophy", Cell, 153(4):828-839.
McPherron et al., (2010) "Metabolic Functions of Myostatin and GDF11", Immunol Endocr Metab Agents Med Chem., 10(4):217-231.
Morrison et al., (2009) "A soluble activin type IIB receptor improves function in a mouse model of amyotrophic lateral sclerosis", Exp Neurol, 217(2):258-268.
Pandya et al., (2013) "Therapeutic neuroprotective agents for amyotrophic lateral sclerosis", Cell Mol Life Sci., 70(24):4729-4745.
Pirruccello-Straub et al., (2018) "Blocking extracellular activation of myostatin as a strategy for treating muscle wasting", Scientific Reports, 8(1):2292.
Pistilli et al., (2011) "Targeting Activin Type IIB Receptor to Improve Muscle Mass and Function in the mdx Mouse Model of Duchenne Muscular Dystrophy", Am J Pathol., 178(3):1287-1297.
Pubchem Substance No. CID 310264710 (trevogrumab); Create Date Feb. 5, 2016 [online]. Retrieved from: http://pubchem.ncbi.nlm.nih.gov/substance/310264710; on Feb. 5, 2020 (6 pages).
Sgoutas et al., (1992) "Effect of Lyophilization on Determinations of Lipoprotein(a) in Serum", Clin Chem., 38(7):1355-1360.
Singapore Patent Application No. 11201805709R, filed Jan. 6, 2017, by Scholar Rock, Inc.: International Search Report and Written Opinion, dated Oct. 11, 2019 (12 pages).
Smith et al., (2015) "Myostatin Neutralization Results in Preservation of Muscle Mass and Strength in Preclinical Models of Tumor-Induced Muscle Wasting", Mol Cancer Ther., 14(7):1661-1670.
Suragani et al., (2014) "Transforming growth factor-β superfamily ligand trap ACE-536 corrects anemia by promoting late-stage erythropoiesis", Nature Medicine, 20(4):408-414.
Szlama et al., (2013) "Latent myostatin has significant activity and this activity is controlled more efficiently by WFIKKN1 than by WFIKKN2", FEBS Journal, 280(16):3822-3839.
Unknown (2000) American Spinal Injury Association (ASIA) Impairment Scale, Standard Neurological Classification of Spinal Cord Injury (2 pages).
Unknown (2013) "Myostatin Propeptide Human, Chicken Polyclonal Antibody", BioVendor, Research and Diagnostic Products, Data Sheet (2 pages).
Wang (2000) "Lyophilization and development of solid protein pharmaceuticals", International Journal of Pharmaceutics, 203(1-2):1-60.
Wintgens et al., (2012) "Plasma myostatin measured by a competitive Elisa using a highly specific antiserum", Clin Chim Acta., 413(15-16):1288-1294.
Wolfman et al., (2003) "Activation of latent myostatin by the BMP-1/tolloid family of metalloproteinases", Proc Natl Acad Sci U.S.A., 100(26):15842-15846.
D'Ydewalle et al., Spinal Muscular Atrophy Therapeutics: Where do we Stand?, neurothereraprutics, Elsevier Inc, US, vol. 12, No. 2, Jan. 29, 2015, pp. 303-316.
Dalbo et al., Testosterone and trenbolone enanthate increase mature myostatin protein expression despite increasing skeletal muscle hypertrophy and satellite cell number in rodent muscle, Andrologia, vol. 49, No. 3, Jun. 1, 2016, pp. 1-11.
Feng et al., Pharmacologically induced mouse model of adult spinal muscular atrophy to evaluate effectiveness of therapeutics after disease onset, Human Molecular Genetics, vol. 25, Issue 5, Mar. 1, 2016, pp. 964-975.
International Search Report and Written opinion for PCT/US2017/037332 dated Nov. 14, 2017, pp. 1-19.
Latres et al., Myostatin blockade with a fully human monoclonal antibody induces muscle hypertrophy and reverses muscle atrophy in young and aged mice, Skeletal Muscle, Biomed Central Ltd., vol. 5, No. 1, 9, Oct. 2016, p. 34.
Mosler et al., The anabolic steroid methandienone targets the hypothalamic-pituitary-testicular axis and myostatin signaling in a rat training model, Arch Toxicolvol. 86, No. 15 Aug. 2011, pp. 109-119.
Smith et al., Myostatin inhibitors as therapies for muscle wasting associated with cancer and other disorders., Current Dpinion in Supportive and Palliative Care, vol. 7 No. 4., Nov. 1, 201, pp. 352-360.
Summer et al., Inhibition of myostatin does not ameliorate disease features of severe spinal muscular atrophy mice, Human Molecular Genetics, 28, May 2009, vol. 18, No. 17 3145-3152.
Zhao et al., Pharmacokinetics, pharmacodynamics, and efficacy of a small-molecule SMN2 splicing modifier in mouse models of spinal muscular atrophy, Human Molecular Genetics, 29, Feb. 2016, vol. 25, No. 10 pp. 1885-1899.
Anderson et al., (2008) "Identification of a novel pool of extracellular pro myostatin in skeletal muscle", The Journal of Biological Chemistry, 283(11):7027-7035.
Japanese Patent Application No. 2019-517209, filed Jun. 13, 2017, by Scholar Rock, Inc., Decision to Grant a Patent, dated Dec. 8, 2020 (7 pages).
Australian Application No. 202010134, filed Jul. 27, 2020, for Scholar Rock, Inc.: Examination Report No. 1, dated Oct. 15, 2020 (15 pages).
Wagner (2020) "The elusive promise of myostatin inhibition for muscular dystrophy", Current Opinion in Neurology, 33(5):621-628.

\* cited by examiner

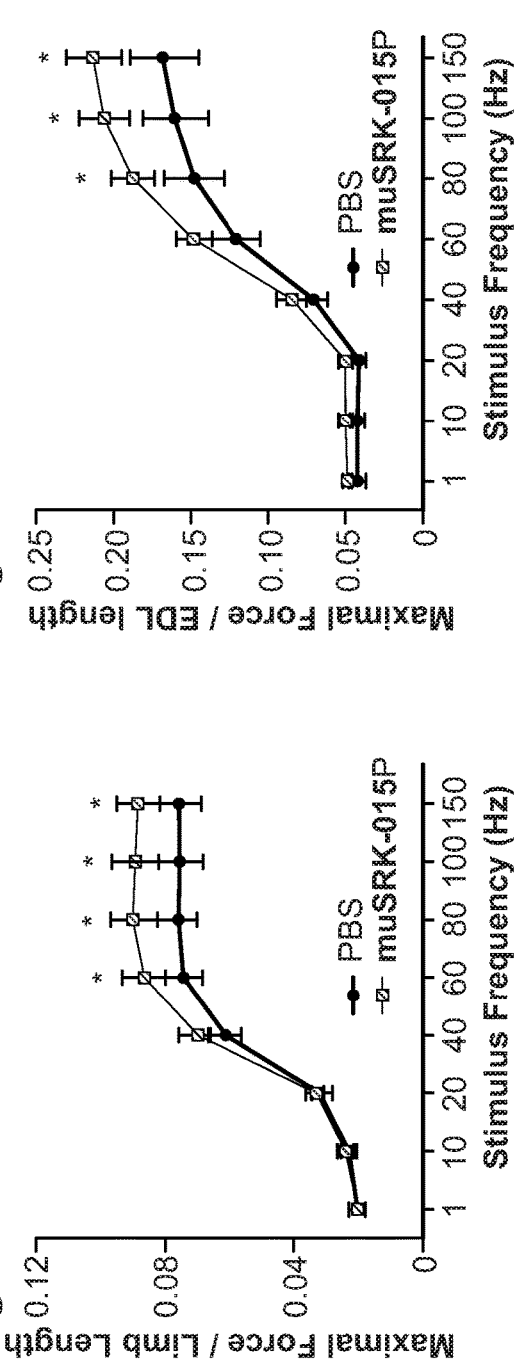
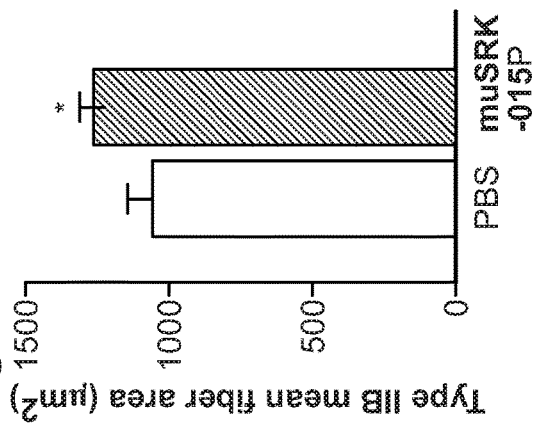
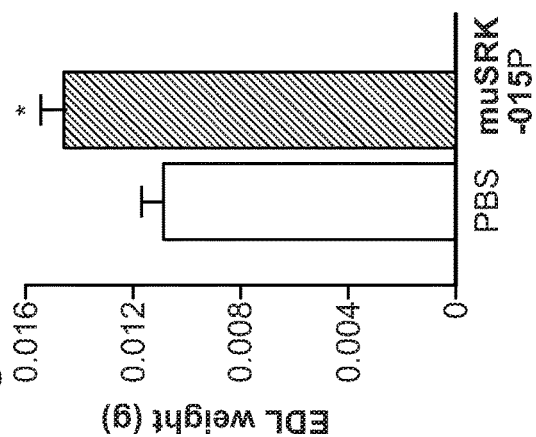
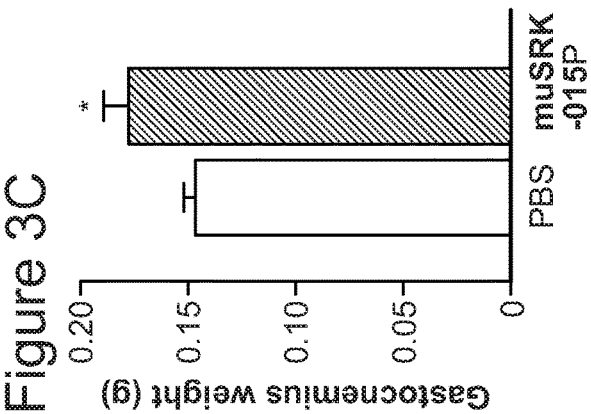

USE OF MYOSTATIN INHIBITORS AND COMBINATION THERAPIES

RELATED APPLICATIONS

This application is a 35 U.S.C. § 371 national stage filing of International Application No. PCT/US2017/037332, filed on Jun. 13, 2017, which in turn claims priority to U.S. provisional applications 62/349,596 filed Jun. 13, 2016, entitled "METHODS AND COMPOSITIONS FOR TREATING SPINAL MUSCULAR ATROPHY," 62/470,157 filed Mar. 10, 2017, entitled "USE OF MYOSTATIN INHIBITORS," 62/486,934 filed Apr. 18, 2017, entitled "USE OF MYOSTATIN INHIBITORS," 62/511,702 filed May 26, 2017, entitled "USE OF MYOSTATIN INHIBITORS," and 62/512,254 filed May 30, 2017, entitled "USE OF MYOSTATIN INHIBITORS," the entire contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 14, 2017, is named 127036-00120 SL.txt and is 79,104 bytes in size.

BACKGROUND

Myostatin, also known as growth differentiation factor 8, abbreviated GDF-8 or GDF8, is a key regulator of muscle homeostasis. Mutations that cause loss of myostatin, as well as pharmacological inhibition of myostatin activities, have shown to increase muscle growth in a number of species, including human. Such validations have prompted numerous groups over the last twenty years to develop an antagonist of the myostatin pathway as a therapeutic to treat muscle conditions, such as disuse atrophy, sarcopenia, and cachexia.

At least six myostatin inhibitor drug candidates, including small molecules and biologics, have entered the clinic in recent years and have failed due to unwanted side effects (e.g., risk of toxicity), lack of meaningful efficacy, or both. In many cases, satisfactory preclinical results have not successfully translated into a safe and effective drug, despite the fact that biological role of myostatin in regulating muscle growth is undisputed. Lack of translational success in the clinical development of myostatin inhibitors in a number of muscle conditions, including muscular dystrophy, cachexia, sarcopenia, sporadic inclusion body myositis (SIBM) and disuse, has presented a conundrum in the field.

SUMMARY OF THE INVENTION

The present invention encompasses the recognition that in vivo effects of myostatin inhibition depends on the biological context. According to the invention, factors that confer the responsiveness of a target muscle to a myostatin inhibition therapy include i) the anabolic state of a target muscle, ii) the degree of functional innervation by a motor neuron, and optionally, iii) the type of muscle fibers contained in the target muscle. Accordingly, as described in further detail herein, these factors should be taken into consideration for maximizing or improving benefits of myostatin inhibition.

The inventors of the present disclosure have identified a set of criteria which may provide a useful guidance for determining biological contexts (e.g., clinical conditions) in which myostatin inhibition may exert optimal effects on muscle:
 i) the muscle to be treated for promoting hypertrophy has retained or regained sufficient anabolic capacity;
 ii) the muscle to be treated for promoting hypertrophy and/or for preventing atrophy has retained or restored at least partial functional innervation of a motor neuron; and further in some cases,
 iii) the muscle to be treated is required for motor function that relies on fast-twitch (e.g., type II) fibers.

The profile of suitable clinical attributes identified herein, which may determine the likelihood of responsiveness to myostatin inhibition in muscle, therefore provides guidance for selecting suitable clinical indications and for identifying patient populations likely to benefit from such therapy. In some instances, where one or more of the attributes are lacking or insufficient in a patient, an additional agent(s) (e.g., therapeutics) may be co-administered to compensate for the deficiency in order to enhance or optimize efficacy. Combination therapies incorporating such agent(s) in conjunction with an inhibitor of myostatin are therefore encompassed by this invention.

Accordingly, the present invention provides various embodiments of methods for treating a muscle condition in a subject. Such methods comprise the step of: administering to the subject a therapeutically effective amount of a myostatin inhibitor to enhance muscle/motor function, provided that: i) the target muscle has retained or regained intact anabolic capacities, where intended clinical outcome includes promoting muscle hypertrophy; ii) the target muscle has retained or restored at least partial innervation of a functional motor neuron, where intended clinical outcome includes promoting muscle hypertrophy and/or preventing muscle atrophy; and/or, iii) the target muscle affected in the muscle condition contains or is enriched with fast twitch fibers, which are predominantly type II fibers.

In some embodiments, the subject has retained anabolic capacities (ability to grow) in the target muscle. Such subject may be a pediatric patient. In other embodiments, the subject has weakened or compromised anabolic capacities in the target muscle but has regained sufficient anabolic capacities. Limited anabolic capacities may be due to age, medical condition (injury, disease, etc.), side effects of a medication, general health status, or any combination thereof. In some embodiments, the subject has Amyotrophic lateral sclerosis (ALS), sarcopenia, cachexia, SIBM, immunodeficiency, muscular dystrophy, or any combination thereof. In some embodiments, the subject has been treated with an anabolic stimulator, e.g., an agent that boosts cellular anabolic pathways. In some embodiments, the subject receives a combination therapy comprising the myostatin inhibitor and the anabolic stimulator.

In some embodiments, the subject has retained at least partial functional innervation of the target muscle by a motor neuron, e.g., functional neuromuscular junction. In some embodiments, the subject has a condition associated with partial denervation of motor neurons. In some embodiments, the subject has a condition associated with impaired neurotransmission. In some embodiments, the impaired neurotransmission comprises hyperexcitability of the neuron, impaired trafficking or release of synaptic vesicles, and/or impaired function or availability of mitochondria to support neuromuscular signaling. In some embodiments, the subject has restored or strengthened at least partial functional motor neuron innervation of the target muscle, and/or at least partially normalized neurotransmission between the motor neuron and the target muscle. In some embodiments, the subject is treated with an agent that promotes the function of the motor neuron (i.e., neuronal therapy). In some embodiments, such agent at least partially corrects neurotransmission and/or membrane excitability. In some embodiments, the agent is a corrector of a genetic defect. In some embodiments, the subject is treated with an agent that corrects the genetic defect, aimed to promote the function of the motor neuron so that at least partial innervation or function may be sustained or regained (restored).

In some embodiments, the subject has spinal muscular atrophy (SMA). In some embodiments, the genetic defect is a mutation in survival motor neuron 1 (SMN1). In some embodiments, the agent (e.g., corrector agent) is a splice modifier, or a gene therapy. In some embodiments, the splice modifier is a small molecule agent; in other embodiments, the splice modifier is a nucleic acid agent, such as an RNA-based agent. In some embodiments, the corrector therapy promotes the function and/or survival of the motor neuron. In some embodiments, the corrector therapy delays the progression of SMA.

In some embodiments, the subject has been treated with a corrector agent, and/or is likely to be treated with a corrector agent. For example, the subject is treated with a corrector agent within about six months of myostatin inhibitor therapy, e.g., within about six months before or after the administration of the myostatin inhibitor. In some embodiments, such subject has or diagnosed with non-ambulatory SMA. In some embodiments, such subject has type I SMA, type II SMA, or non-ambulatory type III SMA.

According to the invention, an effective amount of the myostatin inhibitor to treat a muscle condition is an amount that achieves both clinical efficacy and safety. In some embodiments, the effective amount is an amount that enhances muscle function, such as force generation and motor function. In some embodiments, the effective amount is an amount that enhances motor function that requires fast-twitch fibers (e.g., type II fibers). In some embodiments, the motor function comprises eccentric contraction of a muscle. In some embodiments, an effective amount of the myostatin therapy is an amount sufficient to delay or alleviate progression of disease (e.g., muscle atrophy); maintain disease status (e.g., as measured/monitored by a suitable motor function test, plasma protein markers, metabolic markers, etc.); delay loss of α-motor neurons; prevent or delay expression of immature muscle markers; prevent, alleviate or delay intramuscular fat deposits (e.g., fatty replacement of muscle tissue); prevent metabolic dysregulation; prevent or reduce bone loss or frequency of bone fracture; increase an Expanded Hammersmith Functional Motor Scale score by ≥1 point1 as compared to control that does not receive the myostatin inhibitor; slow the rate of deterioration; delay regression (e.g., progressive decrease) of an Expanded Hammersmith Functional Motor Scale over a period of 12 months, 24 months or 36 months; and/or, increase a CHOP INTEND score by ≥1 point as compared to control that does not receive the myostatin inhibitor; and/or, increase a MFM-32 score by ≥1 point as compared to control that does not receive the myostatin inhibitor.

In some embodiments, the muscle condition to be treated with a myostatin inhibitor is associated with a neuromuscular disease, including but are not limited to: Amyotrophic lateral sclerosis (ALS); Congenital myasthenic syndrome; Congenital myopathy; Cramp fasciculation syndrome; Duchenne muscular dystrophy (DMD); Glycogen storage disease type II; Hereditary spastic paraplegia; Inclusion body myositis (IBM); Isaac's Syndrome; Kearns-Sayre syndrome; Lambert-Eaton myasthenic syndrome; Mitochondrial myopathy; Muscular dystrophy; Myasthenia gravis; Myotonic dystrophy; Peripheral neuropathy; Spinal and bulbar muscular atrophy; Spinal muscular atrophy (SMA); Spinal muscular atrophy with respiratory distress type 1; Stiff person syndrome; Troyer syndrome; and, Guillain-Barré syndrome.

In some embodiments, the muscle condition to be treated with a myostatin inhibitor according to the present invention is spinal muscular atrophy (SMA).

In embodiments where the neuromuscular disease is SMA, the genetic defect may include a mutation in the SMN1 gene. In order to promote the function of the motor neuron affected by the mutation, the subject may be treated with a corrector agent aimed to correct the genetic defect. In some embodiments, the agent is a splice modifier, which may be a nucleic acid-based (e.g., RNA-based) agent or small molecule agent. In some embodiments, the subject is treated with a corrector agent within about six months of receiving a myostatin inhibitor, e.g., within about six months prior to or about six months after the administration of the myostatin inhibitor.

The invention further contemplates that suitable inhibitors of myostatin signaling may be used as monotherapy (without the SMN corrector) for the treatment of less severe forms of SMA, in which the patient has retained the ability to be ambulatory. Patients suitable for such therapy include those with ambulatory type III SMA and type IV SMA. In some embodiments, such treatment may delay the progression of SMA, such that the patient remains ambulatory longer than control before the pathology transitions to a non-ambulatory form.

BRIEF DESCRIPTION OF THE FIGURES

FIG. 2A illustrates the experimental model of single-dose SRK-015 treatment in healthy and atrophy-induced mice; FIG. 2B provides changes in gastrocnemius muscle weights measured at the indicated time points.

FIGS. 3A-3E provide five graphs showing that administration of muSRK-015P in health animals enhances muscle function. (FIG. 3A) Maximum force generated by the gastrocnemius (normalized to limb length) as a function of stimulus frequency in muSRK-015P-treated and control mice; (FIG. 3B) maximum force of the EDL per muscle length as a function of stimulus frequency in muSRK-015P-treated and control mice; (FIG. 3C & FIG. 3D) GA and EDL muscle weights respectively in muSRK-015P-treated and control mice; and, (FIG. 3E) type IIB mean fiber area in muSRK-015P-treated and control mice.

(FIG. 5B) mean myofiber cross sectional area; and, (FIG. 5C) myofiber cross sectional area frequency distribution, in Δ7 SMA mice treated with an SMN corrector and muSRK-015P or vehicle.

(FIG. 6B) hind limb grip strength, in an acute contusion spinal cord injury model.

FIG. 7C shows TGX stain free gels which allows visualization and quantitation of total lane protein content for normalization upon UV imaging. Quantitation of latent myostatin signal in muscle of a mice treated with the muSRK-015P compared to the latent myostatin present in WT mice is shown in FIG. 7D.

FIG. 9A shows SRK-015 concentrations in the serum during the week following the first antibody dose. FIG. 9B shows SRK-015 concentrations in the serum during the final five weeks of the study following the last of 8 weekly antibody doses.

FIG. 10A shows increased mass in Gastrocnemius muscle following SRK-015 treatment. FIG. 10B shows increased mass in Biceps brachii muscles following SRK-015 treatment. Timecourse of target engagement in serum from monkeys was analyzed by semi-quantitative western blot analysis. Target engagement data from monkeys administered 3 mg/kg or 30 mg/kg weekly of SRK-015 is shown in FIG. 10C. SRK-015 engaged latent myostatin at both doses tested as shown in FIG. 10D.

DETAILED DESCRIPTION OF CERTAIN EMBODIMENTS

Figure 1:
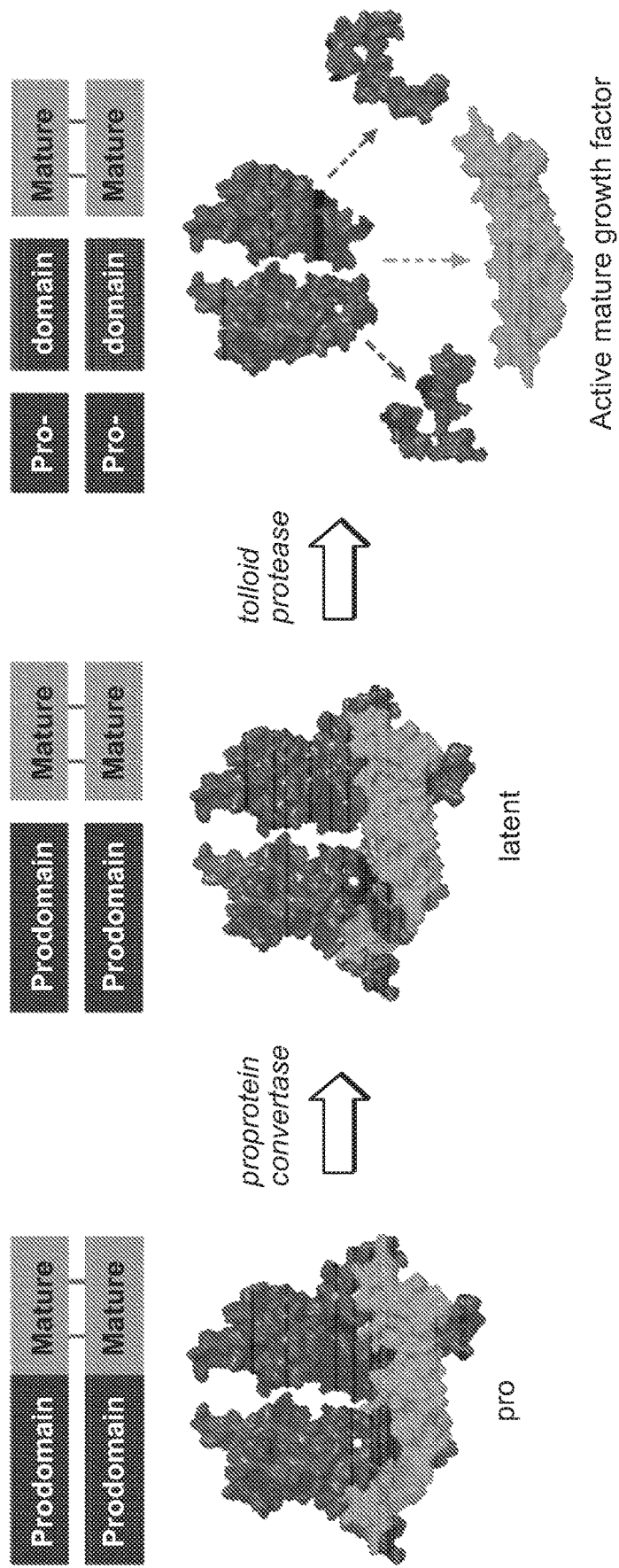
FIG. 1 provides a schematic of myostatin activation. Each precursor polypeptide of the dimer includes a prodomain and a growth factor domain. The first proteolytic step by a proprotein convertase cleaves the proMyostatin between the prodomain and the growth factor domain, producing a latent form of myostatin. In this form the prodomain is still physically associated with the growth factor domain. A Tolloid protease subsequently cleaves latent myostatin, after which active, mature myostatin is released from the latent complex.

The present invention is based, at least in part, on the recognition that effectiveness of myostatin inhibition depends at least in part on the status of the target muscle and that certain conditions must be met to confer benefits on muscle function. According to the invention, myostatin inhibition is particularly suited for treating clinical indications with the following attributes: i) the muscle to be treated has retained or regained intact/robust anabolic capacity (e.g., younger subjects); ii) the muscle to be treated (i.e., target muscle) has retained or regained at least partial functional innervation by a motor neuron (e.g., sufficient neuromuscular signaling between the target muscle and an innervating motor neuron); and/or, iii) the muscle to be treated is required for motor function that relies on type II fibers, e.g., unmet medical need is served by boosting the function of fast-twitch (glycolytic) muscle fibers, and the assessment of a motor outcome is driven by fast-twitch fiber activity. Based on these attributes, various embodiments of therapies and combination therapies are disclosed herein.

In the context of the present application, the term "combination therapy" refers to co-administration of two or more biologically active agents (e.g., drugs) used in conjunction with each other. Combination therapy may comprise a single formulation or multiple formulations. Co-administration may be carried out as concurrent administration or serial administration. Co-administration may be carried out via the same route of administration or different routes of administration. It is construed as combination therapy so long as effects of the two (or more) therapeutics overlap in the subject for purposes of achieving supplemental, additive or synergistic clinical effects.

Criterion (i) above sets forth that the target muscle is sufficiently active in that it has maintained or restored the ability to synthesize cellular components (e.g., constructive metabolism (i.e., anabolism)), as opposed to favoring the breakdown of cellular components. Thus, muscle with anabolic capacities has the ability to grow ("hypertrophy") rather than waste away ("atrophy"). While myostatin has been long validated as a negative regulator of muscle mass—indeed, a number of groups have tested myostatin inhibitors in a variety of muscle conditions but failed to generate clinically meaningful results—to date these studies have neglected to account for the importance of this "anabolic" background against which myostatin inhibition may exert its effects on promoting muscle growth. In fact, most of the clinical indications in which myostatin inhibitors have been tested to date involve patient populations whose muscles are inclined to be in catabolic states. Together with the notion that factors regulating muscle synthesis and muscle breakdown are in a dynamic equilibrium, the inventors of the present application recognized that inhibiting myostatin signaling can produce muscle-enhancing effects, to the extent that the target muscle also retains sufficient anabolic activities, which would drive protein synthesis.

To satisfy the criterion (i) above, two scenarios may be considered. In the first scenario, this criterion may naturally be met for younger individuals (e.g., pediatric patients and young adults) who are in a growth phase or with robust metabolism, where the cellular anabolic pathways are already robust and active. Thus, these patient populations have a favorable background against which myostatin inhibition produces clinical effects and are more likely to be responsive to a myostatin inhibition therapy, which can promote muscle growth. In the second scenario, where a patient population to be treated with a myostatin inhibitor is typically older individuals or those otherwise considered to have lost at least some of the anabolic machinery or its function (e.g., those suffering from sarcopenia, cachexia, immunodeficiency, infections, etc.), myostatin inhibition may not produce desirable benefits due to the lack of sufficient anabolic activities. However, such deficiencies may be overcome or compensated by co-administration of a second agent aimed to boost the patients' anabolic capacities, which may render the patient more responsive to concurrent administration of a myostatin inhibitor in promoting muscle hypertrophy. Thus, the invention includes combination therapies for the treatment of a muscle condition in a subject in a catabolic state, wherein the combination therapy comprises a myostatin inhibitor (i.e., an agent that inhibits myostatin activation, activities and/or signaling) and an anabolic stimulator (i.e., an agent that boosts anabolic function or favors protein synthesis). These agents are administered to the subject in amounts effective to enhance muscle growth (e.g., favor muscle synthesis over muscle breakdown) and to improve corresponding motor function.

As used herein, the term "catabolic state" means that the balance of synthesis and breakdown (e.g., protein synthesis and protein breakdown) in a target tissue/cell tips towards the latter such that there is a net catabolic effect in the target. Similarly, as used herein, the term "anabolic state" means that the balance of synthesis and breakdown (e.g., protein synthesis and protein breakdown) in a target tissue/cell tips towards the former such that there is a net anabolic effect in the target. Thus, for a patient population in a catabolic state, therapies that incorporate both an inhibitor of myostatin and an anabolic stimulating agent may achieve improved clinical benefits of the myostatin inhibition, as compared to a monotherapy. Typically, the state of the target tissue (e.g., muscle) is measured determining the circulating levels of various hormones (e.g., IGF-1, testosterone) and/or determining the levels of muscle protein synthesis. Measuring hormone levels can be performed by methods known to a person of skill in the art including competitive immunoassays using serum, saliva or urine samples. Measuring muscle protein synthesis can be performed by methods known to a person of skill in the art including muscle biopsies.

Recognition of the importance of criterion (ii) is based on the finding that function of muscle and a motor neuron that innervates the target muscle (collectively referred to as a "motor unit") is at least in part inter-dependent and a degree of cross-talk (i.e., bidirectional signaling) between the two components (i.e., the neuronal component and the muscle component) is required for maintaining neuromuscular function. It is contemplated that for myostatin inhibition to produce meaningful effects on the function of the target muscle, the muscle must receive sufficient nerve input from the innervating motor neuron (i.e., presence of functional neuromuscular signaling). This is likely relevant to both clinical contexts in which desired primary outcome is to promote muscle growth and to prevent muscle loss. As demonstrated in the Example below, in multiple muscle injury models, myostatin inhibition is able to prevent or mitigate injury-induced muscle atrophy, as well as metabolic dysregulation. In these animal models, the injured muscle at least partially retained nerve input, as opposed to a complete transection of the innervating motor nerves. Previous reports in the literature indicate that myostatin inhibition does not enhance muscle function in a complete spinal cord injury model. Without wishing to be bound by a particular theory, it is therefore contemplated that sufficient neuronal input (e.g., neurotransmission) from the innervating motor neuron at least in part contributes to the beneficial effects of myostatin inhibition in the target muscle. Typically, neurotransmission is measured in intact animals by directly stimulating a nerve (e.g., a nerve innervating a muscle) and measuring the contractions of the innervated muscle groups. In such measurements, lack of muscle contraction indicates the absence of neurotransmission. Similarly, incremental reductions of the response measured in the target muscle following repeated stimulation may be indicative of "fatigue" which may reflect an impairment in membrane excitability, synaptic vesicle trafficking, mitochondrial function/availability and/or glucose regulation. In SMA there is a progressive loss of fully innervated neuromuscular junctions, which can be assessed by immunofluorescence. Other electrophysiological methods known to a person of skill in the art can also be used measure neurotransmission (e.g., neuromuscular transmission.)

Requirement of sufficient neuronal signaling means that myostatin inhibitors may not produce optimal benefit if the nerve-muscle cross-talk is completely lost or destroyed (i.e., absence of functional neuromuscular signaling) either in injury or certain disease situations. This notion led the present inventors to recognize that, in neuromuscular diseases involving a genetic defect that impairs the motor neuron, the target muscle per se may still be intact during the early stage of the disease, but its function may gradually decline due to lack of sufficient neuronal input from the motor neuron to the muscle, as well as feedback to the motor neuron from the muscle (i.e., lack of functional neuromuscular signaling). It is therefore envisaged herein that an intervention (e.g., pharmacological intervention) to promote the nerve-muscle signaling, which targets and corrects or restores the underlining neuronal defect, should then enhance the benefit of myostatin inhibition.

Accordingly, the present invention includes combination therapies for the treatment of a neuromuscular disease. Such combination therapy comprises: i) an inhibitor of myostatin signaling (e.g., an agent that inhibits myostatin activation, activities and/or signaling), and, ii) a neuronal therapy (e.g., neuronal corrector, neuronal enhancer, etc.), which comprises an agent aimed to treat the motor neuron to correct a neuronal defect (such as a genetic mutation that causes the disease). The myostatin inhibitor and the agent to treat the motor neuron can be administered in conjunction with each other as combination therapy, in amounts effective to enhance motor function.

Suitable patient populations to receive a myostatin inhibition therapy for the treatment of neuromuscular disease include those who are on a neuronal therapy (e.g., who have received a neuronal corrector/enhancer). Based on the notion that the functional motor unit involves bidirectional signaling between the target muscle and the innervating motor neuron, it is contemplated that enhancing the function of one may positively affect the function of the other, and vice versa. Thus, a subpopulation of patients who have received but are not responsive to a neuronal therapy in a clinically meaningful way may be rendered more responsive to the neuronal therapy in conjunction with a myostatin inhibition therapy. Similarly, a subpopulation of patients who are responsive to a neuronal therapy may see further clinical benefits upon receiving a myostatin inhibition therapy.

In some embodiments, the methods of the present invention are suitable for treating or preventing muscle conditions or disorders and neuromuscular diseases. As used herein, the term "muscle condition" or "muscle disorder" refers to a disease, condition, or disorder, where the muscle does not function normally, or a disease, condition, or disorder, where the function of muscle is normal, but there are less force generated by the muscle due to a reduced amount of muscle available. As used herein, term "neuromuscular diseases" refers to any disease or that is caused by, or associated with, a disrupted signal transduction or a breakdown in communication between a neuron and a muscle tissue. In some embodiments, the impaired neurological signaling occurs due to a damage in the neuron structure, where neurons are incapable of transmitting signals towards their targets. In other embodiments, the structures of neurons remain intact, but there are functional disruption or defects, for example, a blockage at the neuromuscular junction, such that the ability of neurons to transmit signals is affected. In some embodiments, the disrupted signal transduction is associated with denervation, e.g., a partial loss or perturbation of nerve supply or neuronal input to its target muscle. In some embodiments, denervation is induced by injury. Suitable neuromuscular diseases or conditions which may be treated in accordance with the present invention include, but are not limited to: Amyotrophic lateral sclerosis (ALS); Congenital myasthenic syndrome; Congenital myopathy; Cramp fasciculation syndrome; Duchenne muscular dystrophy (DMD); Glycogen storage disease type II; Hereditary spastic paraplegia; Inclusion body myositis (IBM); Isaac's Syndrome; Kearns-Sayre syndrome; Lambert-Eaton myasthenic syndrome; Mitochondrial myopathy; Muscular dystrophy; Myasthenia gravis; Myotonic dystrophy; Peripheral neuropathy; Spinal and bulbar muscular atrophy; Spinal muscular atrophy (SMA); Spinal muscular atrophy with respiratory distress type 1; Stiff person syndrome; Troyer syndrome; and, Guillain-Barré syndrome.

In any of the above embodiments, co-administration of an agent aimed to enhance/promote neuronal function or correct/restore underlining neuronal defects (collectively referred to as "neuronal therapy"), and a myostatin inhibitor is useful. In addition, such combination therapy may further include an anabolic stimulating agent (i.e., anabolic stimulator) for patients whose target muscle may be in or at risk of being in the catabolic state. Such an anabolic stimulator may augment the benefit of the myostatin inhibitor, when used in combination. Thus, the invention includes a method for treating a neuromuscular disease in a patient, comprising administering to the patient an effective amount of combination therapy comprising a myostatin inhibitor, a neuronal enhancer/corrector (i.e., neuronal therapy), and an anabolic stimulator.

Figure 12:
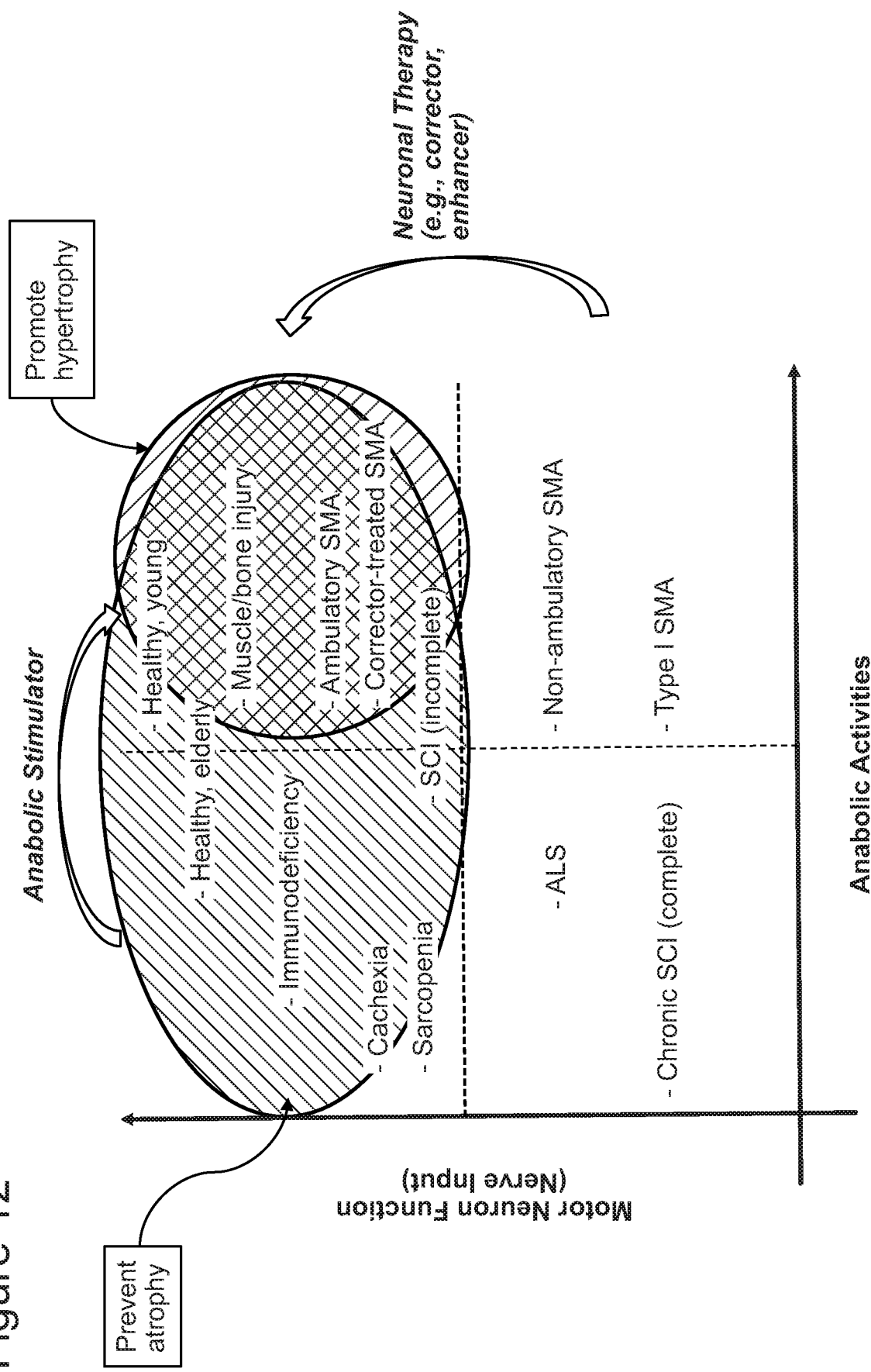
FIG. 12 is a schematic illustrating selection of certain patient populations that are likely to benefit from myostatin inhibition either alone or in combination with an additional agent (e.g., anabolic stimulator and/or neuronal enhancer).

The recognition of the factors that may affect the outcome of myostatin inhibitor therapy as described above is further illustrated in FIG. 12.

Figure 2B:
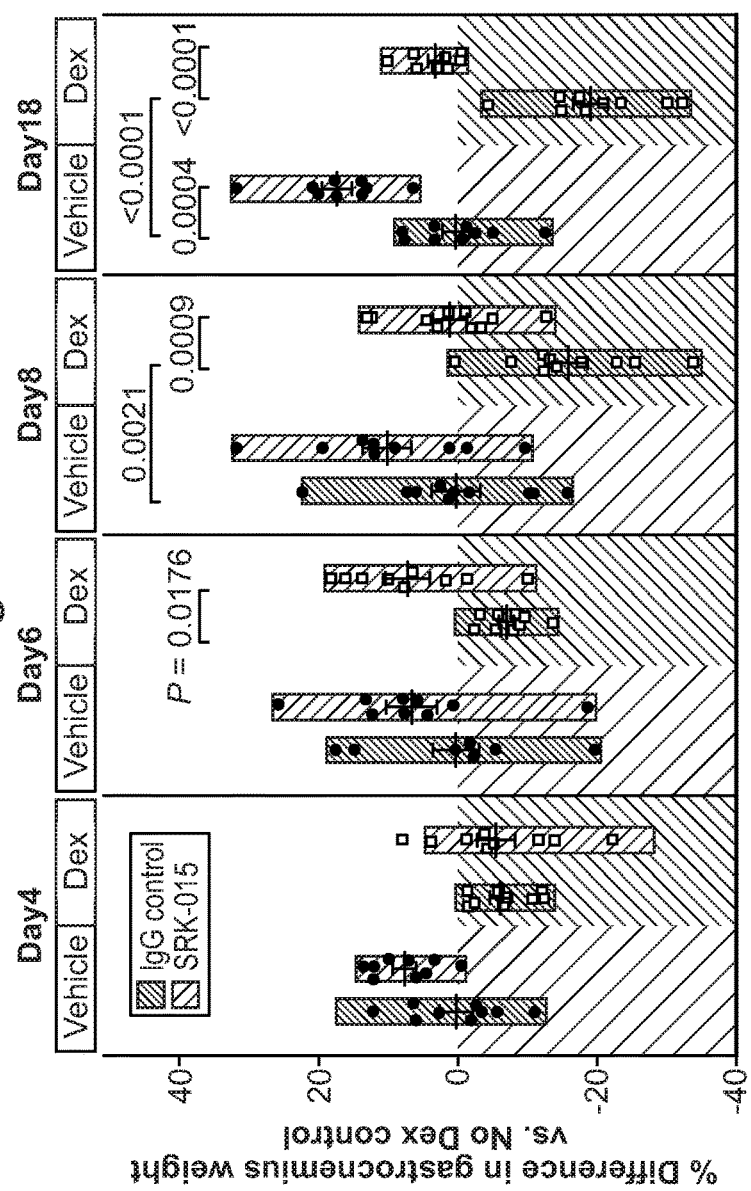
FIG. 2A and FIG. 2B provide a summary of dexamethasone-induced atrophy in mice.
Figure 2A:
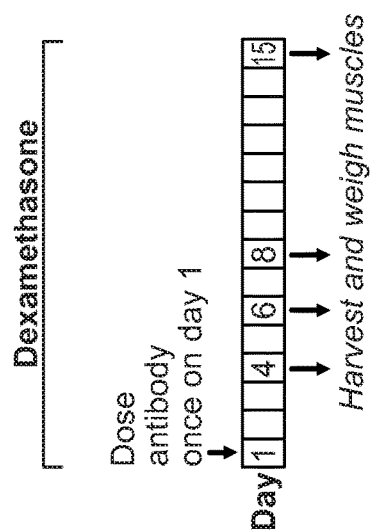

Criterion (iii) captures the notion that muscles are differentially affected by myostatin inhibition based in part on their fiber types. Evidence provided herein suggests that muscles that are enriched with fast-twitch fibers (such as type II fibers), including glycolytic, fast-twitch fibers, may be particularly sensitive to myostatin inhibition. Thus, myostatin inhibitor therapies may provide benefits preferentially to fast-twitch fiber-rich muscles (e.g., muscles containing type II fibers) and enhance motor function that requires or relies on fast-twitch fibers. As shown in FIG. 2, the gastrocnemius muscle was found to be responsive to myostatin inhibition therapy. It should be noted that gastrocnemius is known to contain about 75% fast-twitch glycolytic fibers.

Accordingly, the present invention is based, at least in part, on the recognition that patients suffering from a neurological disorder that impairs motor function may benefit from a combination of both an agent that targets muscle function (such as a muscle enhancer) and an agent that targets neuronal function (which may be generally referred to as "neuronal therapy"), such as splice modulators and gene correctors. The present invention is particularly useful for treating conditions that involve impaired signaling between a motor neuron and its target muscle (such as neuromuscular disorders). The present invention is particularly useful in the treatment of conditions involving partial but not complete loss of neurons that innervate muscle.

The invention includes the recognition that inhibition of myostatin signaling may be advantageous in treating conditions in which highly metabolic, fast-twitch fiber-rich muscles are particularly vulnerable. In particularly useful embodiments, therapeutic regimens to treat such conditions include an inhibitor or antagonist of myostatin signaling, in combination with an agent that treat the motor neuron innervating the fast-twitch fiber-rich muscle.

Such conditions may be associated with a genetic mutation that results in defective axonal transport or regulation thereof; defective vesicle trafficking or regulation thereof; defective neurotransmission or regulation thereof; defective mitochondrial function or availability; or any combinations thereof. In some embodiments, such generic mutation may cause defective energy production, energy consumption, glucose usage or regulation thereof.

In some embodiments, such condition is spinal muscular atrophy (SMA).

Definitions

The articles "a" and "an" are used herein to refer to one or to more than one (i.e., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages may mean ±1%. Furthermore, the term "about" can mean within ±1% of a value.

The terms "administer", "administering" or "administration" include any method of delivery of a myostatin inhibitor, neuronal corrector, e.g., SMN corrector, and/or anabolic stimulator, e.g., a pharmaceutical composition, into a subject's system or to a particular region in or on a subject (systemic and local administration, respectively).

The term "responder" as used herein, relates to patients for which the predicted response to a treatment/biological drug is positive. Similarly, the term "non-responder patient" as used herein, relates to patients for which the predicted response to the treatment/biological drug is negative, or absent. The term "poor responder," as used herein, refers to patients for which the predicted response to a treatment/biological drug is positive but does not achieve complete treatment of the disease/disorder and wherein the patient would benefit from additional therapy(ies) to achieve additional and/or improved clinical responses.

The term "predicted response" or similar, as used herein refers to the determination of the likelihood that the patient will respond either favorably or unfavorably to a given therapy/biological drug. Especially, the term "prediction", as used herein, relates to an individual assessment of any parameter that can be useful in determining the evolution of a patient. As it will be understood by those skilled in the art, the prediction of the clinical response to the treatment with a biological drug, although preferred to be, need not be correct for 100% of the subjects to be diagnosed or evaluated. The term, however, requires that a statistically significant portion of subjects can be identified as having an increased probability of having a positive response. Whether a subject is statistically significant can be determined without further effort by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90% at least 95%. The p-values are, preferably, 0.2, 0.1 or 0.05.

The term "clinical response", as used herein, refers to the response to a biological drug of the subject suffering from a pathology which is treatable with said biological. Standard criteria may vary from disease to disease and is discussed in more detail herein.

A patient who would "benefit from muscle growth" includes both healthy patients and patients having diseases and/or disorders with reduced muscle mass and/or muscle strength. In one embodiment, a patient who would benefit from muscle growth is a subject having a muscle disease or disorder, e.g., SMA.

As used herein the term "comprising" or "comprises" is used in reference to compositions, methods, and respective component(s) thereof, that are essential to the invention, yet open to the inclusion of unspecified elements, whether essential or not.

The term "consisting of" refers to compositions, methods, and respective components thereof as described herein, which are exclusive of any element not recited in that description of the embodiment.

The term "control" or "control sample," as used herein, refers to any clinically or scientifically relevant comparative sample, population, or counterpart, including, for example, a sample from a healthy subject, a sample from a subject having a deficiency that can cause or make the subject susceptible to a certain disease or condition, a subject with a disease or condition of interest, a sample from a subject treated with a pharmaceutical carrier, a sample from a subject prior to treatment, a sham or buffer treated subject or sample, an untreated subject or sample, and the like.

The term "control level" refers to an accepted or predetermined level of a biological marker, e.g., a level of a marker obtained before treatment or the onset of disease or before administration of a drug, e.g., a myostatin inhibitor or an SMN corrector. The level of a biological marker present in a subject or population of subjects having one or more particular characteristics, e.g., the presence or absence of a particular disease or condition, e.g., SMA.

The term "decrease", as used herein, in the context of a disease symptom refers to a statistically significant decrease in such level. The decrease can be, for example, at least 5%, 10%, 15%, 20%, 25%, 30%, 35%, 40%, 45%, 50%, 55%, 60%, 65%, 70%, 75%, 80%, 85%, 90%, or 95%, or below the level of detection for the detection method. The decrease can also be, for example, about 1-10%, 10-20%, 1-30%, 20-50%, 30-60%, 40-70%, 50-80%, or 60-90% below the level of detection for the detection method. In certain embodiments, the reduction is down to a level accepted as within the range of normal for an individual without such disorder which can also be referred to as a normalization of a level.

The term "increase" in the context, e.g., of a disease symptom, such as for example, a loss of function or loss of mass, e.g., muscle mass associated with a disease, refers to a statistically significant increase in such level. The increase can be, for example, at least 5%, 10%, 15%, 20%, 25%, 30%, 35%, 40%, 45%, 50%, 55%, 60%, 65%, 70%, 75%, 80%, 85%, 90%, or 95%, or above the level of detection for the detection method. The increase can also be, for example, about 1-10%, 10-20%, 1-30%, 20-50%, 30-60%, 40-70%, 50-80%, or 60-90% above the level of detection for the detection method. In certain embodiments, the increase is up to a level accepted as within the range of normal for an individual without such disorder which can also be referred to as a normalization of a level. In certain embodiments, the increase is the normalization of the level of a sign or symptom of a disease, an increase in the difference between the subject level of a sign of the disease and the normal level of the sign for the disease.

As used herein, the term "denervation" refers to loss or perturbation of nerve supply or neuronal input to its target tissue, such as a muscle tissue. "Partial denervation" may therefore be associated with partially impaired neuromuscular signaling between a target muscle and an innervating motor neuron. Causes of denervation include disease (e.g., genetic disorders of motor neurons), chemical toxicity, physical injury, or intentional surgical interruption of a nerve and the like. Denervation may be partial denervation (also referred to as incomplete denervation) or complete denervation. Partial denervation can be, for example, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 95% loss or perturbation of nerve supply or neuronal input to its target tissue. In some embodiments, partial denervation includes about 1-10%, 10-20%, 1-30%, 20-50%, 30-60%, 40-70%, 50-80%, 60-90% of loss or perturbation of nerve supply or neuronal input to its target tissue. Partial denervation and neuromuscular damage are measured using, for example, compound muscle action potential and motor unit number estimation, as described in more detail herein.

"Determining" as used herein is understood as performing an assay or using a method to ascertain the state of someone or something, e.g., the presence, absence, level, or degree of a certain condition, biomarker, disease state, or physiological condition.

"Development" or "progression" of a disease means initial manifestations and/or ensuing progression of the disease. Development of the disease can be detectable and assessed using standard clinical techniques. However, development also refers to progression that may be undetectable. For purpose of this disclosure, development or progression refers to the biological course of the symptoms. "Development" includes occurrence, recurrence, and onset. As used herein "onset" or "occurrence" of a disease/disorder associated with myopathy includes initial onset and/or recurrence.

Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

As used herein, the terms "effective amount" and "effective dose" refer to any amount or dose of a compound or composition that is sufficient to fulfill its intended purpose(s), i.e., a desired biological or medicinal response in a tissue or subject at an acceptable benefit/risk ratio. For example, in certain embodiments of the present invention, the intended purpose may be to inhibit activation of myostatin in vivo, to achieve clinically meaningful outcome associated with the myostatin inhibition.

Measure of the relevant intended purpose may be objective (i.e., measurable by some assay or marker) or subjective (i.e., subject gives an indication of or feels an effect). In some embodiments, a therapeutically effective amount is an amount that, when administered to a patient population that meets certain clinical criteria for a disease, disorder or condition (for example, as determined by symptoms manifested, disease progression/stage, genetic profile, etc.), a statistically significant therapeutic response is obtained among the population.

In some embodiments, an effective amount is an amount that, when administered according to a particular regimen, produces a positive clinical outcome with a reasonably acceptable level of adverse effects (e.g., toxicity), such that the adverse effects, if present, are tolerable enough for a patient to continue with the therapeutic regimen, and the benefit of the therapy overweighs risk of toxicity. Those of ordinary skill in the art will appreciate that in some embodiments of the invention, a unit dosage may be considered to contain an effective amount if it contains an amount appropriate for administration in the context of a dosage regimen correlated with a positive outcome.

A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. In some embodiments, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts.

By "treating" or "preventing" a disease or disorder is meant delaying or preventing the onset of such a disease or disorder, reversing, alleviating, ameliorating, inhibiting, slowing down or stopping the progression, aggravation or deterioration, the progression or severity of a condition associated with such a disease or disorder, but not necessarily require a complete treatment or prevention of the disease or disorder. In one embodiment, the symptoms of a disease or disorder are alleviated by at least 5%, at least 10%, at least 20%, at least 30%, at least 40%, or at least 50%.

As used herein, the term "neuronal therapy" refers to an agent aimed to improve (e.g., enhance or restore) neuronal function. Neuronal therapies are useful for treating conditions that involve impaired signaling between a motor neuron and its target muscle (such as neuromuscular disorders). Specifically, neuronal therapies are particularly useful in the treatment of conditions involving partial but not complete loss of neurons that innervate muscle. In one embodiment, an "neuronal therapy" may be a gene therapy, a small molecule, or an antisense oligonucleotide, as described in more detail herein. In one embodiment, a "neuronal therapy" is a "SMN corrector," as described in more detail herein. In some embodiments, neuronal therapy is an agent that is capable of fully restoring motor neuron function in a cell (e.g., a cell within a subject). In some embodiments, a neuronal therapy is an agent that is capable of partially restoring motor neuron function in a cell (e.g., a cell within a subject). In some embodiments, a neuronal therapy is an agent that is capable of restoring at least 10%, 15%, 20%, 25%, 30%, 35%, 40%, 45%, 50%, 55%, 60%, 65%, 70%, 75%, 80%, 85%, 90%, 95%, 99%, or more of the motor neuron function in a cell (e.g., a cell within a subject). A skilled artisan will understand that motor neuron function typically includes membrane excitability, axonal transport, vesicle trafficking, neurotransmitter release, mitochondrial function, and/or mitochondrial availability, and such functions are measured using assays known to those of ordinary skill in the art.

Spinal Muscular Atrophy (SMA)

Spinal muscular atrophy (SMA) is a debilitating, frequently fatal neuromuscular disease and the most common genetic cause of infant mortality (1). It is one of the most common rare diseases—approximately 1 in 54 people are carriers, and 1 in ~11,000 children are born with SMA. SMA is an autosomal recessive genetic disorder involving a mutation or deletion in the Survival Motor Neuron 1 (SMN1) gene. Specifically, SMA is caused by reductions in the level of SMN protein, sufficient amounts of which are necessary to promote survival of the anterior horn cells of the spinal cord. Loss of motor neurons results in profound muscle atrophy, often leading to death due to respiratory insufficiency (2).

While SMA patients lack a functional SMN1 gene, the paralogous gene, SMN2, produces low levels of functional SMN protein due to alternative splicing that truncates the transcript. Suitable methods and compositions for treating SMA patients that are effective for preventing muscle atrophy and promoting neuronal survival are of great interest. SMA is clinically heterogeneous, with patients categorized based on the severity of their disease.

Type 0 is the most severe version of SMA, and is diagnosed prenatally with reduced fetal movement in utero. Patients require ventilator support at birth. Type 1 SMA is typically diagnosed between birth and 6 months, and patients never gain sufficient strength to sit independently. Without intervention most Type 1 patients do not survive past two years without respiratory support. People with Type II and Type III produce greater amounts of SMN protein and have less severe, but still life-altering forms of SMA. Type II patients are diagnosed between six and 18 months of age. While they are able to sit unassisted they cannot walk without aid. With Type III SMA, patients are diagnosed past the age of 18 months and are able to sit and walk unassisted, although they may become wheelchair dependent later in life. Type IV SMA is adult onset, mild in phenotype, and very rare (1, 3). Although SMA stratification by type is a useful clinical paradigm, the disease phenotype exists more as a continuum than as discreet classifications (4).

The clinical heterogeneity of SMA is due in part to the complicated genetics of the disease. Mutations in the SMN1 gene result in SMA (5); however, in humans, a nearly identical gene, SMN2, is located in close proximity to SMN1 (6). The primary difference between these genes is a C to T transition which creates an exonic splice silencer, resulting in removal of exon 7 from the final mRNA transcript. The truncated SMN protein is unstable and quickly degraded. Nevertheless, approximately 10% of the mRNA produced from SMN2 is correctly spliced and produces full length SMN protein, but this amount is insufficient to fully compensate for loss of SMN1. The copy number of SMN2 varies between individuals, with more copies (3 to 4) generally associated with milder forms of SMA (1-4).

Although the role(s) of SMN in regulating motor neuron survival and function have not been fully elucidated, its best characterized function is in snRNP biogenesis and pre-mRNA splicing (2). And while motor neurons appear to be particularly sensitive to reductions in SMN protein levels, SMN is ubiquitously expressed, and other organ systems are also affected in SMA patients, including the liver, spleen, gastrointestinal system, autonomic nervous system, and bone (3). As described above, severe skeletal muscle atrophy is observed in SMA patients and is primarily due to loss of motor neuron innervation, although muscles are not all equally affected, with axial muscles displaying generally greater atrophy and denervation than appendicular muscles (2, 7). In SMA patients the diaphragm is largely spared, due to the preservation of the phrenic nerve (8). Interestingly, fast twitch Type II muscle fibers display significantly greater atrophy than slow twitch Type I fibers (9). The degree of muscle atrophy is directly related to the degree of innervation, with muscles innervated by nerves less affected by loss of SMN protein displaying less atrophy (7, 8, 10). Nevertheless, SMN protein does appear to play a direct role in skeletal muscle, as myogenic cells isolated from mouse models of SMA display dysregulated myogenic gene expression and differentiate prematurely, leading to poor myotube formation (11, 12). In addition, evidence of muscle pathology is present in presymptomatic mice, and muscle specific deletion of SMN exon 7 leads to severe muscular dystrophy (13, 14).

Therapeutic Approaches for SMA—SMN Correctors

Multiple therapeutic approaches to restore SMN protein levels are under investigation: SMN1 gene replacement therapy, small molecules which modulate SMN2 splicing, and the use of antisense oligonucleotides (ASO) to block an SMN2 intronic splicing silencer, thus increasing exon7 inclusion.

SMN1 gene replacement therapy using adeno-associated viral vectors (AAV) has shown benefit in mouse models of SMA and AVXS-101, an AAV9-SMN1 vector from AveXis, is currently in Phase I clinical trials (see NCT02122952) (15).

Other approaches focus on modulating SMN2 splicing, such that exon 7 is retained in a greater percentage of transcripts, leading to increased production of full-length SMN protein. Novartis and PTC Therapeutics/Roche have both developed small molecules which selectively enhance SMN2 exon 7 inclusion, resulting in increased full-length SMN protein levels and therapeutic efficacy in mouse models of SMA (16-19). These small molecules from both companies are currently in Phase 2 clinical trials (see trials NCT02913482, NCT03032172, NCT02908685, NCT022688552). Oral dosing of RG7800, SMN-C2, and SMN-C3 in mild and severe preclinical models of SMA showed that the compounds increased SMN protein levels in both brain and muscle tissues in treated mice, as compared to vehicle. The molecules also efficiently crossed the blood brain barrier (BBB). In the severe SMA mouse model, both compounds normalized motor behavior and increased weight and survival compared with vehicle. However, the clinical program was put on hold due to safety concerns.

LMI070, another clinical-stage small molecule SMN2 splice modulator, was also discontinued after results from a preclinical animal study showed injuries to the peripheral nerves and spinal cord, testes, and blood vessels in the kidney.

One muscle-focused drug, CK-212107, to date targets skeletal muscle troponin to alter contractility.

Additional small molecule based SMN2 splice correctors are described in, for example, U.S. Patent Application Publication No.: US 2009/0031435, published Jan. 29, 2009; and U.S. Pat. No. 8,399,437, published Mar. 19, 2013; the contents of each are incorporated by reference herein in their entirety. It should be appreciated, however, that other small molecule splice correctors including SMN2 splice correctors known in the art and would be apparent to the skilled artisan, are within the scope of this disclosure.

A third approach is the use of antisense oligonucleotides (ASO), for example, to block an SMN2 intronic splicing silencer, thus increasing exon7 inclusion, again rescuing disease in mouse models of SMA (20-22). Biogen/Ionis have developed nusinersen, an ASO splice modifier which shows clinical efficacy and was recently approved by the FDA and marketed as Spinraza™ (23-25). However, each administration of Nusinersen requires intrathecal delivery under general anesthesia. Additionally, while the antisense corrector Nusinersen has proven promising, clinical efficacy appears modest: 60% of patients among infantile-onset SMA (type I) are reported to be non-responders, and 43% of Nusinersen-treated patients did not attain ≥3 point increase by Hammersmith Functional Motor Scale (Expanded) (HFMSE), while mean increase was less than 6 points in the treated patient group, as compared to placebo. Thus, only a partial improvement is achieved by Nusinersen treatment.

While these molecules have all shown significant efficacy preclinically, and Nusinersen clinically, none offers a complete cure for the disease. In mouse models, while both the small molecule and ASO splice modifiers significantly reduce disease severity, treated animals nevertheless have deficits in longevity, body weight, muscle mass, and muscle function compared to healthy animals (21, 26). In a double-blinded clinical trial in infantile-onset SMA, nusinersen resulted in clinically meaningful benefits at the time of interim analysis (41% of treated versus 0% placebo had improvements in motor milestones using the Hammersmith Infant Neurological Examination). The motor function milestones reached are impressive for Type I patients, with five of 81 treated patients able to sit unaided (a milestone almost never reached in these patients). Nevertheless, these patients have not achieved the full range of developmental milestones, and in a normal individual the achieved milestones would be considered disappointing (25). In a second placebo controlled trial in Type II SMA, nusinersen again showed clinically meaningful improvements, with scores on the Hammersmith Functional Motor Scale-Expanded (HFMSE) increasing by 5.9 points relative to the placebo group. Note that the maximum score on the HFMSE is 66 points, with most Type II patients scoring below 20 (27, 28). Nevertheless, 43% of patients failed to achieve at least a 3-point improvement in motor function in this trial (25). These results indicate that, while SMN2 splice modulators have potential for significant effects on SMA disease course patient quality of life, additional functional gains are needed to further improve reduce disease burden.

As used herein, the term "SMN corrector" refers to any therapy or compound which can be used to increase or improve SMN gene expression (e.g., SMN1 gene expression and/or SMN2 gene expression), SMN protein production, and/or functional SMN activity. SMN correctors, for example, include splice correctors/modifiers that alter the splicing of SMN2 transcripts. It should be noted that systemically delivered SMN splice modifiers may also affect SMN splicing in other (i.e., non-neuronal) tissues, where SMN is expressed.

An "SMN corrector" may be a central corrector or a systemic corrector. A central corrector is administered directly to the central nervous system (CNS) via the intrathecal route. In contrast, a systemic corrector may be administered via any route, e.g., orally administered, and affects not only the CNS, but other tissues throughout the body.

In some embodiments, a "functional SMN protein" is capable of promoting motor neuron function and/or survival.

In some embodiments, a "functional SMN protein" is capable of fully restoring motor neuron function in a cell (e.g., a cell within a subject). In some embodiments, a functional SMN protein is capable of partially restoring motor neuron function in a cell (e.g., a cell within a subject). In some embodiments, a functional SMN protein is capable of restoring at least 10%, 15%, 20%, 25%, 30%, 35%, 40%, 45%, 50%, 55%, 60%, 65%, 70%, 75%, 80%, 85%, 90%, 95%, 99%, or more of the motor neuron function in a cell (e.g., a cell within a subject). In some embodiments, full-length SMN protein is the result of protein translation (e.g., in a cell) of a correctly spliced SMN mRNA. In some embodiments, a functional SMN protein is encoded from SMN2 mRNA that contains exon 7.

In one embodiment, an "SMN corrector" may be a gene therapy, a small molecule, or an antisense oligonucleotide, as described in more detail herein. In some embodiments, a SMN corrector is an oligonucleotide molecule. In some embodiments, a SMN corrector is an antisense molecule. In some embodiments, a SMN corrector may be an antisense molecule that increases expression of an SMN2 gene. In some embodiments, a SMN corrector may be an antisense molecule that increases expression of an SMN2 mRNA that contains exon 7. In some embodiments, a SMN corrector may be an antisense molecule that increases expression of functional SMN protein, for example, SMN protein encoded by SMN2 mRNA that contains exon 7. For example, antisense oligonucleotides directed to inhibit an intronic splice silencer site (ISS) in intron 7 of the SMN2 gene can modulate pre-mRNA processing, leading to a greater probability of exon 7 inclusion within the mature mRNA transcript of SMN2, resulting in the increased production of functional SMN protein.

The terms "splice corrector", "splice modulator" and "splice modifier", as used herein, are interchangeable and refer to an agent that corrects aberrant splicing of RNA transcripts, such as those encoded by the SMN2 gene and/or modulates expression of a SMN protein. In some embodiments, SMN2 splice correctors increase the inclusion of exon 7 in the SMN2 pre-mRNA. In some embodiments, increased inclusion of exon 7 in the SMN2 pre-mRNA leads to increased expression of a functional SMN protein (e.g., from an SMN2 gene) in a cell or subject, such as an SMN protein that is capable of promoting neuron function and/or survival.

In one embodiment, an SMN corrector may be a gene therapy. As used herein, the term "gene therapy" refers to any procedure that uses nucleic acids to heal, cure, or otherwise improve a condition in a subject. In gene therapy, nucleic acids need to be delivered into specific cells. Delivery methods include viral and non-viral means, which are known in the art. See, for example, Patil et al., AAPS J. 7(1): E61-E77 (2005); Gascon et al., Non-Viral Delivery Systems in Gene Therapy (2013); Somiari et al., Molecular Therapy, 2(3), 178-187 (2000); Herweijer, H., and J. A. Wolff, Gene therapy 10(6): 453-458 (2003); and Nayerossadat et al., Advanced biomedical research 1(2):1-11 (2012). Viral means for delivering gene therapy involve the use of viral vectors. Viral vectors are genetically modified viruses that can carry a therapeutic genetic payload and have been reprogrammed to allow for infection and subsequent transmittal of said payload into specific tissues without the side effects typically associated with wild-type viral infection. A number of viruses can be used as viral vectors, including retroviruses, adenoviruses, herpes simplex virus, lentiviruses, Poxvirus, and Epstein-Barr virus. While safer than wild-type viruses, viral vectors may induce an immune response, occasionally necessitating the use of non-viral delivery methods. In one embodiment, the viral vector is an AAV viral vector. Non-viral delivery methods include, but are not limited to, physical methods, such as injection of naked DNA, electroporation, gene gun bombardment, and ultrasound, as well as biochemical methods. Another delivery technique, magnetofection, combines physical and biochemical elements.

In some embodiments, an "effective amount" of a SMN corrector is an amount of an agent that is capable of fully restoring motor neuron function in a cell (e.g., a cell within a subject). In some embodiments, a SMN corrector is an agent that is capable of partially restoring motor neuron function in a cell (e.g., a cell within a subject). In some embodiments, an "effective amount" of a SMN corrector is an amount of an agent that is capable of restoring at least 10%, 15%, 20%, 25%, 30%, 35%, 40%, 45%, 50%, 55%, 60%, 65%, 70%, 75%, 80%, 85%, 90%, 95%, 99%, or more of the motor neuron function in a cell (e.g., a cell within a subject). A skilled artisan will understand that motor neuron function typically includes membrane excitability, axonal transport, vesicle trafficking, neurotransmitter release, mitochondrial function, and/or mitochondrial availability.

In some embodiments, a SMN corrector is an agent, for example, a small molecule or an oligonucleotide (e.g., an antisense oligonucleotide), that increases expression of a functional SMN protein, for example, by promoting the inclusion of exon 7 in an SMN2 mRNA transcript. In some embodiments, the cell is a cell within a subject, for example, a subject that is administered a SMN corrector. In some embodiments, a SMN corrector increases the relative amount of SMN2 mRNA that includes exon 7 as compared to SMN2 mRNA that does not include exon 7 in a cell, for example, a cell in a subject. In some embodiments, an "effective amount" of a SMN corrector increases the amount of correctly spliced SMN2 mRNA in a cell (e.g., a cell within a subject), such that at least 10%, 15%, 20%, 25%, 30%, 35%, 40%, 45%, 50%, 55%, 60%, 65%, 70%, 75%, 80%, 85%, 90%, 95%, 99%, or more of the SMN2 mRNA within a cell contains exon 7. In some embodiments, an "effective amount" of a SMN corrector increases a level of SMN2 mRNA containing exon7 in a subject by at least 5%, 10%, 20%, 30%, 40%, 50%, 60%, 70%, 80%, 90%, 100%, 150%, 200%, 400%, 500%, 600%, 700%, 800%, 900%, 1000%, or more. In some embodiments, an "effective amount" of a SMN corrector increases a level of functional SMN protein in a subject by at least 5%, 10%, 20%, 30%, 40%, 50%, 60%, 70%, 80%, 90%, 100%, 150%, 200%, 400%, 500%, 600%, 700%, 800%, 900%, 1000%, or more.

Targeting Myostatin to Improve Muscle Function—Myostatin Inhibitors

One therapeutic approach to improve patient motor function is to directly target the skeletal muscle to reduce muscle atrophy and thus improve muscle strength in subjects having muscle conditions, such as SMA. Inhibition of myostatin (also known as Growth and Differentiation Factor 8, or GDF-8) offers a promising approach to increase muscle mass and function in patients having muscle conditions, such as SMA patients. Myostatin is a member of the TGFβ superfamily and a critical negative regulator of muscle growth. Genetic loss of myostatin results in significantly increased muscle mass, resulting from both muscle cell hypertrophy and hyperplasia (29). As with myostatin loss of function mutations, pharmacologic inhibition of myostatin also increases muscle mass, mediated via muscle hypertrophy but not hyperplasia (30). Additionally, evidence in animal models suggests that blockade of myostatin signaling prevents muscle atrophy associated with limb immobilization, cancer cachexia, and corticosteroid treatment (31-34). Since the initial description of the knockout mouse, mutations in myostatin and associated muscle hypertrophy have been identified in cattle, dogs, and humans. Loss of myostatin does not appear to cause any detrimental effects (35-37).

The profound effects of myostatin loss on muscle mass, as well as the lack of observed pathology with myostatin mutations, has made this growth factor an important therapeutic target for indications in which muscle wasting is a significant feature, including sarcopenia, cancer cachexia, muscular dystrophy, and disuse atrophy (38). Multiple companies are pursuing a variety of approaches to inhibit myostatin and therefore increase muscle mass and strength. The most common approaches to myostatin inhibition are (1) antibodies which bind to and inhibit the mature growth factor (commonly referred to as "neutralizing" antibodies), (2) antibodies against the myostatin receptor, ActRIIB, (3) soluble ligand traps such as ActRIIB-Fc, and (4) viral mediated expression of myostatin inhibitors, such as follistatin (39-43). However, in addition to targeting myostatin, many of these therapies also inhibit related family members such as GDF11 and Activins. The amino acid sequences of mature myostatin and GDF11 are 90% identical, making it extremely difficult to generate antibodies that specifically bind myostatin but not GDF11. Myostatin, GDF11, and Activins all signal through ActRIIB; as such, antibodies that block ActRIIB or soluble ActRIIB ligand traps will therefore inhibit activities of all three growth factors (44). Follistatin in an endogenous inhibitor of myostatin, which also binds and inhibits GDF11 and Activins (45). Several of these molecules also bind more distantly related growth factors, such as BMP9 and BMP10, albeit with reduced affinity. This lack of specificity has the potential for unwanted side effects. While a clear role for GDF11 during development has been elucidated, its biological role postnatally, and the effects of GDF11 inhibition, are unclear. GDF11 has been suggested as both a pro- and anti-aging factor, and both beneficial and detrimental to muscle growth and regeneration (46-53). Activin A is crucial for multiple reproductive functions, including release of follicle stimulating hormone, follicle development, and endometrial repair following menstruation (54). BMP9 is involved in maintenance of vascular epithelium integrity, and inhibition of this ligand is thought to have led to telangiectasias and gingival bleeding observed in patients treated with ACE-031, an ActRIIb-Fc fusion (41). Together, these observations point to the importance of developing selective inhibitors of myostatin signaling, so as to minimize risk of adverse effects that may be caused by inadvertently inhibiting the signal transduction pathways of one or more of the related growth factors. The inventors of the present disclosure have recognized that specificity of myostatin inhibition is of particular importance to minimize risk of toxicities, for treating younger patients who are still in a growth phase, as well as in patients who are in need of receiving a long-term therapy, which in some cases involves life-time management of a disease.

Various myostatin inhibitors in development, such as those listed above, all significantly increased muscle mass and strength in rodents; yet, none has been successful in achieving primary clinical endpoints in patients (31, 32, 34, 38, 44, 55-57). Pfizer's MYO-029, an anti-myostatin antibody was shown to have poor pharmacological properties, which likely contributed to its clinical failure (58). Acceleron's ACE-031 was discontinued following adverse bleeding events, the result of BMP9 inhibition (41). In other cases, the underlying cause of failure is less clear. For example, multiple companies have taken their molecules into trials with elderly patients (e.g., sarcopenia, older weak fallers). While patients in these trials showed modest increases in muscle mass (~2-3%), there was no corresponding improvement in muscle strength (38, 40, 59). One possibility for this disconnect is that these trials were not long enough to detect improvements in muscle function; additional time may be required for the central nervous system to adapt to larger muscles. Alternatively, the reduced anabolic potential in the elderly (i.e. reduced expression of IGF-1 and testosterone, reduced muscle protein synthesis) may limit the efficacy of myostatin inhibition in this population (60, 61). Collectively, these results caution that even where a modest degree of muscle growth is achieved, it may not necessarily translate to improved muscle function (e.g., strength, force generation), hence motor function, such as the ability to carry out certain motor tasks.

As used herein, the term "myostatin inhibitor" refers to any agent capable of blocking or antagonizing myostatin signaling. Such agents may include small molecule antagonists of myostatin and biologic antagonists of myostatin (e.g., protein fragments and antibodies). In some embodiments, the myostatin inhibitor may be an antibody (including fragments thereof, such as Domain Antibodies (dAbs) as described in, for example, U.S. Pat. Nos. 6,291,158; 6,582,915; 6,593,081; 6,172,197; and 6,696,245), a small molecule inhibitor, an Adnectin, an Affibody, a DARPin, an Anticalin, an Avimer, a Versabody or a gene therapy. Myostatin inhibitors or antagonists known in the art to date include but are not limited to: PF06252616 (Pfizer); Trevogrumab (Regneron); ACE-083 (Acceleron); BMS-986089 (BMS); Follistatin (Nationwide); ACE-031 (Acceleron); Myo-029 (Wyeth); LY2495655 (Eli Lilly); Pinta-745 (Atara); Bimagrumab/BYM338 (Novartis); and anti-latent myostatin antibodies described in PCT/JP2015/006323 (Chugai) or any derivatives (such as affinity-matured or humanized derivatives, or fragments) thereof, and the anti-myostatin antibodies described herein, e.g., SRK-015, or an antigen-binding fragment thereof. Use of myostatin inhibitors encompassed by the present invention also includes antibody mimetics, such as monobodies and single-domain antibodies. Monobodies are synthetic binding proteins that typically employ a fibronectin type III domain (FN3) as a molecular scaffold. Monobodies include Adnectins™ which are based on the 10th fibronectin type III domain One example of Adnectin is BMS-986089.

Preferably, a myostatin inhibitor is selective for myostatin. Many agents described in the literature to block myostatin activities are found to be not selective for myostatin. Many such agents in fact also affect other related growth factors, GDF11 in particular, which shares high sequence homology with myostatin (~90% identity). To reduce potential adverse effects, agents that specifically block myostatin signaling (without affecting other growth factor signaling) are preferred. This may be particularly important for pediatric populations and young adults who are still growing and anabolically active. For example, GDF11 plays an important role during early development. Thus, preserving intact GDF11 signaling in growing individuals may be crucial to avoid perturbation of the normal development process. Similarly, highly selective intervention of myostatin signaling over other biological pathways may be advantageous in situations where long-term therapy is warranted, which in some cases may involve life-long treatment. In this way, any unwanted side effects and toxicities may be minimized or prevented from accumulating over time to cause long-term adverse effects.

Suitable inhibitors of myostatin include biologics, such as antibodies (e.g., SRK-015). These include: i) a class of antibodies or antigen-binding fragments thereof that inhibit the activation step of myostatin from its precursor; ii) a class of antibodies or antigen-binding fragments thereof that neutralize mature myostatin activities; and iii) a class of antibodies or antigen-binding fragments thereof that blocks the interaction of myostatin with its receptor. In some embodiments, the antibodies of (i) above are preferred. Non-limiting examples of such antibodies are disclosed in, for example, PCT/US2015/059468 and PCT/US2016/052014, each of which is incorporated herein by reference in its entirety. In some embodiments, antibodies or antigen-binding portions thereof that are suitable for carrying out the present invention comprise one or more CDR sequences, the variable heavy and light chain sequences, or the heavy chain and light chain sequences selected from those described in Table 1, Table 2, or Table 3, below.

TABLE 1

Anti-Myostatin Antibody CDR sequences

| Antibody | CDRH1 (SEQ ID NOs: 1-3) | CDRH2 (SEQ ID NOs: 4-9) | CDRH3 (SEQ ID NOs: 10-11) | CDRL1 (SEQ ID NOs: 12-17) | CDRL2 (SEQ ID NOs: 18-21) | CDRL3 (SEQ ID NOs: 22-23) |
|---|---|---|---|---|---|---|
| Kabat: | SSYGMH (SEQ ID NO: 1) | VISYDGSNKYYADSVKG (SEQ ID NO: 4) | DLLVRFLEWSHYYGMDV (SEQ ID NO: 10) | SGSSSNIGSNTVH (SEQ ID NO: 12) | SDNQRPS (SEQ ID NO: 18) | AAWDDSLNGV (SEQ ID NO: 22) |
| IMGT: | GFTFSSYGMH (SEQ ID NO: 2) | ISYDGSN (SEQ ID NO: 5) | | SSNIGSNT (SEQ ID NO: 13) | SDN (SEQ ID NO: 19) | |
| Kabat: | SSYGMH (SEQ ID NO: 1) | VISYDGSNKYYADSVKG (SEQ ID NO: 4) | DLLVRFLEWSHYYGMDV (SEQ ID NO: 10) | SGSSSNIGSNTVH (SEQ ID NO: 12) | SDNQRPS (SEQ ID NO: 18) | AAWDDSLNGV (SEQ ID NO: 22) |
| IMGT: | GFTFSSYGMH (SEQ ID NO: 2) | ISYDGSN (SEQ ID NO: 5) | | SSNIGSNT (SEQ ID NO: 13) | SDN (SEQ ID NO: 19) | |
| Kabat: | SSYGMH (SEQ ID NO: 1) | VISYDGSIKYYADSVKG (SEQ ID NO: 6) | DLLVRFLEWSHKYGMDV (SEQ ID NO: 11) | SGSTSNIGSNTVH (SEQ ID NO: 14) | SDDQRPS (SEQ ID NO: 20) | AAWDESLNGV (SEQ ID NO: 23) |
| IMGT: | GFAFSSYGMH (SEQ ID NO: 3) | ISYDGSI (SEQ ID NO: 7) | | TSNIGSNT (SEQ ID NO: 15) | SDD (SEQ ID NO: 21) | |
| Kabat: | SSYGMH (SEQ ID NO: 1) | VISYDGSIKYYADSVKG (SEQ ID NO: 6) | DLLVRFLEWSHKYGMDV (SEQ ID NO: 11) | SGSTSNIGSNTVH (SEQ ID NO: 14) | SDDQRPS (SEQ ID NO: 20) | AAWDESLNGV (SEQ ID NO: 23) |
| IMGT: | GFAFSSYGMH (SEQ ID NO: 3) | ISYDGSI (SEQ ID NO: 7) | | TSNIGSNT (SEQ ID NO: 15) | SDD (SEQ ID NO: 21) | |
| Kabat: | SSYGMH (SEQ ID NO: 1) | VISYDGNNKYYADSVKG (SEQ ID NO: 8) | DLLVRFLEWSHKYGMDV (SEQ ID NO: 11) | SGSSSNIGGNTVH (SEQ ID NO: 16) | SDDQRPS (SEQ ID NO: 20) | AAWDESLNGV (SEQ ID NO: 23) |
| IMGT: | GFAFSSYGMH (SEQ ID NO: 3) | ISYDGNN (SEQ ID NO: 9) | | SSNIGGNT (SEQ ID NO: 17) | SDD (SEQ ID NO: 21) | |

In the above table, the single sequences of CDRH3 and CDRL3 reflect Kabat and IMGT.

TABLE 2

Anti-Myostatin Antibody Sequences

| Description | Amino Acid Sequence (SEQ ID NO) | Nucleic Acid Sequence (SEQ ID NO) |
|---|---|---|
| Heavy chain variable region | QIQLVQSGGGVVQPGRSLRL SCAASGFTFSSYGMHWVRQ APGKGLEWVAVISYDGSNK YYADSVKGRFTISRDNSKNT LYLQMNSLRAEDTAVYYCA RDLLVRFLEWSHYYGMDV WGQGTTVTSS (SEQ ID NO: 24) | CAGATCCAGCTGGTGCAGTCTGGGG GAGGCGTGGTCCAGCCTGGGAGGTC CCTGAGACTCTCCTGTGCAGCGTCTG GATTCACCTTCAGTAGCTATGCCATG CACTGGGTCCGCCAGGCTCCAGGCA AGGGGCTGGAGTGGGTGGCAGTTAT ATCATATGATGGAAGTAATAAATACT ATGCAGACTCCGTGAAGGGCCGATTC ACCATCTCCAGAGACAATTCCAAGA ACACGCTGTATCTGCAAATGAACAGC CTGAGAGCCGAGGACACGGCTGTGT ATTACTGTGCGAGAGATCTCCTGGTG CGATTTTTGGAGTGGTCGCACTACTA |

TABLE 2-continued

Anti-Myostatin Antibody Sequences

| Description | Amino Acid Sequence (SEQ ID NO) | Nucleic Acid Sequence (SEQ ID NO) |
|---|---|---|
| | | CGGTATGGACGTCTGGGGCCAAGGG ACCACGGTCACCGTCTCCTCA (SEQ ID NO: 38) |
| Heavy chain variable region | QVQLVESGGGVVQPGRSLR LSCAASGFTFSSYGMHWVR QAPGKGLEWVAVISYDGSN KYYADSVKGRFTISRDNSKN TLYLQMNSLRAEDTAVYYC ARDLLVRFLEWSHYYGMDV WGQGTTVTVSS (SEQ ID NO: 25) | CAGGTGCAGCTGGTGGAGTCTGGGG GAGGCGTGGTCCAGCCTGGGAGGTC CCTGAGACTCTCCTGTGCAGCGTCTG GATTCACCTTCAGTAGCTATGGCATG CACTGGGTCCGCCAGGCTCCAGGCA AGGGGCTGGAGTGGGTGGCAGTTAT ATCATATGATGGAAGTAATAAATACT ATGCAGACTCCGTGAAGGGCCGATTC ACCATCTCCAGAGACAATTCCAAGA ACACGCTGTATCTGCAAATGAACAGC CTGAGAGCCGAGGACACGGCTGTGT ATTACTGTGCGAGAGATCTCCTGGTG CGATTTTTGGAGTGGTCGCACTACTA CGGTATGGACGTCTGGGGCCAAGGG ACCACGGTCACCGTCTCCTCA (SEQ ID NO: 39) |
| Heavy chain variable region | QIQLVQSGGGVVQPGRSLRL SCAASGFAFSSYGMHWVRQ APGKGLEWVAVISYDGSIKY YADSVKGRFTISRDNSKNTL YLQMNSLRAEDTAVYYCAR DLLVRFLEWSHKYGMDVW GQGTTVTVSS (SEQ ID NO: 26) | CAGATCCAGCTGGTGCAGTCTGGGG GAGGCGTGGTCCAGCCTGGGAGGTC CCTGAGACTCTCCTGTGCAGCGTCTG GATTCGCCTTCAGTAGCTATGGCATG CACTGGGTCCGCCAGGCTCCAGGCA AGGGGCTGGAGTGGGTGGCAGTTAT ATCATATGATGGAAGTATCAAATACT ATGCAGACTCCGTGAAGGGCCGATTC ACCATCTCCAGAGACAATTCCAAGA ACACGCTGTATCTGCAAATGAACAGC CTGAGAGCCGAGGACACGGCTGTGT ATTACTGTGCGAGAGATCTCCTGGTG CGATTTTTGGAGTGGTCGCACAAGTA CGGTATGGACGTCTGGGGCCAAGGG ACCACGGTCACCGTCTCCTCA (SEQ ID NO: 40) |
| Heavy chain variable region | QVQLVESGGGVVQPGRSLR LSCAASGFAFSSYGMHWVR QAPGKGLEWVAVISYDGSIK YYADSVKGRFTISRDNSKNT LYLQMNSLRAEDTAVYYCA RDLLVRFLEWSHKYGMDV WGQGTTVTVSS (SEQ ID NO: 27) | CAGGTGCAGCTGGTGGAGTCTGGGG GAGGCGTGGTCCAGCCTGGGAGGTC CCTGAGACTCTCCTGTGCAGCGTCTG GATTCGCCTTCAGTAGCTATGGCATG CACTGGGTCCGCCAGGCTCCAGGCA AGGGGCTGGAGTGGGTGGCAGTTAT ATCATATGATGGAAGTATCAAATACT ATGCAGACTCCGTGAAGGGCCGATTC ACCATCTCCAGAGACAATTCCAAGA ACACGCTGTATCTGCAAATGAACAGC CTGAGAGCCGAGGACACGGCTGTGT ATTACTGTGCGAGAGATCTCCTGGTG CGATTTTTGGAGTGGTCGCACAAGTA CGGTATGGACGTCTGGGGCCAAGGG ACCACGGTCACCGTCTCCTCA (SEQ ID NO: 41) |
| Heavy chain variable region | QIQLVQSGGGVVQPGRSLRL SCAASGFAFSSYGMHWVRQ APGKGLEWVAVISYDGNNK YYADSVKGRFTISRDNSKNT LYLQMNSLRAEDTAVYYCA RDLLVRFLEWSHKYGMDV WGQGTTVTVSS (SEQ ID NO: 28) | CAGATCCAGCTGGTGCAGTCTGGGG GAGGCGTGGTCCAGCCTGGGAGGTC CCTGAGACTCTCCTGTGCAGCGTCTG GATTCGCCTTCAGTAGCTATGGCATG CACTGGGTCCGCCAGGCTCCAGGCA AGGGGCTGGAGTGGGTGGCAGTTAT ATCATATGATGGAAATAATAAATACT ATGCAGACTCCGTGAAGGGCCGATTC ACCATCTCCAGAGACAATTCCAAGA ACACGCTGTATCTGCAAATGAACAGC CTGAGAGCCGAGGACACGGCTGTGT ATTACTGTGCGAGAGATCTCCTGGTG CGATTTTTGGAGTGGTCGCACAAGTA CGGTATGGACGTCTGGGGCCAAGGG ACCACGGTCACCGTCTCCTCA (SEQ ID NO: 42) |
| Heavy chain variable region | QVQLVESGGGVVQPGRSLR LSCAASGFAFSSYGMHWVR QAPGKGLEWVAVISYDGNN | CAGGTGCAGCTGGTGGAGTCTGGGG GAGGCGTGGTCCAGCCTGGGAGGTC CCTGAGACTCTCCTGTGCAGCGTCTG |

TABLE 2-continued

Anti-Myostatin Antibody Sequences

| Description | Amino Acid Sequence (SEQ ID NO) | Nucleic Acid Sequence (SEQ ID NO) |
|---|---|---|
| | KYYADSVKGRFTISRDNSKN TLYLQMNSLRAEDTAVYYC ARDLLVRFLEWSHKYGMDV WGQGTTVTVSS (SEQ ID NO: 29) | GATTCGCCTTCAGTAGCTATGGCATG CACTGGGTCCGCCAGGCTCCAGGCA AGGGGCTGGAGTGGGTGGCAGTTAT ATCATATGATGGAAATAATAAATACT ATGCAGACTCCGTGAAGGGCCGATTC ACCATCTCCAGAGACAATTCCAAGA ACACGCTGTATCTGCAAATGAACAGC CTGAGAGCCGAGGACACGGCTGTGT ATTACTGTGCGAGAGATCTCCTGGTG CGATTTTTGGAGTGGTCGCACAAGTA CGGTATGGACGTCTGGGGCCAAGGG ACCACGGTCACCGTCTCCTCA (SEQ ID NO: 43) |
| Light chain variable region | QPVLTQPPSASGTPGQRVTIS CSGSSSNIGSNTVHWYQQLP GTAPKLLIYSDNQRPSGVPD RFSGSKSGTSASLVISGLQSD DEADYYCAAWDDSLNGVFG GGTKLTVL (SEQ ID NO: 30) | CAGCCTGTGCTGACTCAGCCACCCTC AGCGTCTGGGACCCCCGGGCAGAGG GTCACCATCTCTTGTTCTGGAAGCAG CTCCAACATCGGAAGTAATACTGTCC ACTGGTACCAGCAACTCCCAGGAAC GGCCCCCAAACTCCTCATCTATAGTG ATAATCAGCGCCCCTCAGGGGTCCCT GACCGATTCTCTGGCTCCAAGTCTGG CACCTCAGCCTCCCTGGTCATCAGTG GGCTCCAGTCTGACGATGAGGCTGAT TATTACTGTGCAGCATGGGATGACAG CCTGAATGGGGTGTTCGGCGGAGGG ACCAAGCTGACCGTCCTA (SEQ ID NO: 44) |
| Light chain variable region | QSVLTQPPSASGTPGQRVTIS CSGSSSNIGSNTVHWYQQLP GTAPKLLIYSDNQRPSGVPD RFSGSKSGTSASLAISGLQSE DEADYYCAAWDDSLNGVFG GGTKLTVL (SEQ ID NO: 31) | CAGTCTGTGCTGACTCAGCCACCCTC AGCGTCTGGGACCCCCGGGCAGAGG GTCACCATCTCTTGTTCTGGAAGCAG CTCCAACATCGGAAGTAATACTGTCC ACTGGTACCAGCAACTCCCAGGAAC GGCCCCCAAACTCCTCATCTATAGTG ATAATCAGCGCCCCTCAGGGGTCCCT GACCGATTCTCTGGCTCCAAGTCTGG CACCTCAGCCTCCCTGGCCATCAGTG GGCTCCAGTCTGAGGATGAGGCTGAT TATTACTGTGCAGCATGGGATGACAG CCTGAATGGGGTGTTCGGCGGAGGG ACCAAGCTGACCGTCCTA (SEQ ID NO: 45) |
| Light chain variable region | QPVLTQPPSASGTPGQRVTIS CSGSTSNIGSNTVHWYQQLP GTAPKLLIYSDDQRPSGVPD RFSGSKSGTSASLVISGLQSD DEADYYCAAWDESLNGVFG GGTKLTVL (SEQ ID NO: 32) | CAGCCTGTGCTGACTCAGCCACCCTC AGCGTCTGGGACCCCCGGGCAGAGG GTCACCATCTCTTGTTCTGGAAGCAC CTCCAACATCGGAAGTAATACTGTCC ACTGGTACCAGCAACTCCCAGGAAC GGCCCCCAAACTCCTCATCTATAGTG ATGATCAGCGCCCCTCAGGGGTCCCT GACCGATTCTCTGGCTCCAAGTCTGG CACCTCAGCCTCCCTGGTCATCAGTG GGCTCCAGTCTGACGATGAGGCTGAT TATTACTGTGCAGCATGGGATGAGAG CCTGAATGGGGTGTTCGGCGGAGGG ACCAAGCTGACCGTCCTA (SEQ ID NO: 46) |
| Light chain variable region | QSVLTQPPSASGTPGQRVTIS CSGSTSNIGSNTVHWYQQLP GTAPKLLIYSDDQRPSGVPD RFSGSKSGTSASLAISGLQSE DEADYYCAAWDESLNGVFG GGTKLTVL (SEQ ID NO: 33) | CAGTCTGTGCTGACTCAGCCACCCTC AGCGTCTGGGACCCCCGGGCAGAGG GTCACCATCTCTTGTTCTGGAAGCAC CTCCAACATCGGAAGTAATACTGTCC ACTGGTACCAGCAACTCCCAGGAAC GGCCCCCAAACTCCTCATCTATAGTG ATGATCAGCGCCCCTCAGGGGTCCCT GACCGATTCTCTGGCTCCAAGTCTGG CACCTCAGCCTCCCTGGCCATCAGTG GGCTCCAGTCTGAGGATGAGGCTGAT TATTACTGTGCAGCATGGGATGAGAG CCTGAATGGGGTGTTCGGCGGAGGG ACCAAGCTGACCGTCCTA (SEQ ID NO: 47) |

TABLE 2-continued

Anti-Myostatin Antibody Sequences

| Description | Amino Acid Sequence (SEQ ID NO) | Nucleic Acid Sequence (SEQ ID NO) |
| --- | --- | --- |
| Light chain variable region | QPVLTQPPSASGTPGQRVTIS CSGSSSNIGGNTVHWYQQLP GTAPKLLIYSDDQRPSGVPD RFSGSKSGTSASLVISGLQSD DEADYYCAAWDESLNGVFG GGTKLTVL (SEQ ID NO: 34) | CAGCCTGTGCTGACTCAGCCACCCTC AGCGTCTGGGACCCCCGGGCAGAGG GTCACCATCTCTTGTTCTGGAAGCAG CTCCAACATCGGAGGAAATACTGTCC ACTGGTACCAGCAACTCCCAGGAAC GGCCCCCAAACTCCTCATCTATAGTG ATGATCAGCGCCCCTCAGGGGTCCCT GACCGATTCTCTGGCTCCAAGTCTGG CACCTCAGCCTCCCTGGTCATCAGTG GGCTCCAGTCTGACGATGAGGCTGAT TATTACTGTGCAGCATGGGATGAGAG CCTGAATGGGGTGTTCGGCGGAGGG ACCAAGCTGACCGTCCTA (SEQ ID NO: 48) |
| Light chain variable region | QSVLTQPPSASGTPGQRVTIS CSGSSSNIGGNTVHWYQQLP GTAPKLLIYSDDQRPSGVPD RFSGSKSGTSASLAISGLQSE DEADYYCAAWDESLNGVFG GGTKLTVL (SEQ ID NO: 35) | CAGTCTGTGCTGACTCAGCCACCCTC AGCGTCTGGGACCCCCGGGCAGAGG GTCACCATCTCTTGTTCTGGAAGCAG CTCCAACATCGGAGGAAATACTGTCC ACTGGTACCAGCAACTCCCAGGAAC GGCCCCCAAACTCCTCATCTATAGTG ATGATCAGCGCCCCTCAGGGGTCCCT GACCGATTCTCTGGCTCCAAGTCTGG CACCTCAGCCTCCCTGGCCATCAGTG GGCTCCAGTCTGAGGATGAGGCTGAT TATTACTGTGCAGCATGGGATGAGAG CCTGAATGGGGTGTTCGGCGGAGGG ACCAAGCTGACCGTCCTA (SEQ ID NO: 49) |
| Heavy Chain | QVQLVESGGGVVQPGRSLR LSCAASGFTFSSYGMHWVR QAPGKGLEWVAVISYDGSN KYYADSVKGRFTISRDNSKN TLYLQMNSLRAEDTAVYYC ARDLLVRFLEWSHYYGMDV WGQGTTVTVSSASTKGPSVF PLAPCSRSTSESTAALGCLVK DYFPEPVTVSWNSGALTSGV HTFPAVLQSSGLYSLSSVVT VPSSSLGTKTYTCNVDHKPS NTKVDKRVESKYGPPCPPCP APEFLGGPSVFLFPPKPKDTL MISRTPEVTCVVVDVSQEDP EVQFNWYVDGVEVHNAKT KPREEQFNSTYRVVSVLTVL HQDWLNGKEYKCKVSNKG LPSSIEKTISKAKGQPREPQV YTLPPSQEEMTKNQVSLTCL VKGFYPSDIAVEWESNGQPE NNYKTTPPVLDSDGSFFLYS RLTVDKSRWQEGNVFSCSV MHEALHNHYTQKSLSLSLG (SEQ ID NO: 50) | |
| Light Chain | QSVLTQPPSASGTPGQRVTIS CSGSSSNIGSNTVHWYQQLP GTAPKLLIYSDNQRPSGVPD RFSGSKSGTSASLAISGLQSE DEADYYCAAWDDSLNGVFG GGTKLTVLGQPKAAPSVTLF PPSSEELQANKATLVCLISDF YPGAVTVAWKADSSPVKAG VETTTPSKQSNNKYAASSYL SLTPEQWKSHRSYSCQVTHE GSTVEKTVAPTECS (SEQ ID NO: 51) | |

TABLE 3

Anti-Myostatin Antibody Sequences

| CDR-H3 | CDR-L3 | VH | VL | scFV | SEQ ID NOs: from left to right |
|---|---|---|---|---|---|
| ESLIRF LEDPQ QGGM DV | NSWTR SNNYI | QVQLQQSG AEVKKPGA SVKVSCKA SGYTFTSY YMHWVRQ APGQGLE WMGIINPS GGSTSYAQ KFQGRVT MTRDTSTS TVYMELSS LRSEDTAV YYCARESL IRFLEDPQQ GGMDVWG QGTTVTVS S | QSALTQPAS VSGSPGQSL TISCTGTSS DIGGYNYV SWYQQHPG KAPKLIIYD VTDRPSGVS GRFSGSKSG NTASLTISG LQTEDEAE YFCNSWTR SNNYIFGGG TKLTVLGQ PKAAPSVTL | QVQLQQSGAEVKKPGAS VKVSCKASGYTFTSYY MHWVRQAPGQGLEWM GIINPSGGSTSYAQKFQG RVTMTRDTSTSTVYMEL SSLRSEDTAVYYCARES LIRFLEDPQQGGMDVW GQGTTVTVSSGSASAPT LGGGGSGGGGSAAAQS ALTQPASVSGSPGQSLTI SCTGTSSDIGGYNYVSW YQQHPGKAPKLIIYDVT DRPSGVSGRFSGSKSGN TASLTISGLQTEDEAEYF CNSWTRSNNYIFGGGTK LTVLGQPKAAPSVTLFPP SS | 71-75 |
| DRYSS SWGG GFDY | QSYDA SSLW V | EVQLVQSG GGVVQSG RSLRLSCV ASGFSFSN YGMHWVR QAPGKGLE WLAFIWY DGSNKWY ADSVKGRF TISRDNSK NALYLQM NSLRAEDT AVYYCAR DRYSSSWG GGFDYWG QGTVLTVS S | NFMLTQPHS VSESPGRTV TIPCSGRGG SIASDSVQW YQQRPGSA PTTIIYEDN QRPSGVPD RFSGSVDSS SNSASLTIS GLRTEDEA DYYCQSYD ASSLWVFG GKTKLTVL GQPKAAPS VTL | EVQLVQSGGGVVQSGRS LRLSCVASGFSFSNYGM HWVRQAPGKGLEWLAF IWYDGSNKWYADSVKG RFTISRDNSKNALYLQM NSLRAEDTAVYYCARD RYSSSWGGGFDYWGQG TVLTVSSGSASAPTLGG GGSGGGGSAAANFMLT QPHSVSESPGRTVTIPCS GRGGSIASDSVQWYQQ RPGSAPTTIIYEDNQRPS GVPDRFSGSVDSSSNSAS LTISGLRTEDEADYYCQ SYDASSLWVFGGKTKLT VLGQPKAAPSVTLFPPSS KASGA | 76-80 |
| DRHSL GDFD Y | QAWD STTVV | QLQLQQSG GGLVKPGG SLRLSCAA SGFTFSSYS MNWVRQA PGKGLEW VSSISSSSS YIYYADSV KGRFTISR DNAKNSLY LQMNSLRA EDTAVYYC VRDRHSLG DFDYWGQ GTLVTVSS GS | SSELTQPSVS VSPGQTATI TCSGDKLG DKYASWYQ QKPGQSPV LVIY QDTKRPSGI PARFSGSNS GNTATLTIS GTQAMDEA AYYCQAW DSTTVVF GGGTKLTV LGQPKAAP SVTLFPPSS | QLQLQQSGGGLVKPGGS LRLSCAASGFTFSSYSM NWVRQAPGKGLEWVSS ISSSSSYIYYADSVKGRF TISRDNAKNSLYLQMNS LRAEDTAVYYCVRDRH SLGDFDYWGQGTLVTV SSGSASAPTLGGGGSGG GGSAAAASSELTQPPSVS VSPGQTATITCSGDKLG DKYASWYQQKPGQSPV LVIYQDTKRPSGIPARF | 81-85 |
| HGLM DDSS GYYL SNAF DI | ATWD DSLTG VV | QVQLVQSG AEVKKPGS SVKVSCKA SGGTFSSY AISWVRQA PGQGLEW MGGIIPIFG TANYAQKF QGRVTITA DESTSTAY MELSSLRS EDTAVYYC ANHGLMD DSSGYYLS NAFDIWGQ GTMVTVSS GS | QPVLTQPPS ASGTPGQR VTISCSGSSS NIGSNTVE WYQQLPGT APKLLIHSN NQRPSGVP DRFSGSRSG TSASLAISG LQSEDEAD YFCATWDD SLTGVVFG GGTTLTVL GQPKAAPS VTLFPPSS | QVQLVQSGAEVKKPGSS VKVSCKASGGTFSSYAIS WVRQAPGQGLEWMGGI IPIFGTANYAQKFQGRVT ITADESTSTAYMELSSLR SEDTAVYYCANHGLMD DSSGYYLSNAFDIWGQG TMVTVSSGSASAPTLGG GGSGGGGSAAAQPVLT QPPSASGTPGQRVTISCS GSSSNIGSNTVEWYQQL PGTAPKLLIHSNNQRPSG VPDRFSGSRSGTSASLAI SGLQSEDEADYFCATW DDSLTGVVFGGGTTLTV LGQPKAAPSVTLFPPSS | 86-90 |
| VGTAA AGDA FDI | AAWD DSLSG WV | QVQLVQSG GGLIQPGG SLRLSCAA | QPVLTQPPS ASGTPGQR VTISCFGSSS | QVQLVQSGGGLIQPGGSL RLSCAASGFTVSSYSMN WVRQAPGKGLEWVSYI | 91-95 |

TABLE 3-continued

Anti-Myostatin Antibody Sequences

| CDR-H3 | CDR-L3 | VH | VL | scFV | SEQ ID NOs: from left to right |
|---|---|---|---|---|---|
| | | SGFTVSSY<br>SMNWVRQ<br>APGKGLE<br>WVSYISSS<br>GSTIYYAD<br>SVKGRFTIS<br>RDNAKNSL<br>YLQMNSLR<br>AEDTALYY<br>CAKVGTA<br>AAGDAFDI<br>WGQGTMV<br>TVSSGS | NIGSNYVY<br>WYQQLPGT<br>APKLLIYRN<br>NQRPSGVP<br>DRFSGSKSG<br>TSASLAISG<br>LRSEDEAD<br>YYCAAWD<br>DSLSGWVF<br>GGGTKLTV<br>LGQPKAAP<br>SVTLFPPSS | SSSGSTIYYADSVKGRFT<br>ISRDNAKNSLYLQMNSL<br>RAEDTALYYCAKVGTA<br>AAGDAFDIWGQGTMVT<br>VSSGSASAPTLGGGGSG<br>GGGSAAAQPVLTQPPSA<br>SGTPGQRVTISCFGSSSNI<br>GSNYVYWYQQLPGTAP<br>KLLIYRNNQRPSGVPDR<br>FSGSKSGTSASLAISGLR<br>SEDEADYYCAAWDDSL<br>SGWVFGGGTKLTVLGQ<br>PKAAPSVTLFPPSS | |
| VGFYD<br>YVWG<br>SYPY<br>DAFDI | QQYGT<br>SPLT | QIQLVQSGA<br>EVKKPGAS<br>VKVSCKAS<br>GYTFTSYG<br>ISWVRQAP<br>GQGLEWM<br>GWISAYNG<br>NTNYAQK<br>LQGRVTM<br>TTDTSTST<br>AYMELSSL<br>RSEDTAVY<br>YCARVGFY<br>DYVWGSY<br>PYDAFDIW<br>GQGTMVT<br>VSS | EIVMTQSPG<br>TLSLSPGER<br>ATLSCRASQ<br>SVSSNYLA<br>WYQQKPGQ<br>APRLLIYDA<br>SNRATGIPA<br>RFSGSGSGT<br>DFTLTISSLE<br>PEDFALYY<br>CQQYGTSP<br>LTFGGGTK<br>LEIK | QIQLVQSGAEVKKPGAS<br>VKVSCKASGYTFTSYGI<br>SWVRQAPGQGLEWMG<br>WISAYNGNTNYAQKLQ<br>GRVTMTTDTSTSTAYME<br>LSSLRSEDTAVYYCARV<br>GFYDYVWGSYPYDAFDI<br>WGQGTMVTVSSGSASA<br>PTLGGGGSGGGSAAAE<br>IVMTQSPGTLSLSPGERA<br>TLSCRASQSVSSNYLAW<br>YQQKPGQAPRLLIYDAS<br>NRATGIPARFSGSGSGTD<br>FTLTISSLEPEDFALYYC<br>QQYGTSPLTFGGGTKLEI<br>KRTVAAPSVF | 96-100 |
| DTSNG<br>GYSSS<br>SFDY | SSYTSS<br>STLV | EVQLVQSG<br>GGLVQPGR<br>SLRLSCAA<br>SGFTFDDY<br>AMHWVRQ<br>APGKGLE<br>WVSGISWN<br>SGSIGYAD<br>SVKGRFTIS<br>RDNAKNSL<br>YLQMNSLR<br>AEDTALYY<br>CAKDTSNG<br>GYSSSSFD<br>YWGQGTL<br>VTVSS | QSALTQPAS<br>VSGSPGQSI<br>TISCTGTSS<br>DVGGYNYV<br>SWYQQHPG<br>TAPKLMIY<br>DVSYRPSG<br>VSNRFSGSK<br>SGNTASLTI<br>SGLQAEDE<br>ADYYCSSY<br>TSSSTLVFG<br>TGTKVTVL | EVQLVQSGGGLVQPGRS<br>LRLSCAASGFTFDDYAM<br>HWVRQAPGKGLEWVSG<br>ISWNSGSIGYADSVKGR<br>FTISRDNAKNSLYLQMN<br>SLRAEDTALYYCAKDTS<br>NGGYSSSSFDYWGQGTL<br>VTVSSGSASAPTLGGGG<br>SGGGGSAAAQSALTQPA<br>SVSGSPGQSITISCTGTSS<br>DVGGYNYVSWYQQHPG<br>TAPKLMIYDVSYRPSGV<br>SNRFSGSKSGNTASLTIS<br>GLQAEDEADYYCSSYTS<br>SSTLVFGTGTKVTVLGQ<br>PKANPTVTLFPPSS | 101-105 |
| LVYGG<br>YDEP<br>GYYF<br>DY | AAWD<br>DSLN<br>GWV | EVQLLESRA<br>EVKKPGES<br>LKISCKGS<br>GYSFTSYW<br>IGWVRQM<br>PGKGPEW<br>MGIIYPGD<br>SDTRYSPSF<br>QGQVTISA<br>DKSISTAY<br>LQWSSLKA<br>SDTAMYY<br>CARLVYG<br>GYDEPGYY<br>FDYWGQG<br>TLVTVSS | QSVLTQPPS<br>ASGTPGQR<br>VTISCSGSSS<br>NIRSNTVN<br>WYQQLPGT<br>APKLLIYSN<br>NQRPSGVP<br>DRFSGSKSG<br>TSASLAISG<br>LQSEDEAD<br>YYCAAWD<br>DSLNGWVF<br>GGGTKLTV<br>L | EVQLLESRAEVKKPGESL<br>KISCKGSGYSFTSYWIG<br>WVRQMPGKGPEWMGII<br>YPGDSDTRYSPSFQGQV<br>TISADKSISTAYLQWSSL<br>KASDTAMYYCARLVYG<br>GYDEPGYYFDYWGQGT<br>LVTVSSGSASAPTLGGG<br>GSGGGGSAAAQSVLTQP<br>PSASGTPGQRVTISCSGS<br>SSNIRSNTVNWYQQLPG<br>TAPKLLIYSNNQRPSGV<br>DRFSGSKSGTSASLAISG<br>LQSEDEADYYCAAWDD<br>SLNGWVFGGGTKLTVL<br>GQPKAAPSVTLFPPSSKA<br>SGA | 106-110 |
| VDGLE<br>YSSG<br>HNFD<br>Y | SSYAG<br>SYTW<br>V | EVQLVQSG<br>GGLVQPGR<br>SLRLSCAA<br>SGFTFDDY<br>AMHWVRQ<br>APGKGLE<br>WVSGISWN | QSALTQPPS<br>VSGSPGQSV<br>TISCTGSSS<br>DVGYYDHV<br>SWYQHHPG<br>RAPKVIIYD<br>VTKRPSGVP | EVQLVQSGGGLVQPGRS<br>LRLSCAASGFTFDDYAM<br>HWVRQAPGKGLEWVSG<br>ISWNSGSIGYADSVKGR<br>FTISRDNSKNTLYLQMN<br>SLRAEDTAVYYCAKVD<br>GLEYSSGHNFDYWGQG | 111-115 |

TABLE 3-continued

Anti-Myostatin Antibody Sequences

| CDR-H3 | CDR-L3 | VH | VL | scFV | SEQ ID NOs: from left to right |
|---|---|---|---|---|---|
| | | SGSIGYAD SVKGRFTIS RDNSKNTL YLQMNSLR AEDTAVY YCAKVDG LEYSSGHN FDYWGQG TLVTVSS | DRFSGSKSG NTASLTISG LQAEDEAD YYCSSYAG SYTWVFGG GTELTVL | TLVTVSSGSASAPTLGG GGSGGGGSAAAQSALT QPPSVSGSPGQSVTISCT GSSSDVGYYDHVSWYQ HHPGRAPKVIIYDVTKR PSGVPDRFSGSKSGNTA SLTISGLQAEDEADYYC SSYAGSYTWVFGGGTEL TVLGQPKAAPSVTLFPPS S | |

In one embodiment, the antibody, or antigen binding fragment thereof, comprises a heavy chain variable domain comprising a complementarity determining region 3 (CDRH3) comprising a sequence as set forth in any one of SEQ ID NOs:10-11. In one embodiment, the antibody, or antigen binding fragment thereof, comprises a light chain variable domain comprising a complementarity determining region 3 (CDRL3) comprising a sequence as set forth in any one of SEQ ID NO: 22-23. In one embodiment, the antibody, or antigen binding fragment thereof, comprises six complementarity determining regions (CDRs): CDRH1, CDRH2, CDRH3, CDRL1, CDRL2, and CDRL3, wherein CDRH1 comprises a sequence as set forth in any one of SEQ ID NOs: 1-3, CDRH2 comprises a sequence as set forth in any one of SEQ ID NOs: 4-9, CDRH3 comprises a sequence as set forth in any one of SEQ ID NOs: 10-11, CDRL1 comprises a sequence as set forth in any one of SEQ ID NOs: 12-17, CDRL2 comprises a sequence as set forth in any one of SEQ ID NOs: 18-21, and CDRL3 comprises a sequence as set forth in any one of SEQ ID NOs: 22-23.

In one embodiment, CDRH1 comprises a sequence as set forth in SEQ ID NO: 1 or 2, CDRH2 comprises a sequence as set forth in SEQ ID NO: 4 or 5, CDRH3 comprises a sequence as set forth in SEQ ID NO: 10, CDRL1 comprises a sequence as set forth in SEQ ID NO: 12 or 13, CDRL2 comprises a sequence as set forth in SEQ ID NO: 18 or 19, and CDRL3 comprises a sequence as set forth in SEQ ID NO: 22.

In one embodiment, CDRH1 comprises a sequence as set forth in SEQ ID NO: 1 or 3, CDRH2 comprises a sequence as set forth in SEQ ID NO: 6 or 7, CDRH3 comprises a sequence as set forth in SEQ ID NO: 11, CDRL1 comprises a sequence as set forth in SEQ ID NO: 14 or 15, CDRL2 comprises a sequence as set forth in SEQ ID NO: 20 or 21, and CDRL3 comprises a sequence as set forth in SEQ ID NO: 23.

In one embodiment, CDRH1 comprises a sequence as set forth in SEQ ID NO: 1 or 3, CDRH2 comprises a sequence as set forth in SEQ ID NO: 8 or 9, CDRH3 comprises a sequence as set forth in SEQ ID NO: 11, CDRL1 comprises a sequence as set forth in SEQ ID NO: 16 or 17, CDRL2 comprises a sequence as set forth in SEQ ID NO: 20 or 21, and CDRL3 comprises a sequence as set forth in SEQ ID NO: 23.

In preferred embodiments, suitable monoclonal antibody for use in the present invention is SRK-015. SRK-015 binds the "arm" region within the prodomain of the pro/latent myostatin complex and inhibits release of mature growth factor (i.e., GDF-8) from the latent/inactive complex.

The arm region of myostatin is provided herein as SEQ ID NO: 116 (RELIDQYDVQRDDSSDGSLEDDDYHAT-TETIITMPTESDFLMQVDGKPKCCFFKFSSKIQYN KVVKAQLWIYLRPVETPTTVFVQILR-LIKPMKDGTRYTGIRSLKLDMNPGTGIWQSIDVKTVL QNWLKQPESNLGIEIKALDENGHDLAVTFPGPGEDG-LNPFLEVKVTDTPKRSRR). Other domains of myostatin are well known to those of ordinary skill in the art and are listed, for example, at least in Table 2 of WO16/073879, published on May 12, 2016, the entire contents of which are expressly incorporated herein by reference.

Binding of SRK-015 is specific to pro/latent myostatin and therefore SRK-015 does not bind mature GDF-8 or GDF-11 (or any other members of the TGFβ superfamily of growth factors), thereby enabling selective targeting of myostatin signaling, without affecting other biological pathways. In addition to this binding specificity, SRK-015 has demonstrated favorable pharmacokinetic (PK) and pharmacodynamic (PD) properties (see Examples 8 and 9) in both mice and non-human primates. In some embodiments, suitable dosage of SRK-015 for administration in human patients for the treatment of SMA ranges between 1 and 30 mg/kg, e.g., 1-5 mg/kg, 3-5 mg/kg, 3-10 mg/kg, 5-10 mg/kg, 5-15 mg/kg, 5-20 mg/kg, 10-20 mg/kg, etc. In some embodiments, the patient is administered SRK-015 once a week, once every two weeks, once every three weeks, once a month, once every six weeks, etc.

Combination Therapies for Treating Spinal Muscular Atrophy

Based on the recognition of the contribution of nerve input for muscle function, it was surprisingly discovered that, in the presence of a corrector designed to promote or improve motor neuron function, the target muscle may produce greater responsiveness to myostatin inhibition, leading to improved motor function. In addition, most severe forms of SMA have an early onset, typically in very young children, which is a population generally with robust anabolic capacity suitable for myostatin intervention. Moreover, SMA patients have difficulties completing simple motor activities and tasks, which often involve the function of fast-twitch fibers. Taken together, SMA is a clinical indication which will benefit from myostatin inhibition, with the background of an SMN corrector.

Thus, the invention provides combination therapies for the treatment of neuromuscular disorders, such as SMA, which achieve improved clinical benefits in patients as compared to a monotherapy of each agent alone. Specifically, targeting the affected muscles with a specific inhibitor of myostatin signaling aimed to enhance muscle function, in conjunction with a corrector aimed to improve motor neuron function in patients, produces a beneficial clinical outcome relative to the latter alone. Such effects may be supplemental, additive or synergistic as compared to a monotherapy. A combination therapy that produces supplemental effects means that the totality of clinical benefits produced by the combination therapy is greater than those of a monotherapy (e.g., either a neuronal therapy alone or myostatin inhibition therapy alone). A combination therapy that produces additive effects means that the clinical benefits of the agents in combination reflect a sum of the monotherapies. A combination therapy that produces synergistic effects means that the overall benefits achieved in combination are greater than the additive effects of each agent. Moreover, in some embodiments, due to the additive or synergistic effects of a combination therapy, less frequent dosing of one or more of the therapies and/or lower doses of one or more therapies, as compared to administration of the monotherapy alone, may be used. In other embodiments, due to lower dosages and/or less frequent dosing of one or more of the therapies of a combination therapy may result in less toxicity due to fewer side effects from one or more of the therapies. Accordingly, in some embodiments, an effective amount of an agent (such as an SMN corrector) used as a component of a combination therapy to treat a disease (such as SMA) in a subject is less than an effective amount of the same agent used as a monotherapy.

Accordingly, one aspect of the invention provides use of a myostatin inhibitor for the treatment of SMA, particularly for patients who also receive a therapy to address the motor neuron defect, such as an SMN corrector. The invention therefore encompasses methods for treating spinal muscular atrophy (SMA) in a subject who is treated with an SMN corrector, comprising administration of myostatin inhibitor.

In some embodiments, a myostatin inhibitor includes an antibody or antigen-binding fragment thereof that binds mature myostatin, a pro-form of myostatin (e.g., pro- and/or latent myostatin), or myostatin receptor in an amount effective to treat SMA. In some embodiments, suitable antibodies bind mature myostatin but also bind GDF11. In some embodiments, suitable antibodies selectively bind mature myostatin but not GDF11. In some embodiments, suitable antibodies bind mature myostatin and latent myostatin, but not pro-myostatin. In some embodiments, suitable antibodies bind pro- and latent myostatin, but not mature myostatin. In some embodiments, such antibodies inhibit the step of myostatin activation by stabilizing the proMyostatin complex. In some embodiments, such antibodies inhibit the step of myostatin activation by interfering with one or more steps of proteolysis. For example, in some embodiments, such antibodies inhibit protease-dependent cleavage of the myostatin prodomain. In some embodiments, the protease is a furin or furin-like protease, or tolloid or tolloid-like protease. In some embodiments, such antibodies may be pH-sensitive in that the antibody binds its antigen at a neutral pH and dissociates at an acidic pH.

According to the invention, myostatin inhibitors may be administered to SMA patients who are either responders, poor responders, or non-responders of an SMN corrector therapy. For the poor responders or non-responders, concurrent inhibition of myostatin signaling may improve neuromuscular signaling due in part to enhanced muscle function, thereby rendering the innervating motor neurons of non-responders more responsive to the SMN corrector. Without wishing to be bound by particular theory, it is contemplated that enhancement of the muscle component may affect the neuronal component by positive feedback, and vice versa, due to the bidirectional nature of neuromuscular signaling.

Although SMN corrector poor responders and/or non-responders may nevertheless benefit from myostatin inhibition, a more preferred patient population includes those who are responders of an SMN corrector. It is contemplated that motor function in these individuals may be further improved by myostatin inhibition therapy used in combination with SMN corrector therapy.

"Combination therapy" of the present invention is intended to mean that pharmacological effects of one drug (such as an SMN corrector) overlaps in vivo with pharmacological effects of another drug (such as a myostatin inhibitor). Thus, the two drugs need not be administered as a single formulation, nor do they have to be administered concurrently, nor via the same route. Depending on the PK/PD of each drug, for example, it is contemplated that the patient receives the SMN corrector and the myostatin inhibitor generally within six months of one another for best results.

As discussed above, suitable "SMN correctors" include splice modifiers, SMN gene replacement or gene therapy; SMN transcription enhancers; SMN protein translation enhancers; and SMN protein stabilizers. In some embodiments, such SMN correctors may be small molecule agents, biologics, or nucleic acids. In some embodiments, the SMN corrector is a small molecule splice modifier of Smn2. In some embodiments, the SMN corrector is an antisense RNA splice modifier of Smn2. In some embodiments, the gene therapy comprises introduction of one or more transgenes into the patient. In some embodiments, gene transfer is achieved by the use of a suitable vector, such as viral vectors and lipid-based carriers. For viral-vector-mediated gene delivery, the gene therapy may involve the use of a particular serotype for an initial treatment, followed by a different serotype for the subsequent treatment, in order to minimize adverse immune responses in the subject. In some embodiments, the gene therapy involves targeted genome editing, such as the CRISPR/Cas9 technology or variant thereof. Non-limiting examples of SMN correctors to be used for in combination with a myostatin inhibitor according to the present disclosure include but are not limited to: Nusinersen (Biogen); AVXS-101 (AveXis); RG7916 (Roche/PTC/SMAF); RG7800 (Roche/PTC); olesoxime (Roche/Trophos); VY-SMN101 (Voyager/Genzyme); LMI070 (Novartis); SMN Gene Therapy (Genzyme/Sanofi); and Antisense Oligonucleotide (RaNA).

Patient Populations

Combination therapy described herein may be suitable for the treatment of any form of SMA, e.g., SMA type I, type II, type III and type IV in a subject. A "subject," "individual" or "patient" is used interchangeably herein, which refers to a vertebrate, preferably a mammal, more preferably a human Mammals include, but are not limited to, murines, rats, simians, humans, farm animals, sport animals, and pets. In embodiment, a subject is a human subject.

Patient populations who may benefit from the therapies described herein include those with non-ambulatory SMA and those with ambulatory SMA. These include patients suffering from SMA type I, SMA type II, SMA type III, or SMA type IV. In some embodiments, the subject has type II SMA. In some embodiments, the subject has non-ambulatory type III SMA. In some embodiments, the subject has type I SMA. In some embodiments, the subject has ambulatory type III SMA.

In some embodiments of the invention, combination therapy comprising a myostatin inhibition therapy (e.g., a myostatin inhibitor) and a neuronal therapy (e.g., an SMN corrector) is considered for non-ambulatory forms of SMA, such as type I, type II and non-ambulatory type III SMA. In other embodiments, monotherapy of a myostatin inhibitor is considered for ambulatory forms of SMA, such as ambulatory type III and type IV SMA. In addition, myostatin inhibitor monotherapy may be suitable for treating a subject who has been identified as a carrier of an SMN gene mutation by genetic screening. Such genetic screening may be carried out in newborn/infant subjects, as well as in utero (e.g., fetus). Since the severity of the disease heavily depends on the copy number of the Smn2 gene and its expression, the genotypic identification alone may not sufficiently distinguish among very young patients between those who will ultimately develop severe forms of SMA vs. those who will develop milder forms of SMA. For this and other reasons, decision for initiating a neuronal therapy such as an SMN corrector may be deemed premature. Nevertheless, identification of a mutation in Smn1 may warrant an early pharmacological intervention that includes myostatin inhibition, which may provide clinical benefits in the meantime.

In some embodiments, the subject having SMA is between 0-6 months of age. The subject having SMA may be between 6-15 months of age. In another embodiment, the subject having SMA may be <3 years of age. In another embodiment, the subject having SMA may be >3 years of age.

In one embodiment, the subject has been identified to be a carrier of a SMN mutation, e.g., has a mutation in an SMN gene associated with SMA, as is well known to those of ordinary skill in the art, including genetic screening. In one embodiment, the subject has been identified as a carrier of an SMN mutation, e.g., by genetic screening either in utero or as an infant.

As used herein, the subject may suffer from partial damage to neuromuscular function. Neuromuscular function and/or neuromuscular damage are measured using methods commonly known to one of ordinary skill in the art, and described in more detail herein. For example, damage to neuromuscular function may be measured using compound muscle action potential (CMAP), which measures how well the muscle contracts in response to nerve stimulation. Damage to neuromuscular function may also be measured using motor unit number estimation (MUNE), which determines how many motor units form a given nerve.

The methods described herein may further comprise selecting a subject. In some embodiment, the subject suffer from or is at risk of developing a muscle condition or disorder, e.g., SMA. In some embodiment, the subject suffer from or is at risk of developing a disease or disorder associated with impaired neurological signaling. In one embodiment, the subject may be selected based on genetic screening, e.g., identification of a gene mutation, e.g., a gene mutation in SMN, associated with disease, e.g., SMA. In one embodiment, the subject may be selected based on genetic screening within 24 hours of birth. In another embodiment, the subject may be selected based on genetic screening in utero.

Dosage and Administration

To practice the methods disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes.

The terms "administer", "administering" or "administration" include any method of delivery of an antibody or an antigen-binding fragment thereof, e.g., a pharmaceutical composition comprising such an antibody or antigen-binding fragment, or an agent, into a subject's system or to a particular region in or on a subject (systemic and local administration, respectively).

In some embodiments, the subject is administered a myostatin inhibitor and/or a SMN corrector about once a week, once every two weeks, once a month, etc. Typically, suitable dosage of a myostatin inhibitor includes between about 0.1-30 mg/kg. Empirical considerations, such as the half-life, generally will contribute to the determination of the dosage. Such myostatin inhibitor may be administered via intravenous injection/infusion. In some embodiments, such myostatin inhibitor may be administered via subcutaneous injection, e.g., under the skin. In other embodiments, the myostatin inhibitor may be administered intrathecally, e.g., intra spinally. Similarly, a SMN corrector, e.g., splice modifier, may be administered orally, e.g., by mouth.

In one embodiment, the subject has received a SMN corrector prior to the administration of the myostatin inhibitor. In another embodiment, the subject is concurrently receiving a SMN corrector at the same time as the administration of the myostatin inhibitor. In another embodiment, the subject will receive a SMN corrector after administration of the myostatin inhibitor.

In one embodiment, the subject has received a SMN corrector within 6 months of administration of the myostatin inhibitor. In one embodiment, the subject has received a SMN corrector within 3 months of administration of the myostatin inhibitor. In one embodiment, the subject has received a SMN corrector within 6 months, 5 months, 4 months, 3 months, 2 months, or 1 month of administration of the myostatin inhibitor. In one embodiment, the subject has received a SMN corrector within 4 weeks, 3 weeks, 2 weeks, or 1 week of administration of the myostatin inhibitor. In one embodiment, the subject has received a SMN corrector on the same day as administration of the myostatin inhibitor.

In one embodiment, the subject is expected to receive a SMN corrector within 6 months of administration of the myostatin inhibitor. In one embodiment, the subject is expected to receive a SMN corrector within 3 months of administration of the myostatin inhibitor. In one embodiment, the subject is expected to receive a SMN corrector within 6 months, 5 months, 4 months, 3 months, 2 months, or 1 month of administration of the myostatin inhibitor. In one embodiment, the subject is expected to receive a SMN corrector within 4 weeks, 3 weeks, 2 weeks, or 1 week of administration of the myostatin inhibitor.

In one embodiment, the SMN corrector component of the combination therapy is an antisense nucleotide and is administered to the central nervous system of the subject via intrathecal injection. In one embodiment, the antisense nucleotide is administered to the subject every few months, e.g., monthly, every two months, every three months, every four months, every five months, every six months or every 12 months. In another embodiment, an initial treatment may involve more frequent dosing, followed by a less frequent maintenance dose thereafter.

In another embodiment, the SMN corrector component of the combination therapy is a small molecule and is orally administered to the subject. In one embodiment, the small molecule is administered to the subject daily. In another embodiment, the small molecule is administered to the subject weekly, biweekly or monthly.

In one embodiment, the SMN corrector component of the combination therapy is a gene therapy and is administered via intravenous injection. In one embodiment, the SMN corrector is a gene therapy and is administered via intrathecal injection. In one embodiment, an initial treatment may include more frequent dosing, followed by a less frequent maintenance dose thereafter. Less frequent maintenance doses may be preferable in order to avoid improper immune responses to the gene therapy.

In one embodiment, the myostatin inhibitor component of the combination therapy is administered to the subject via intravenous administration. In one embodiment, the myostatin inhibitor portion of the combination therapy is administered to the subject via oral administration. In one embodiment, the myostatin inhibitor component of the combination therapy is administered to the subject via subcutaneous injection. In one embodiment, the myostatin inhibitor is administered daily, weekly, biweekly, or monthly, to the subject. In one embodiment, an initial treatment may involve more frequent dosing, followed by a less frequent maintenance dose thereafter.

An "effective amount" for treating SMA, as used herein, may be an amount to achieve clinical efficacy, including but are not limited to: delay or alleviate muscle atrophy; delay loss of α-motor neurons; prevent or reduce expression of muscle markers; prevent, alleviate or delay intramuscular fat deposits (fatty replacement of muscle tissue); prevent or delay use of ventilator/respirator; delay the time until a patient becomes wheelchair-bound; increase an Expanded Hammersmith Functional Motor Scale score by ≥1 point as compared to untreated control group, or, by ≥1 point from baseline measured prior to corrector treatment; delay progressive decrease of an Expanded Hammersmith Functional Motor Scale over a period of 12 months, 24 months or 36 months; increase a CHOP INTEND score by ≥3 points as compared to untreated control; increase a MFM-32 score by at least 1 point as compared to untreated control; delay transition from ambulatory SMA into non-ambulatory SMA; a reduction in the number of hospitalizations, etc. Each of these measurements are described in more detail below.

As used herein, the term "treating" refers to the application or administration of a composition including one or more active agents to a subject, who has a disease/disorder associated with myopathy, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease/disorder.

Whilst combination therapies that comprise a myostatin inhibitor and a neuronal corrector are generally preferred, in some cases, monotherapy of myostatin inhibitors may be considered. Suitable patient populations considered for such monotherapy include those with milder forms of SMA, such as ambulatory type III SMA and type IV (e.g., adult-onset) SMA. Based on the requirement of criterion (ii) discussed in detail above, patients who have the ability to walk, for example, have retained sufficient neuromuscular function. Therefore, myostatin inhibition may provide benefits to enhance muscle function in these patients even in the absence of concurrent neuronal corrector therapy. Accordingly, monotherapy comprising a myostatin inhibitor for the treatment of mild forms of SMA (e.g., ambulatory SMA) is encompassed by this invention.

In some embodiments, myostatin inhibitor monotherapy for treating patients with ambulatory type III SMA may help delay the disease progression into non-ambulatory SMA. In some embodiments, patients who receive myostatin inhibitor monotherapy may be able to sustain or even improve motor function, as compared to control group (similar diagnosis but without the monotherapy). It should be noted, however, that such patients who respond to myostatin inhibitors in the absence of a neuronal therapy, which may boost the benefits of myostatin inhibition. In some embodiments, myostatin inhibitor monotherapy for treating patients with ambulatory SMA comprises administering to the subject a myostatin inhibitor in an amount effective to produce a clinically meaningful outcome. In these embodiments, clinically meaningful clinical outcome corresponds to an improved Expanded Hammersmith Functional Motor Scale score of at least 1 points (≥1) higher than the untreated control group, or, at least 1 points (≥1) higher than the baseline measured prior to myostatin inhibitor treatment. In some embodiments, meaningful clinical outcome may correspond to an improved Expanded Hammersmith Functional Motor Scale score of at least 1 points (≥1) over the baseline or corrected measured prior to receiving an SMN corrector therapy or the myostatin inhibitor therapy, respectively. In other embodiments, Expanded Hammersmith Functional Motor Scale score of at least 2 points (≥2), at least 3 points (≥3), at least 4 points (≥4), at least 5 points (≥5), at least 6 points (≥6), at least 7 points (≥7), at least 8 points (≥8), at least 9 points (≥9), at least 10 points (≥10), at least 12 points (≥12), at least 15 points (≥15), at least 20 points (≥20), at least 25 points (≥25), at least 30 points (≥30), at least 35 points (≥35), at least 40 points (≥40), at least 45 points (≥45), at least 50 points (≥50), or at least 60 points (≥60), over the baseline or corrected measured prior to receiving an SMN corrector therapy or the myostatin inhibitor therapy, respectively. In some embodiments, meaningful clinical outcome may correspond to an improved Expanded Hammersmith Functional Motor Scale score of at least 1 points (≥1) over the untreated control group. In some embodiments, meaningful clinical outcome may correspond to an improved Expanded Hammersmith Functional Motor Scale score of at least 2 points (≥2), at least 3 points (≥3), at least 4 points (≥4), at least 5 points (≥5), at least 6 points (≥6), at least 7 points (≥7), at least 8 points (≥8), at least 9 points (≥9), or at least 10 points (≥10), at least 12 points (≥12), at least 15 points (≥15), at least 20 points (≥20), at least 25 points (≥25), at least 30 points (≥30), at least 35 points (≥35), at least 40 points (≥40), at least 45 points (≥45), at least 50 points (≥50), or at least 60 points (≥60) over the untreated control group.

In some embodiments, myostatin inhibitor therapy provided herein can help maintain the disease status in a patient population that receives the myostatin inhibitor, as compared to control group that does not. Maintenance of the disease status refers to preventing further deterioration of affected muscle, or delaying or slowing of the rate of disease progression, for example as assessed by changes in motor function over time, in these patients. Therefore, even where no improvement in motor function test scores is shown, the myostatin inhibitor therapy may provide clinical benefits by countering disease progression. Thus, such clinical benefits may present as a longer period of time observed where the patient population treated with the myostatin inhibitor maintains prior test scores, or shows a slower rate of decrease in scores over time, as compared to a control group.

Biological Effects of Myostatin Inhibitors and SMN Correctors

Clinical effects of a myostatin inhibitor, alone or in combination with a SMN corrector, described herein can be monitored and/or evaluated for effectiveness by various means. Exemplary such biologically beneficial effects are provided herein. Beneficial biological effects in a subject can be achieved by administration of myostatin inhibitors in combination with SMN correctors. In some embodiments, the myostatin inhibitor and/or SMN corrector is administered in an amount effective to cause one or more of the biological effects described below.

The ability to assess functional scales that can be reliably measured in SMA patients is crucial in tracking patients' disease progression as well as effects of therapy over time. Whilst muscle function may be assessed by physiological measurements, such as muscle strength and force generation, motor functional scales monitor disease progression in ways that relate to patients' functionality in everyday life and carries more meaning and relevance than a measure that quantitates strength per se. Provided below is a list of several known motor functional assessment tests that can be utilized to evaluate SMA patients, while not intended to be limiting. Other tests include, but are not limited to, gross motor function measure (GMFM), the 6-minute walk test, the 10-meter walk/run test, the time to rise from floor test, the timed up and go test (TUG), and the stair climb test, the methods of which are well known to one of ordinary skill in the art.

Expanded Hammersmith Functional Motor Scale

The disease severity of a patient having SMA, both before treatment, during treatment, and after treatment with a myostatin inhibitor described herein, can be classified using many tests and assays well known to those of ordinary skill in the art. Hammersmith Functional Motor Scale, Expanded (HFMSE) is a validated endpoint for SMA type II and non-ambulatory type III, and is well known to those of ordinary skill in the art. The testing system comprises 33 items (e.g., motor tasks or activities) that assess motor function. Items that are primarily strength-driven motor activities of short duration that require type II fast-twitch fibers include: sitting without hand support for 3 seconds; sitting to lying down; rolling from back to abdomen; push body up for 3 seconds; kneeling to standing position; climbing up/down 4 steps of stairs; jump 12 inches forward, etc.

In some embodiments, the subject has a baseline Expanded Hammersmith Functional Motor Scale score of <66 prior to receiving a corrector or a myostatin inhibitor therapy ("baseline"), e.g., ≤65, ≤60, ≤55, ≤50, ≤40, ≤35, ≤30, ≤25, ≤20, etc. In one embodiment, the subject has a baseline Expanded Hammersmith Functional Motor Scale score of ≤50 prior to receiving a corrector or a myostatin inhibitor. In one embodiment, the subject has a baseline Expanded Hammersmith Functional Motor Scale score of ≤40 prior to receiving a corrector or a myostatin inhibitor. In one embodiment, the subject has a baseline Expanded Hammersmith Functional Motor Scale score of ≤35 prior to receiving a corrector or a myostatin inhibitor. In one embodiment, the subject has a baseline Expanded Hammersmith Functional Motor Scale score of ≤30 prior to receiving a corrector or a myostatin inhibitor. In one embodiment, the subject has a baseline Expanded Hammersmith Functional Motor Scale score of ≤25 prior to receiving a corrector or a myostatin inhibitor. In one embodiment, the subject has a baseline Expanded Hammersmith Functional Motor Scale score of ≤20 prior to receiving a corrector or a myostatin inhibitor.

In some embodiments, the subject has an increased (or "corrected") Expanded Hammersmith Functional Motor Scale score following an SMN corrector therapy. In some embodiments, the subject has improved the score by at least 3 points, at least 4 points, at least 5 points, at least 6 points, at least 7 points, at least 8 points, at least 9 points, at least 10 points, at least 11 points, at least 12 points, at least 13 points, at least 14 points, or at least 15 points, over the baseline, after receiving the SMN corrector. In some embodiments, the subject has an increased Expanded Hammersmith Functional Motor Scale score following an SMN corrector therapy. In some embodiments, the subject has improved the score by at least 3 points, at least 4 points, at least 5 points, at least 6 points, at least 7 points, at least 8 points, at least 9 points, at least 10 points, at least 11 points, at least 12 points, at least 13 points, at least 14 points, or at least 15 points. In some embodiments, upon myostatin inhibitor treatment in addition (i.e., combination therapy), the subject further improves the score by at least 3 points, at least 4 points, at least 5 points, at least 6 points, at least 7 points, at least 8 points, at least 9 points, at least 10 points, either over the baseline measured prior to receiving the SMN corrector treatment or as compared to an untreated control group.

For example, many non-ambulatory SMA patients have the baseline Hammersmith score ranging from 15 to 30 points, out of 66 points total. As a result of an SMN corrector therapy, such patients may improve the score on the average by 4-10 points over the respective baseline. With combination therapy that includes a myostatin inhibitor, such patients may further improve the score. In some embodiments, such patients improve the Expanded Hammersmith Functional Motor Scale score by 1-20 points over the respective baseline. In some embodiments, such patients further improve the Expanded Hammersmith Functional Motor Scale score by at least one point over an already corrected score measured after the SMN corrector therapy.

For SMA patients, clinical significance of even a single point difference in various motor test scoring systems is noteworthy. To put this in perspective, examples are provided below for illustrative purposes, based on the test items from the standard HFMSE system for non-ambulatory SMA patients:

Tasks 1 and 2 of the HFMSE test involve sitting up (without back support) for 3+ seconds. 2 points are given if the patient can sit using no hand support for a count of 3 or more; 1 point for maintaining balance for a count of 3 using one hand as support; and 0 point for requiring both hands to maintain balance. In a real life setting, the difference between the ability to sit without using a hand as support (2 point) vs. requiring to use one hand merely to maintain balance (1 point) is enormous, because in the former case the patient can use both hands for carrying out activities (such as holding an item) while sitting up. Task 3 of the test evaluates whether the patient, while sitting, is able to bring one hand up to touch head above ear level. The ability to perform this seemingly simple task may make a difference in being able to comb one's own hair or putting on a hat without assistance.

Motor Function Measure (MFM)

The Motor Function Measure (MFM) test provides a genetic scale to assess various parameters of motor function in SMA patients of varying degrees of disease severity, including ambulatory and non-ambulatory children and adults aged about 6 and 62 years. There are multiple versions of MFM that are tailored toward different patient populations. For example, MFM32 is suitable for children who are older than 6 years, while MFM20, which is a modified version, has been validated for children under 6 years of age. MFM has been successfully employed in clinical trials to monitor or detect changes in motor function in patients, which reflect deterioration over time (see, for example, clinicaltrials.gov NCT02628743).

In one embodiment, a subject having SMA and being administered a therapy or combination therapy described herein exhibits an increase in MFM score of at least 2-fold, at least 3-fold, at least 4-fold, or at least 5-fold after administration of the therapy or combination therapy.

Upper Limb Module (ULM)

The Upper Limb Module (ULM) test provides assessment of arm function which has been specifically designed as an add-on module. The ULM is intended to capture performance of activities of daily living not typically included in measures of gross motor function. The assessment includes 9 items of activities which can be reliably performed in children and takes ~10 minutes to complete. The ULM has been used in a multicentric setting and in clinical trials.

In one embodiment, a subject having SMA and being administered a therapy or combination therapy described herein exhibits an increase in ULM score of at least 2-fold, at least 3-fold, at least 4-fold, or at least 5-fold after administration of the therapy or combination therapy.

Revised Upper Limb Module

Revised Upper Limb Module (RULM) allows assessment of arm function in patients with SMA which has shown good validity and reliability, making it suitable for use in clinical research. The RULM included 20 items of activities that could be completed successfully by children as young as 30 months. These items include tasks such as bringing hands from lap to table, picking up small items, pushing buttons, tearing paper, opening a Ziploc container, bringing hands above shoulders, and lifting items of different weight to different heights. Outcome measures are tests used by researchers to assess whether a certain treatment under trial is having any effects on the patient. Using the right outcome measure is vital to make sure a trial can prove if a treatment works. According to SMA News Today, RULM effectively captured the progressive muscle weakness in the weak end of the spectrum. Six-Minute Walk Test Six Minute Walk Test (6MWT) is reported to be a reliable and valid functional assessment in patients with SMA, which is able to capture a fatigue element of the disease. For example, fatigue observed in SMA test patients reflected a 17% decrease in gait velocity from the first minute to the last minute during the 6MWT.

In one embodiment, a subject having SMA and being administered a therapy or combination therapy described herein exhibits an increase in RULM score of at least 2-fold, at least 3-fold, at least 4-fold, or at least 5-fold after administration of the therapy or combination therapy.

CHOP INTEND Score

The CHOP INTEND is a clinician-rated questionnaire developed to assess motor skill in spinal muscular atrophy type I. The 16 items are scored from 0 to 4. The global score ranges from 0 to 64, a higher score indicating better motor skills (See: Glanzman A M, Mazzone E, Main M, Pelliccioni M, Wood J, Swoboda K J, Scott C, Pane M, Messina S, Bertini E, Mercuri E, Finkel R S. The Children's Hospital of Philadelphia Infant Test of Neuromuscular Disorders (CHOP INTEND): test development and reliability. Neuromuscul Disord. 2010 March; 20(3):155-61). CHOPS INTEND is validated and has been shown reliable in SMA Type I subjects. It was derived in part from TIMP (Test of Infant Motor Performance) and is designed to measure motor function in weak infants with neuromuscular disease. The test includes active (spontaneous, goal-directed) and elicited reflex movements but does not include respiratory or feeding assessments.

In one embodiment, a subject having SMA and being administered a therapy or combination therapy described herein exhibits an increase in at least one of the 16 CHOP items of at least 2-fold, at least 3-fold, at least 4-fold, or at least 5-fold after administration of the therapy or combination therapy.

CMAP Test

Neuromuscular damage may be assessed using a compound muscle action potential (CMAP) test which provides an electrical stimulation of a nerve and records the compound muscle action potential from surface electrodes overlying a muscle supplied by that nerve. The test may involve stimulation at the wrist, the elbow, and less frequently, the axilla and the brachial plexus The CMAP measures the summated voltage response from the individual muscle fiber action potentials. Typically, the electrodes were placed over a target muscle of the subject and CMAP was obtained by giving supramaximal stimuli (i.e., a stimulus having strength significantly above that required to activate all the nerve or muscle fibers in contact with the electrode), which were repeated every 30-60 seconds for a period of 2-3 minutes until stable baseline amplitude was obtained. Then the subject contracted the target muscles for 2-5 minutes, with brief (3-4 seconds) rest every 15 seconds to prevent muscle ischemia. CMAP was recorded every minute when muscle is exercised and every 1-2 minutes after exercise for a period of 30 minutes or until no further decrease in the amplitude of CMAP was observed. CMAP amplitude is typically measured in millivolts (mV). Percentage of amplitude decrease was calculated by subtracting the smallest amplitude after exercise from the greatest amplitude after exercise and dividing it by the greatest amplitude after exercise. In CMAP tests done on a group of people without muscle disease the CMAP amplitude decrease varied from 5.4% to 28.8% (mean 15%). A decrease of more than 40% in the amplitude of CMAP was considered diagnostic of muscle disease.

In some embodiments, the decrease in amplitude of CMAP in a subject is at least 40%, 45%, 50%, 55%, 60%, 65%, 70%, 80%, 90%, or more. In some embodiments, the amplitude of the negative peak of CMAP in a subject with a muscle disease (e.g., SMA) is substantially lower compared to the corresponding amplitude of the negative peak of CMAP in a subject without muscle disease (control subject). In one embodiment, the amplitude of the negative peak of CMAP in a subject with a muscle disease is at least 30%, 40%, 45%, 50%, 55%, 60%, 65%, 70%, 80%, 90%, or more, lower than the corresponding amplitude of the negative peak of CMAP in a control subject. CMAP test can be used to determine the effectiveness of therapy by comparing CMAP decrements pre and post treatment, as described herein.

In one embodiment, a subject having SMA and being administered a therapy or combination therapy described herein exhibits an increase in CMAP of at least 2-fold, at least 3-fold, at least 4-fold, or at least 5-fold after administration of the therapy or combination therapy.

MUNE Test

Motor unit number estimation (MUNE) is a test that can be used to determine the approximate number of motor neurons in a muscle or group of muscles. MUNE test provides a calculated value that represents the estimated number of motor neurons or axons (motor control input) supplying the muscle or group of muscles being tested. In addition, MUNE provides a means of measuring motor unit size and enables tracking of loss of motor neurons. MUNE test is typically used most often in neuromuscular disorders such as amyotrophic lateral sclerosis and spinal muscular atrophy.

Typically, in a MUNE test, bipolar electrodes at the skin surface stimulated the nerve strongly enough to activate all of the motor axons within it, resulting in full depolarization and contraction of the muscle, which corresponds with activation of all of its motor units (i.e., motor neurons or axons) and component muscle fibers at the site of placement of electrodes. The electrical impulse generated by this muscle activity is recorded by electrodes placed over the muscle on the skin surface. In a healthy muscle, all the motor units and all their muscle fibers are activated simultaneously during this test, generating the compound motor action potential (CMAP), which is the maximum motor response. The amplitude of the CMAP corresponds to the total number of motor units and muscle fibers activated. The amplitude of the third response at each site is summed, then divided by 9 to yield the average single motor unit action potential (SMUP) amplitude. This amplitude is divided into the maximum compound motor unit action potential (CMAP) amplitude to yield the MUNE.

Average MUNE for normal, healthy subjects is 225 (±87), and, for example, was 41.9 (±39) among subjects with a muscle disease (e.g., ALS or SMA) at baseline. Subjects having muscle conditions or disorders exhibit clear decrements over time, with an average rate of decline as high as approximately 9% per month. In one embodiment, the average rate of monthly decline in MUNE values in a subject with a muscle disease or disorder is at least 5%, 10%, 15%, 20%, 25%, 30%, 35%, 40%, 50%, 60%, or more, relative to the corresponding MUNE values in a control subject without muscle disease. It is possible that a subject with a muscle disease can have normal CMAP amplitude measurements but a MUNE value less than 50% of the control subject. In one embodiment, the subject with normal CMAP amplitude values has a MUNE value that is at least 5%, 10%, 15%, 20%, 25%, 30%, 35%, 40%, 50%, 60%, or more, lower relative to the corresponding MUNE values in a control subject without muscle disease.

In one embodiment, a subject having SMA and being administered a therapy or combination therapy described herein exhibits an increase in a MUNE value of at least 2-fold, at least 3-fold, at least 4-fold, or at least 5-fold after administration of the therapy or combination therapy.

Effect on Mass and/or Function of Muscle in the Human Subject

Administration of a myostatin inhibitor and/or function of a muscle tissue in the human subject. In some embodiments, the muscle tissue is selected from the group consisting of a smooth muscle tissue, a skeletal muscle tissue and a cardiac muscle tissue. Smooth muscle tissue is made up from long tapering cells, generally involuntary and differs from striated muscle in the much higher actin/myosin ratio, the absence of conspicuous sarcomeres and the ability to contract to a much smaller fraction of its resting length. Smooth muscle cells are found particularly in blood vessel walls, surrounding the intestine and in the uterus. Cardiac muscle tissue is a striated but involuntary tissue responsible for the pumping activity of the vertebrate heart. The individual cardiac muscle cells are not fused together into multinucleate structures as they are in striated muscle tissue. Skeletal muscle tissue is under voluntary control. The muscle fibers are syncytial and contain myofibrils, tandem arrays of sarcomeres. There are two general types of skeletal muscle fibers: slow-twitch (e.g., type I fibers) and fast-twitch (e.g., type II fibers) according to the expression of their particular myosin heavy chain (MHC) isoform. Slow-twitch muscles are typically better equipped to work aerobically and help enable long-endurance feats such as distance running, while fast-twitch muscles typically fatigue faster but are better equipped to work anaerobically and are used in powerful bursts of movements like sprinting. The differentiation between slow and fast twitch muscle fibers is based on histochemical staining for myosin adenosine-triphosphatase (ATPase) and the type of myosin heavy chain. The slow twitch muscle fiber (predominantly type I fiber) is MHC isoform I and the three fast twitch isoforms (predominantly type II fibers) are MHC isoform IIa, MHC isoform IId, and MHC isoform IIb (S. Schiaffino, *J. Muscle Res. Cell. Motil.*, 10 (1989), pp. 197-205). In some embodiments, the mass and/or function of a fast twitch muscle tissue in the human subject is increased. In other embodiments, the mass and/or function of a slow twitch muscle tissue in the human subject is increased.

In some embodiments, administration of an effective amount of a myostatin inhibitor, e.g., an antibody, or antigen-binding fragment thereof, described herein to a subject can cause an increase in muscle mass. Preferably, such an increase in muscle mass is clinically meaningful to benefit or otherwise improve the health status of the subject. For example, clinically meaningful changes in muscle mass may improve the patient's mobility, self-care, metabolism, etc. In some embodiments, the increase in muscle mass is an increase in lean muscle or lean muscles. In some embodiments, such increase in muscle mass is a systemic effect such that muscles in the whole body or substantially whole body show the measurable effect. In other embodiments, effects are localized to certain group/type of muscles.

In some embodiments, the mass of the muscle tissue, e.g., lean muscle tissue, is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the mass of the muscle tissue, e.g., lean muscle tissue, is increased by at least about 1-5%, 5-10%, 10-20%, 1-30%, 1-40%, 1-50%, 10-50%, 20-30%, 20-60%, 30-80%, 40-90%, or 50-100%. Such increase in muscle mass may be deduced or measured by any suitable known methods, including measurement of cross-sectional area via MRI (e.g., forearm cross section), circumference, diaphragm width (e.g., via ultrasound), etc.

In some embodiments, administration of an effective amount of an antibody or antigen-binding fragments thereof described herein to a subject can cause an enhancement in muscle function. Muscle function may be assessed by a variety of measures, including, without limitation: force generation, grip strength (e.g., maximum grip strength), endurance, muscle oxidative capacity, dynamic grip endurance, etc. In some embodiments, serum creatinine levels are used as a validated biomarker indicative of muscle mass, albeit with limited sensitivity.

In some embodiments, administration of the myostatin inhibitor increases locomotor function in the human subject. In some embodiments, the locomotor function of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the locomotor function of the human subject is increased by at least about 1-5%, 5-10%, 10-20%, 1-30%, 1-40%, 1-50%, 10-50%, 20-30%, 20-60%, 30-80%, 40-90%, or 50-100%.

In another embodiment, administration of the myostatin inhibitor increases the muscle strength in the human subject. In some embodiments, the muscle strength of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the muscle strength of the human subject is increased by at least about 1-5%, 5-10%, 10-20%, 1-30%, 1-40%, 1-50%, 10-50%, 20-30%, 20-60%, 30-80%, 40-90%, or 50-100%.

In some embodiments, administration of the myostatin inhibitor and/or SMN corrector can cause clinically meaningful changes in muscle function which corresponds to enhanced functionality of the patient. In some embodiments, enhanced functionality includes improvement in the patient's mobility, self-care, metabolism, etc.

Effect on the Level of Intramuscular Fat Deposits

Administration of the myostatin inhibitor and/or SMN corrector affects the level of intramuscular fat deposits in the human subject. In one embodiment, the fatty replacement of muscle tissue is prevented, alleviated, or delayed. As used herein, the term "adipose tissue" refers to fat including the connective tissue that stores fat. Adipose tissue is derived from preadipocytes.

Mass of adipose tissue can be determined by any method known to a person of ordinary skill in the art. For example, adipose tissue may be measured by dual-energy X-Ray absorptiometry (DXA). Quantification of intramuscular fat deposits may also be determined using magnetic resonance imaging (MRI). For example, MR dual-echo dual-flip angle spoiled gradient recalled (SPGR) MRI technique or the three-point Dixon MRI technique may be used for the assessment of the levels of intramuscular fat deposits in a subject. The aforementioned MRI techniques and the protocols to quantify intramuscular fat deposits are described in, for example, Leroy-Willig et. al., Magnetic Resonance Imaging Vol 15, No. 7 pp. 737-744, 1997, and Gaeta et. al., Skeletal Radiol, DOI 10.1007/s00256-011-1301-5; the contents of each are incorporated by reference herein in their entirety. It should be appreciated, however, that other methods of determining and quantifying of intramuscular fat deposits are known in the art and would be apparent to the skilled artisan.

In some embodiments, the level replacement of intramuscular fat deposits is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100% after administration of the therapy to the subject.

Effect on Life Quality of the Human Subject

Assessment of the quality of life in patients with severe or chronic conditions, such as SMA patients, may involve integrated approaches to evaluate various aspects of physical, mental, social and other parameters. Generally, a greater degree of quality of life is associated with factors such as: accessibility to assistive technology; community reintegration; functionality with lower limb and walking and/or wheeled mobility; mental health; severity in neurological impairment and autonomic dysfunction; pain management; functional independence and self-care; upper limb strength; and spasticity control. Administration of a myostatin inhibitor described herein increases the quality of life of the human subject to achieve a clinically meaningful improvement as measured by a standardized quality-of-life test/system.

A number of suitable tests for assessing the quality of life in patients are known in the art, including, without limitation: Spinal Cord Independence Measure (SCIM); Functional Independence Measure (FIM); Incontinence Quality of Life Questionnaire (I-QOL); Life Satisfaction Questionnaire (LISAT-9, LISAT-11); Quality of Life Index (QLI); Quality of Life Profile for Adults with Physical Disabilities (QOLP-PD); Quality of Well Being (QWB) and Quality of Well Being-Self-Administered (QWB-SA); Qualiveen; Satisfaction with Life Scale (SWLS, Deiner Scale); Short Form 36 (SF-36); Sickness Impact Profile 68 (SIP 68); and World Health Organization Quality of Life-BREF (WHOQOL-BREF).

In some embodiments, quality of life is assessed in accordance with the SF-36 Quality of Life Scoring System, which is a validated scoring system, in which an 8 point change is considered clinically meaningful. In some embodiments, administration of an effective amount of the myostatin inhibitor results in a clinically meaningful improvement in a standardized quality-of-life test score.

As used the herein, the term "clinically meaningful improvement" refers to a significant improvement over a standard level. In some embodiments, a patient's SF-36 Quality of Life scores are increased by at least 8 points, following treatment with an effective amount of an antibody or antigen-binding fragments thereof described herein, as compared to the patient's score prior to the treatment. In some embodiments, patients achieve higher scores as assessed by the SF-36 Quality of Life Test, for example, at least 9, 10, 11, 12, 13, 14, 15, 16, 17, 18, 19, 20, 30, 40, or 50 points increase in the scores from the SF-36 Quality of Life Scoring System. In other embodiments, the scores from the SF-36 Quality of Life Scoring System is increased by at least about 8-10, 10-15, 15-20, 20-30, 30-40, 40-50, 8-20, 8-30, 8-40, or 8-50.

In some embodiments, one or more of Quality of Life measures are employed to assess patients' quality of life before and after treatment with the inhibitors of myostatin signaling disclosed herein. Advantages of this test include: i) it is easy to administer; ii) it assesses both physical function and mental health; and, iii) it is highly validated for a number of clinical indications.

Effect on Preventing Muscle Loss or Atrophy

Administration of an effective amount of the myostatin inhibitor and/or SMN corrector prevents, delays, or alleviates muscle loss or atrophy in the human subject at risk of developing muscle loss and/or atrophy. In some embodiments, muscle loss or atrophy is decreased or prevented by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, muscle loss or atrophy is decreased or prevented by at least about 1-5%, 5-10%, 10-20%, 1-30%, 1-40%, 1-50%, 10-50%, 20-30%, 20-60%, 30-80%, 40-90%, or 50-100% as compared to control group that does not receive a myostatin inhibitor and/or a SMN corrector.

In particular embodiments, the control group referenced above has only been treated with a SMN corrector. In a different embodiment, the control group referenced above has not been treated with a SMN corrector.

Administration of an effective amount of the myostatin inhibitor and/or SMN corrector can result in preventing further deterioration of affected muscle, or delaying or slowing of the rate of disease progression in these patients. In some embodiments, administration of an effective amount of the myostatin inhibitor and/or SMN corrector can delay the muscle loss or atrophy in the human subject at risk of developing muscle loss and/or atrophy, as compared to control group that does not receive myostatin inhibitor and/or SMN corrector. In some embodiments, muscle loss or atrophy is delayed for at least 1 month, 2 months, 3 months, 6 months, 8 months, 12 months, 2 years, 3 years 5 years or 10 years in the human subject receiving myostatin inhibitor and/or SMN corrector, as compared to control group that does not receive myostatin inhibitor and/or SMN corrector.

In particular embodiments, the control group referenced above has only been treated only with SMN corrector. In a different embodiment, the control group referenced above has not been treated with SMN corrector.

Preventing further deterioration of affected muscle refers to maintaining disease status which includes for example, maintaining motor functional test scores over longer periods of time as compared to control, slower rate of disease progression, as measured/monitored by motor function test; fewer hospitalizations, fewer injuries (e.g., bone fractures), longer time before requiring ventilator, longer time before becoming wheelchair-bound, etc.

Prevention of muscle loss or atrophy by the use of a myostatin inhibitor and/or SMN corrector described herein can be readily monitored or assessed by any suitable methods to evaluate motor function involving affected muscles.

Effects on Bone Homeostasis

Administration of an effective amount of the myostatin inhibitor may provide clinically meaningful protection of the bones in patients. Such effects include, but are not limited to: increased bone density; increased bone mass; increased bone mineral density; increased bone strength; prevention of bone loss; and reducing the frequency of bone fractures in patients. The art is familiar with suitable techniques which can be employed to measure various parameters of bone homeostasis. These include imaging techniques, such as micro CT scanning, and central dual-energy x-ray absorptiometry (central DXA) test.

Effects on Metabolic Regulation

Administration of an effective amount of the myostatin inhibitor may provide clinically meaningful effects on metabolic regulation. These effects include, but are not limited to: prevention of developing metabolic dysregulation in patients; and alleviating metabolic dysregulation in patients.

i) Effect on Insulin Sensitivity of the Human Subject

Methods for measuring insulin sensitivity are known in the art, for example, glucose tolerance test, and fasting insulin or glucose test. During a glucose tolerance test, a fasting patient takes a 75 gram oral dose of glucose, and then blood glucose levels are measured over the following two hours. A glycemia less than 7.8 mmol/L (140 mg/dl) is considered normal, a glycemia of between 7.8 and 11.0 mmol/L (140 to 197 mg/dl) is considered as impaired glucose tolerance (IGT), and a glycemia of greater than or equal to 11.1 mmol/L (200 mg/dl) is considered diabetes mellitus. For fasting insulin test, a fasting serum insulin level greater than 25 mIU/L or 174 pmol/L is considered insulin resistance. In some embodiments, the metabolic rate is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the metabolic rate is increased by at least about 1-5%, 5-10%, 10-20%, 1-30%, 1-40%, 1-50%, 10-50%, 20-30%, 20-60%, 30-80%, 40-90%, or 50-100%.

ii) Effect on the Level of Adipose Tissue in the Human Subject

Administration of the myostatin inhibitor, e.g., antibody, or antigen binding fragment thereof, that specifically binds pro/latent myostatin affects the level of adipose tissue in the human subject. As used herein, the term "adipose tissue" refers to fat including the connective tissue that stores fat. Adipose tissue is derived from preadipocytes. Its main role is to store energy in the form of lipids, although it also cushions and insulates the body. The two types of adipose tissue are white adipose tissue (WAT), which stores energy, and brown adipose tissue (BAT), which generates body heat.

Brown adipose tissue (BAT) is known to function in the dissipation of chemical energy in response to cold or excess feeding, and also has the capacity to modulate energy balance. Activation of brown adipose tissue have been shown to improve glucose homeostasis and insulin sensitivity in humans suggesting that anyone with impaired insulin function might benefit from BAT activation (Stanford et al., J Clin Invest. 2013, 123(1): 215-223).

Beige adipose tissues are generated as a result of browning of WAT, also known as beiging. This occurs when adipocytes within WAT depots develop features of BAT. Beige adipocytes take on a multilocular appearance (containing several lipid droplets) and increase expression of uncoupling protein 1 (UCP1). In doing so, these normally energy-storing white adipocytes become energy-releasing adipocytes (Harms et al. Nature Medicine. 2013, 19 (10): 1252-63).

Visceral fat or abdominal fat (also known as organ fat or intra-abdominal fat) is located inside the abdominal cavity, packed between the organs (stomach, liver, intestines, kidneys, etc.). Visceral fat is different from subcutaneous fat underneath the skin, and intramuscular fat interspersed in skeletal muscles. Fat in the lower body, as in thighs and buttocks, is subcutaneous and is not consistently spaced tissue, whereas fat in the abdomen is mostly visceral and semi-fluid. An excess of visceral fat is known as central obesity, or "belly fat", in which the abdomen protrudes excessively and new developments such as the Body Volume Index (BVI) are specifically designed to measure abdominal volume and abdominal fat. Excess visceral fat is also linked to type 2 diabetes, insulin resistance, inflammatory diseases and other obesity-related diseases (Mokdad et al., JAMA: The Journal of the American Medical Association. 2001, 289 (1): 76-9).

Mass of adipose tissue can be determined by any method known to a person of ordinary skill in the art. For example, adipose tissue may be measured by dual-energy X-Ray absorptiometry (DXA).

Administration of the myostatin inhibitor, e.g., antibody, or antigen binding fragment thereof, that specifically binds pro/latent myostatin increases the level of brown adipose tissue and/or the level of beige adipose tissue in the human subject. On the other hand, administration of the myostatin inhibitor, e.g., anti-pro/latent myostatin antibody, or antigen-binding portion thereof, decreases the level of white adipose tissue and visceral adipose tissue in the human subject.

In some embodiments, the level of brown or beige adipose tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the level of brown or beige adipose tissue is increased by at least about 1-5%, 5-10%, 10-20%, 1-30%, 1-40%, 1-50%, 10-50%, 20-30%, 20-60%, 30-80%, 40-90%, or 50-100%.

In some embodiments, the level of white or visceral adipose tissue is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the level of white or visceral adipose tissue is decreased by at least about 1-5%, 5-10%, 10-20%, 1-30%, 1-40%, 1-50%, 10-50%, 20-30%, 20-60%, 30-80%, 40-90%, or 50-100%.

iii) Effect on the Ratio of Adipose-to-Muscle Tissue in the Human Subject.

Administration of the myostatin inhibitor, e.g., antibody, or antigen binding fragment thereof, that specifically binds pro/latent myostatin decreases the ratio between adipose-to-muscle tissue in the human subject. In some embodiments, the ratio between adipose-to-muscle tissue is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the ratio between adipose-to-muscle tissue is decreased by at least about 1-5%, 5-10%, 10-20%, 1-30%, 1-40%, 1-50%, 10-50%, 20-30%, 20-60%, 30-80%, 40-90%, or 50-100%.

iv) Effect on Glucose Uptake in the Human Subject

Administration of the myostatin inhibitor, e.g., antibody, or antigen binding fragment thereof, that specifically binds pro/latent myostatin affects glucose uptake by tissues in the human subject. In some embodiments, glucose uptake by muscle tissue is increased. For example, glucose uptake by the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In some embodiments, glucose uptake by the muscle tissue is increased by at least about 1-5%, 5-10%, 10-20%, 1-30%, 1-40%, 1-50%, 10-50%, 20-30%, 20-60%, 30-80%, 40-90%, or 50-100%.

In other embodiments, glucose uptake by white adipose tissue, liver tissue and blood vessel tissue are reduced. In some embodiments, glucose uptake by white adipose tissue, liver tissue and blood vessel tissue are reduced by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, glucose uptake by white adipose tissue, liver tissue and blood vessel tissue are reduced by at least about 1-5%, 5-10%, 10-20%, 1-30%, 1-40%, 1-50%, 10-50%, 20-30%, 20-60%, 30-80%, 40-90%, or 50-100%.

v) Effect on Intramuscular Fat Infiltration in the Human Subject

Administration of the myostatin inhibitor, e.g., antibody, or antigen binding fragment thereof, that specifically binds pro/latent myostatin decreases intramuscular fat infiltration in the human subject. In some embodiments, intramuscular fat infiltration is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, intramuscular fat infiltration is decreased by at least about 1-5%, 5-10%, 10-20%, 1-30%, 1-40%, 1-50%, 10-50%, 20-30%, 20-60%, 30-80%, 40-90%, or 50-100%.

Effect of Delaying Loss of α-Motor Neurons

Administration of an effective amount of the myostatin inhibitor may delay the loss of α-Motor Neurons. The art is familiar with suitable techniques which can be employed to measure various parameters indicating the loss of α-Motor Neurons. These include immunofluorescence methods using imaging techniques, such as Homogeneous Time-Resolved Fluorescence (HTRF, Cisbio Bioassays), micro CT scanning, and Light and Electron microscopy.

Expression of Biomarkers

Changes in the level of certain biomarkers (e.g., plasma biomarkers) of SMA may be measured to monitor progression of the pathology, as well as the patients' responsiveness to treatment. Suitable methods and assays to measure changes in the level of suitable biomarkers from patient samples are known in the art. The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a marker protein include enzyme linked immunosorbent assays (ELISAs), Western blots, immunoprecipitations and immunofluorescence. In vitro techniques for detection of genomic DNA include Southern hybridizations. In vivo techniques for detection of mRNA include polymerase chain reaction (PCR), Northern hybridizations and in situ hybridizations. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

More specifically, monitoring the influence of agents (e.g., myostatin inhibitors and/or SMN correctors) on the level of expression of a marker can be applied not only in basic drug screening, but also in clinical trials, as well as for evaluating disease maintenance and progression, and patients' responsiveness to a particular therapy. For example, the effectiveness of an agent to affect marker expression can be monitored in biological samples collected from subjects receiving treatment for SMA, e.g., prior to, during and/or following treatment and measuring levels of the markers and/or changes in the levels of marker expression over time. In a preferred embodiment, the present invention provides a method for monitoring the effectiveness of treatment of a subject with an agent comprising the steps of (i) obtaining a pre-administration sample from a subject prior to administration of the agent(s); (ii) detecting the level of expression of one or more selected markers of the invention in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) assessing effectiveness of the therapeutic regimen, and if necessary altering or adjusting treatment accordingly. For example, increased expression of the marker gene(s) during the course of treatment may indicate ineffective dosage and the desirability of increasing the dosage. Conversely, decreased expression of the marker gene(s) may indicate efficacious treatment and no need to change dosage.

Suitable biomarkers include plasma proteins disclosed in Kobayashi et al. (2013) PLOS ONE, volume 8, issue 4, e60113. One or more biomarkers present in serum samples are preferred for ease of sample collection, although in certain cases muscle biomarkers may be used, for example, collected by tissue biopsy.

In some embodiments, SMA plasma protein markers are selected from the list below: CILP2 (Cartilage intermediate layer protein 2); TNXB (Tenascin XB); CLEC3B (Ctype lectin domain family 3, member B (tetranectin)); TNXB (Tenascin XB); ADAMTSL4 (ADAMTSlike 4); THBS4 (Thrombospondin 4); COMP (Cartilage oligomeric matrix protein); CRTAC1 (Cartilage acidic protein 1); F13B (Coagulation factor XIII, B polypeptide); PEPD (Peptidase D); LUM (Lumican); CD93 (Complement component 1, q subcomponent, receptor 1); Mixed complement C2/B; APCS (Amyloid P component, serum); VTN (Vitronectin); DPP4 (Dipeptidylpeptidase 4 (CD26, adenosine deaminase complexing protein 2)); CRP (C-reactive protein, pentraxinrelated); HBB (Hemoglobin beta); GSN (Gelsolin); NCAM1 (Neural cell adhesion molecule 1); CFI I factor (complement); APOA4 (Apolipoprotein AIV); VTN (Vitronectin); F13A1 (Coagulation factor XIII, A1 polypeptide); INHBC (Inhibin, beta C); RPS27A (Ubiquitin and ribosomal protein S27a precursor); CDH13 (Cadherin 13, Hcadherin (heart)); mixed Complement C2/B; C2 Complement component 2; CP (Ceruloplasmin (ferroxidase)); HBA (Hemoglobin subunit alpha); QSOX1 (Quiescin Q6); LRG1 (Leucine-rich alpha2-glycoprotein 1); C9 (Complement component 9); SERPINA10 (Serpin peptidase inhibitor, clade A (alpha1 antiproteinase, antitrypsin), member 10); ALP (Alkaline phosphatase, liver/bone/kidney); mixed fc-gamma receptor III-A/B; PROC (Protein C (inactivator of coagulation factors Va and VIIIa)); VCAM1 (Vascular cell adhesion molecule 1); GAPDH (Glyceraldehyde-3-phosphate dehydrogenase); OMD (Osteomodulin); IGKVD41 (Immunoglobulin kappa variable 41); IGFBP6 (Insulinlike growth factor binding protein 6); PTPRG (Protein tyrosine phosphatase, receptor type, G); S100A9 (S100 calcium binding protein A9 (calgranulin B)); VNN1 (Vanin 1); SERPIND (Serpin peptidase inhibitor, clade D (heparin cofactor), member 1); CA1 (Carbonic anhydrase I); CTSD (Cathepsin D (lysosomal aspartyl peptidase)); HP (Haptoglobin); SELENBP1 (Selenium binding protein 1); ORM2 (Orosomucoid 2); PRDX2 (Peroxiredoxin 2); AOC3 (Amine oxidase, copper containing 3 (vascular adhesion protein 1)); COL6A3 (Collagen, type VI, alpha 3); PZP (Pregnancyzone protein); COL6A1 (Collagen, type VI, alpha 1); PARK7 (Parkinson disease (autosomal recessive, early onset) 7); THBS1 (Thrombospondin 1); CAT (Catalase); LCP1 (Lymphocyte cytosolic protein 1 (Lplastin)); AFM (Afamin); HPR (Haptoglobin-related protein); SELL1 (Selectin L (lymphocyte adhesion molecule 1)); ENG (Endoglin); PFN1 (Profilin 1); PI16 (Peptidase inhibitor 16); SERPINA6 (Serpin peptidase inhibitor, clade A (alpha1 antiproteinase, antitrypsin), member 6); F9 (Coagulation factor IX); PROCR (Protein C receptor, endothelial); ORM1 (Orosomucoid 1); NEO1 (Neogenin homolog 1); MMRN2 (Multimerin 2); LGB (Beta-lactoglobulin); CNTN4 (Contactin 4); SHBG (Sex hormonebinding globulin); CA2 (Carbonic anhydrase II); IGFBP5 (Insulinlike growth factor binding protein 5); PLTP (Phospholipid transfer protein); FGA (Fibrinogen alpha chain); TPM4 (Tropomyosin 4); MB (Myoglobin); SPP1 (Osteopontin); AXL (AXL receptor tyrosine kinase); APSC (Amyloid P component, serum); CRP (C-reactive protein, pentraxinrelated); CCL22 (Chemokine (C-C motif) ligand 22 (macrophage derived chemokine)); THBD (Thrombomodulin); CALCA (Calcitonin); LEP (Leptin); NPPB (Brain natriuretic peptide b); MMP2 (Matrix Metalloproteinase 2); CK (Creatine kinase muscle/bone); ACE (Angiotensin converting enzyme); FAPB3 (Fatty acid binding protein (heart)); CD40 (CD40 Ligand); MIF (Macrophage Migration Inhibitory Factor); ANGPT2 (Angiopoietin 2); AHSG (Alpha-2-HS-glycoprotein (fetuin A)); CFH (Complement factor H); IL8 (Interleukin 8); C3 (Complement component 3); PPY (Pancreatic polypeptide); VEGFA (Vascular endothelial growth factor); TF (Transferrin); PGF (Placental growth factor); EGF (Epidermal growth factor); GSTA1 (Glutathione S transferase alpha); SOD1 (Superoxide dismutase 1); VCAM1 (Vascular cell adhesion molecule 1); PAH (Plasminogen activator inhibitor 1); CSF1 (Macrophage colony stimulating factor 1); S100A12 (S100 Protein A12); VTN (Vitronectin); FASLG (Fas ligand); A1M (Alpha-1-microglobulin); AST (Astartate transaminase); ACCT (Alpha-1-antichymotrypsin); CCL3 (Chemokine (C-C motif) ligand 3 (Macrophage Inflammatory Protein 1 beta)); SORT1 (Sortilin); TBG (Thyroxine binding globulin); APOA1 (Apolipoprotein A1); MPO Myeloperoxidase); B2M (Beta 2 microglobulin); EPO (Erythropoietin); MMP10 (Matrix Metalloproteinase 10); PROS1 (Vitamin K Dependent Protein S); MMP7 (Matrix Metalloproteinase 7); AGER (Advanced glycosylation end products receptor); IL18 (Interleukin 18); CCL11 (Chemokine C-C motif ligand 11); IGA (Immunoglobulin A); C peptide (Proinsulin C Peptide); A2M (Alpha-2-macroglobulin); PDGF BB (Platelet Derived Growth Factor); CCL16 (Chemokine C-C motif ligand 16); ILIA (Interleukin 1 alpha); APOA4 (Apolipoprotein A4); MMP9 (Matrix metalloproteinase 9); SPP1 (Osteopontin); CLEC3B (Ctype lectin domain family 3, member B (tetranectin)); IGFBP6 (Insulin-like growth factor binding protein 6); FABP4 (Fatty acid binding protein (adipocyte)); CHI3L1 (Chitinase 3-like 1 (YKL-40)); LEP (Leptin); CTSD (Cathepsin D); MST1 (Macrophage stimulating 1 (hepatocyte growth factor-like)); MIF (Macrophage migration inhibitory factor); S100A4 (S100 calcium binding protein A4); GLO1 (Glyoxalase 1 (lactoylglutathione lyase)); ENG (Endoglin); FTL1 (Fms-related tyrosine kinase 1 (vascular endothelial growth factor receptor)); ERBB2 (Human epidermal growth factor receptor 2 (HER2)); NDKB (Nucleoside phosphatase kinase isoform B); PRDX-4 (Peroxiredoxin 4); PLAUR (Plasminogen activator, urokinase receptor); IL6R (Interleukin 6 receptor); CCL24 (Chemokine (C-C motif) ligand 24 (eotaxin 2)); GSN (Gelsolin); PSAT1 (Phosphoserine aminotransferase 1); and, TGFB1 (Transforming growth factor beta 1).

In some embodiments, biomarkers are selected from the list below, which represents top 13 SMA motor function regressors in two SMA populations: COMP; AXL; CD93 PEPD; THBS4; LUM; MB; DPP4; SPP1; CHI3L1; CDH13; APCS; and, LEP.

Additionally, or alternatively, any suitable physiological measurements known in the art may be carried out to assess muscle function, including, electrical impedance myography (EIM), quantitative muscle magnetic resonance imaging (qMRI), dual energy X-ray absorptiometry (DEXA), etc.

Therapies for Promoting Muscle Hypertrophy

In another aspect, the present invention provides use of a myostatin inhibitor for promoting muscle hypertrophy to improve muscle function in a subject who has retained or regained anabolic capacity in the muscle, characterized in that the anabolic pathway (cellular machinery for protein production) is sufficiently intact (i.e., functional and active).

Whilst this is typically the case for young/growing subjects (e.g., pediatric population), for older subjects, muscles may have lost robust anabolic capacities; in other words, the anabolic-catabolic balance tends to tip towards the latter. For myostatin inhibition to produce optimal effects in these subjects, it is contemplated that an agent that stimulates the anabolic pathway be administered in conjunction with a myostatin inhibitor. By concurrently boosting the anabolic arm of the cellular pathways, the target muscle may be rendered more responsive to the effects of myostatin inhibition.

Typically, muscle function in a subject who has retained or regained anabolic capacity is assessed by administering anabolic hormones to the subject, such as testosterone, and measuring its effects on muscle growth and strength. The response of these subjects to the anabolic hormones can be measured by methods known to a person of skill in the art.

In some embodiments, a subject who benefits from increased muscle mass is administered a myostatin inhibitor, such as those described herein. In the event the myostatin inhibition treatment does not produce significant benefits in the subject, further administration of an anabolic stimulator may be considered as a combination therapy for boosting the effect of the myostatin inhibitor in accordance with the present disclosure Subjects who may benefit from enhanced muscle growth may or may not present clinical symptoms of a myopathy. Thus, such use may provide a health benefit to generally "healthy" individuals, who nevertheless may benefit from improved muscle function, which may include an increase in muscle mass, enhanced ability to perform certain motor function (tasks), etc.

Myostatin inhibitors described herein, either as monotherapy or combination therapy, are suitable for treating patients who present one or more clinical symptoms of a myopathy. As used herein, the term "myopathy" refers to a muscular condition characterized by impaired muscle structure or function, typically resulting in muscle weakness. A "myopathy" may also include a muscular condition characterized by normal muscle structure but impaired or abnormal neuronal input, which in turn affects muscle function. A "myopathy" may also include inflammatory myopathies and/or autoimmune myopathies, e.g., myasthenia gravis.

Myopathies include muscular conditions that are neuromuscular or musculoskeletal in nature. In some embodiments, the myopathy is an inherited myopathy. Inherited myopathies include, without limitation, dystrophies, myotonias, congenital myopathies (e.g., nemaline myopathy, multi/minicore myopathy, and centronuclear myopathy), mitochondrial myopathies, familial periodic myopathies, inflammatory myopathies and metabolic myopathies (e.g., glycogen storage diseases and lipid storage disorder). In some embodiments, the myopathy is an acquired myopathy. Acquired myopathies include, without limitation, external substance induced myopathy (e.g., drug-induced myopathy and glucocorticoid myopathy, alcoholic myopathy, and myopathy due to other toxic agents), myositis (e.g., dermatomyositis, polymositis and inclusion body myositis), myositis ossificans, rhabdomyolysis, and myoglobinurias, and disuse atrophy. In some embodiments, the myopathy is disuse atrophy, which may be caused by prolonged disuse of muscles, leading to deterioration of normal muscle function. Disuse atrophy may be a result of hospitalization, bone fracture (e.g. a hip fracture) or by nerve injury. In some embodiments the myopathy is related to a disease or disorder such as amyotrophic lateral sclerosis (ALS), spinal muscular atrophy (SMA), cachexia syndromes due to renal failure, AIDS, cardiac conditions and/or cancer. In some embodiments the myopathy is related to ageing. In some embodiments the myopathy is related to sarcopenia. In some embodiments, the myopathy is related to paraspinal muscle atrophy (PMA).

In some embodiments, the myopathy is a primary myopathy. In one embodiments, a primary myopathy comprises disuse atrophy. In some embodiments, the disuse atrophy is associated with hip fracture, elective joint replacement, critical care myopathy, spinal cord injury or stroke. In some embodiments, the myopathy is a genetic muscle weakness associated with, for example, a muscular dystrophy.

In some embodiments, the myopathy is a secondary myopathy, in which muscle loss or dysfunction is secondary to a disease pathology. In some embodiments, secondary myopathy comprises denervation or cachexia. In some embodiments, the secondary myopathy is caused by a denervation associated with monitor neuron dysfunction. In some embodiments, motor neuron dysfunction is due to genetic mutation(s) that affect motor neurons. Diseases known to involve mutations in motor neurons include, but are not limited to, amyotrophic lateral sclerosis (ALS) and spinal muscular atrophy (SMA). In some embodiments, the secondary myopathy is a cachexia associated with renal failure, AIDS, a cardiac condition, cancer or aging. In some embodiments, the secondary myopathy is caused by a nerve injury, including unwanted nerve injury sustained during a medical procedure, such as surgeries. Detrimental effects of such injury to the function of a target tissue (e.g., target muscle) may be effectively treated by administration of a myostatin inhibitor described herein. For example, such administration may prevent and/or alleviate myopathy, and/or facilitate recovery.

Where intended clinical outcome of myopathy treatment is primarily to promote muscle growth (hypertrophy), patients may be administered with a myostatin inhibitor, such as those described herein, initially as a monotherapy. Responsiveness to the therapy should be monitored for clinical effects. If meaningful benefits do not result from the monotherapy within a reasonable time frame, e.g., within 1-6 months of initiating the myostatin inhibition therapy, supplementing with an anabolic stimulator may be considered as a combination therapy.

Alternatively, myopathy patients with a catabolic background, are likely to require concurrent anabolic boosting to realize full effects of myostatin inhibition to achieve meaningful muscle growth and therefore are considered candidates for a combination therapy. These patient populations include, but are not limited to: those who are elderly (e.g., 65 years or older), those presenting clinical symptoms of sarcopenia, those presenting clinical symptoms of cachexia, those presenting symptoms of osteoporosis, those who suffer from frequent or chronic infections, those with conditions causing general immunodeficiency, those with severe injury or disease that causes prolonged immobility, etc.

Accordingly, the present invention encompasses combination therapies that include a myostatin inhibitor and an anabolic stimulator. Such combination therapies may be advantageous for the treatment of any conditions in which the patient benefits from improved motor and/or metabolic function but whose anabolic capacities are compromised.

Therapeutic regimens aimed to achieve both myostatin inhibition and anabolic stimulation may be particularly advantageous for elderly populations. Therefore, the present disclosure encompasses combination therapies that incorporate both an inhibitor of myostatin signaling and an agent that boosts or favors anabolic pathways, e.g., an anabolic stimulator. For example, such combination therapies may be useful for treating age-related muscle conditions, such as sarcopenia. This is based on the observation that as part of normal aging process, anabolic activities are gradually lost as evidenced by decrease in protein synthesis, slower metabolism, etc., and with this backdrop, myostatin inhibition may be less effective in exerting its muscle-enhancing effects. Similarly, such combination therapies may be useful for the treatment of conditions, such as cachexia, sporadic inclusion body myositis (SIBM), and disuse-related muscle wasting. It is contemplated that in the presence of an agent that restores or boosts activities of the cellular anabolic machinery, muscle-enhancing effects of myostatin inhibition may be fully achieved. This may at least in part explain why so many myostatin inhibitors in the clinic to date have shown limited success in achieving clinically meaningful outcome. These studies typically involved older patients, whose anabolic capacities were likely weakened due to age or other conditions that drive the equilibrium preferentially towards a catabolic state over an anabolic state. This recognition sheds lights on the selection of appropriate patient populations that are likely to respond to myostatin inhibitor therapies, and the present invention encompasses such recognition.

As used herein, agents that boost cellular anabolic pathways include any agents that stimulate or favors protein synthesis over protein breakdown and may be collectively referred herein to as "anabolic stimulator." Typically, anabolic stimulation in a tissue/organ can lead to hypertrophy as a result of net positive protein synthesis over protein breakdown in the tissue/organ. By contrast, when catabolic pathways dominate over anabolic pathways, the net result may include atrophy of the tissue/organ due to protein breakdown being favored over protein synthesis. Therefore, the net outcome is likely a balance between these opposing arms of signaling in vivo.

Many anabolic stimulators are known in the art. These include, without limitation: IGF1 agonists, anabolic hormones, testosterone, steroids (e.g., androgens, oxymetholone, estrogens, progestrogens, etc.), GH/somatotropin, parathyloid hormone (PTH), prostaglandins, leptin, statin, and any derivatives thereof. Any agents that promote or stimulate protein synthesis and/or generally increase the rate of metabolism may function as an anabolic stimulator.

According to the invention, anabolic stimulators may be administered to patients who are either responders, poor responders, or non-responders of a myostatin inhibitor therapy. For the poor responders or non-responders, concurrent stimulation of anabolic pathways may improve anabolic capacity of the subject, thereby allowing the myostatin inhibitor to benefit from improved motor and/or metabolic function.

Although poor responders and/or non-responders of myostatin inhibitors may nevertheless benefit from anabolic stimulation, an alternative patient population includes those who are responders of a myostatin inhibitor. It is contemplated that motor function in these individuals may be further improved by myostatin inhibition therapy used in combination with anabolic stimulator therapy.

Therapies for Preventing Muscle Atrophy

In some embodiments, the methods of the present invention are suitable for preventing muscle loss (atrophy). Prevention of muscle atrophy may be desirable across a wide range of patient populations, including those who are generally in good health. Thus, the invention is useful in any situations where intended clinical outcome includes the prevention of muscle loss. This is at least in part based on the notion of the broader role of myostatin as a "metabolic switch" to control muscle homeostasis upon sensing energy expenditure of the body (such as glucose levels) by favoring muscle breakdown and/or fat synthesis. Myostatin inhibition therapies described herein can be employed to counter this action.

Patients suitable for a myostatin inhibition therapy therefore include those suffering from various genetic disorders, muscle conditions, metabolic disorders, injuries, etc. Injuries can include, but are not limited to: injuries or damage to muscles, bones, tendons, and nerves. Patients with severe injury or illness that causes prolonged immobility may also benefit from myostatin inhibition therapies.

In some embodiments, the methods of the present invention are suitable for preventing muscle atrophy. Muscle atrophy is a highly regulated catabolic process which occurs during periods of disuse (e.g. disuse atrophy) and/or in response to injury or heightened systemic inflammation (e.g., cachexia). Muscle atrophy may involve a wide range of clinical conditions, including systemic conditions such as spinal cord injury, as well as more localized conditions such as vocal cord paresis/paralysis. As used herein, the term "vocal cord paresis/paralysis" refers to a condition that results from abnormal nerve input into the voice box muscles (laryngeal muscles). Paralysis may involve the total interruption of nerve impulse, resulting in no movement; paresis may involve the partial interruption of nerve impulse, resulting in weak or abnormal motion of laryngeal muscles. In some embodiments, the anti-myostatin antibody, or antigen binding fragment thereof, is administered locally, for example, via direct local injection into the affected vocal cord muscle(s).

In some embodiments, the methods of the present invention are suitable for treating or preventing muscle conditions and disorders, including paraspinal muscle atrophy (PMA). In one embodiment, the antibodies, or antigen binding fragments thereof, described herein are used in methods of treatment of a paraspinal muscle atrophy that is a postoperative paraspinal muscle atrophy, i.e., a paraspinal muscle atrophy after a surgery. In one embodiment, the methods of treatment include treating a nerve injury-dependent muscle atrophy. In one embodiment, the methods of treatment as described herein include treating a postoperative nerve injury-dependent muscle atrophy. In one embodiment, the methods of treatment include treating a postoperative muscle atrophy, in which the surgery is a spinal surgery. In one embodiment, the methods of treatment include treating a postoperative muscle atrophy, in which the spinal surgery is a lumbar spine surgery or a lumbar spine procedure, e.g., a lumbar fusion procedure, a lumbar nonfusion procedure, a posterior lumbar fusion procedure, an anterior lumbar fusion procedure, a minimally invasive (MIS) posterior lumbar decompression procedure, a minimally invasive (MIS) posterior lumbar fusion procedure, a non-MIS equivalent procedure, etc. In one embodiment, the methods of treatment include treating a paraspinal muscle atrophy after a lumbar spine fusion procedure. In one embodiment, the methods of treatment include treating a paraspinal muscle atrophy after a posterior lumbar spine fusion procedure. In one embodiment, the methods of treatment include treating a paraspinal muscle atrophy after a non-MIS lumbar fusion procedure. In some embodiments, administration of an effective amount facilitates or accelerates recovery from a condition, such as injuries, surgeries and other medical procedures. Suitable such conditions may involve a condition that is associated with a nerve damage (whether resulting from an injury or a surgical or other clinical procedure).

Another aspect of the disclosure includes a method of treating a subject having a disease or condition related to congenital myopathies. Exemplary congenital myopathies include, without limitation, X-linked myotubular myopathy, autosomal dominant centronuclear myopathy, autosomal recessive centronuclear myopathy, nemaline myopathy, and congenital fiber-type disproportion myopathy.

Another aspect of the disclosure includes a method of treating a subject having a muscle disease or condition related to muscular dystrophies. Exemplary muscular dystrophies include, without limitation, Duchenne's, Becker's, facioscapulohumeral (FSH), and Limb-Girdle muscular dystrophies.

Another aspect of the disclosure includes a method of treating a subject having a urogynecological related disease or condition, glottic disorders (stenosis), extraocular myopathy, carpel tunnel, Guillain-Barré, or osteosarcoma.

Non-Limiting Embodiments for Carrying Out the Present Invention Include the Following:

In one embodiment, the invention provides a myostatin inhibitor for use in the treatment of spinal muscular atrophy (SMA) in a subject who is on an SMN corrector therapy or is expected to be on an SMN corrector therapy.

In some embodiments of the invention referenced above, the subject has non-ambulatory SMA. In a specific embodiment, the non-ambulatory SMA is SMA type I, type II or type III. In one embodiment, the subject has non-ambulatory SMA type III.

In any of these embodiments described herein, the subject can have a baseline Expanded Hammersmith Functional Motor Scale score of ≤65. In a specific embodiment, the subject has a baseline Expanded Hammersmith Functional Motor Scale score of ≤60, ≤55, ≤50, ≤45, ≤40, ≤35, ≤30, ≤25 or ≤20. In certain embodiments, the invention provides a myostatin inhibitor for use in the treatment of spinal muscular atrophy (SMA) in a subject who is on an SMN corrector therapy or is expected to be on an SMN corrector therapy, wherein the subject has a corrected Expanded Hammersmith Functional Motor Scale score of ≤60, ≤55, ≤50, ≤45, ≤40, ≤35, ≤30, ≤25 or ≤20, after receiving the SMN corrector therapy. In the certain embodiments of the invention referenced above, the subject has the corrected Expanded Hammersmith Functional Motor Scale score which has improved at least by one point over the baseline Expanded Hammersmith Functional Motor Scale score, after receiving the SMN corrector therapy. In one embodiment, baseline Expanded Hammersmith Functional Motor Scale score is determined prior to administration of a myostatin inhibitor to the subject. In one embodiment, baseline Expanded Hammersmith Functional Motor Scale score is determined prior to administration of a SMN corrector to the subject. In one embodiment, baseline Expanded Hammersmith Functional Motor Scale score is determined prior to administration of a myostatin inhibitor and a SMN corrector to the subject. In the certain other embodiments of the invention referenced above, the subject has not improved the corrected Expanded Hammersmith Functional Motor Scale score, after receiving the SMN corrector therapy.

In any of these embodiments described herein, the SMN corrector therapy comprises: a) a splice modifier; b) an SMN gene replacement or gene therapy; c) an SMN transcription enhancer; d) an SMN protein translation enhancer; or e) an SMN protein stabilizer In a particular embodiment, the SMN corrector is a central corrector or a systemic corrector. The term central corrector, as used herein, refers to an SMN corrector that is administered directly to the CNS via intrathecal route. The term central corrector, as used herein, refers to an SMN corrector that is systemically administered (e.g., orally administration) and affects not only the CNS but other tissues as well. In a different embodiment, the splice modifier of (a) is an RNA-based splice modifier. In a particular embodiment described herein, the splice modifier of (a) is administered to the subject intrathecally (i.e., administered into the spinal canal, or into the subarachnoid space so that it reaches the cerebrospinal fluid (CSF). In a different embodiment, wherein the SMN corrector therapy comprises an SMN gene replacement or gene therapy of (b) that is delivered with a vector, wherein the vector is optionally a viral vector. The terms "vector" and "viral vector" shall have their ordinary meaning and will be apparent to a person of skill in the biochemical arts.

In one embodiment, the splice modifier of (a) described above is a small molecule splice modifier. In a particular embodiment, the small molecule splice modifier is orally administered (i.e., administration where a substance is taken through the mouth). In a specific embodiment, the small molecule splice modifier is administered twice a day, once a day, once every two days, twice a week, or once a week.

In one embodiment, the invention provides a myostatin inhibitor for use in the treatment of SMA in a subject who has ambulatory SMA and who is not on an SMN corrector therapy. In a particular embodiment of the invention described above, the ambulatory SMA is ambulatory type III or type IV. In a further embodiment of the invention described above, the subject has a baseline Expanded Hammersmith Functional Motor Scale score of ≥40, ≥45, ≥50, or ≥55. In a different embodiment of the invention described above, the subject has a baseline Expanded Hammersmith Functional Motor Scale score ranging between 48 and 58, inclusive.

In one embodiment, the invention provides a myostatin inhibitor for use in the treatment of SMA in a subject who has been identified to be a carrier of an SMN mutation and who is not on an SMN corrector therapy. The term "a carrier of an SMN mutation" shall have their ordinary meaning and in this context, shall refer to is a person or other organism that has inherited the SMN recessive (i.e., non dominant) allele but does not display that trait or show symptoms of the disease caused by the SMN dominant allele. In a further embodiment of the invention described above, the subject is identified as a carrier by genetic screening in utero (i.e., inside uterus) or as an infant.

In one embodiment, the invention provides a myostatin inhibitor for use in increasing muscle mass in a subject, wherein i) a target muscle is in anabolic state; and/or, ii) the subject is treated with an anabolic stimulator.

In a further embodiment of the invention described above, the subject suffers from sarcopenia, cachexia, infections, prolonged immobility, or the subject is ≥65 years old.

In one embodiment, the invention provides a myostatin inhibitor for use in the prevention of muscle loss in a subject, wherein the subject suffers from a condition that comprises partial damage to neuromuscular function, and wherein the subject is on a neuronal therapy to treat or enhance motor neurons. In a further embodiment of the invention described above, the condition is a genetic disorder that affects neuronal function or an injury.

In any of these embodiments described herein, the myostatin inhibitor comprises: a) a small molecule antagonist of myostatin signaling; or, b) an antibody or antigen-binding portion thereof, which binds: i) pro/latent myostatin; ii) mature myostatin; or, iii) myostatin receptor.

In a further embodiment of the invention described above, the antibody or antigen-binding portion thereof binds the pro/latent myostatin but does not bind a mature myostatin or GDF11. In a different embodiment of the invention described above, the antibody or antigen-binding portion thereof binds a mature myostatin but does not bind a mature GDF11. In another embodiment of the invention described above, the antibody or antigen-binding portion thereof is administered to the subject at dosage ranging between 1 mg/kg and 30 mg/kg. In a different embodiment of the invention described above, the antibody or antigen-binding portion thereof is administered to the subject twice a week, once a week, every two weeks, or once a month. In any of the embodiments above describing the myostatin inhibitor, the antibody or antigen-binding portion thereof is administered to the subject intravenously (i.e. injected into a vein) or subcutaneously (i.e. injected into the skin).

In one embodiment, the invention provides the use of a myostatin inhibitor for the treatment of SMA, wherein the myostatin inhibitor is administered as a monotherapy or a combination therapy. In one embodiment, the invention provides the use of a myostatin inhibitor for promoting muscle growth in a subject, whose target muscle is in anabolic state and/or who is treated with an anabolic stimulator.

In one embodiment, the invention provides the use of a myostatin inhibitor for the prevention of muscle atrophy in a subject, who suffers from a condition that comprises partial damage to neuromuscular function and who is treated with a neuronal therapy. In a particular embodiment of the invention described herein, the condition is ALS. In one embodiment, the invention provides the use of a myostatin inhibitor in the manufacture of a medicament for the treatment of SMA. In a different embodiment, the invention provides a pharmaceutical composition comprising the myostatin inhibitor of embodiment C1, and an excipient. In a particular embodiment, the pharmaceutical composition described above is formulated for intravenous administration or subcutaneous administration.

In one embodiment, provided herein is a method for promoting muscle hypertrophy, the method comprising administering to a subject who would benefit from muscle growth and is a poor responder to a myostatin inhibitor, an effective amount of an anabolic stimulator so as to boost effects of the myostatin inhibitor. In one embodiment, the anabolic stimulator and the myostatin inhibitor are administered as a combination therapy.

In one embodiment, the subject suffers from a condition selected from the group consisting of sarcopenia, cachexia, chronic SCI, chronic or frequent infection(s), osteoporosis, and frequent falls/bone fractures. In one embodiment, the subject is 65 years of age or older.

In one embodiment, the subject is further treated with a neuronal therapy. In one embodiment, the subject has amyotrophic lateral sclerosis (ALS) or SMA.

In one embodiment, the myostatin inhibitor is a small molecule antagonist of myostatin or a biologic antagonist of myostatin. In another embodiment, the biologic antagonist of myostatin is an antibody, or an antigen binding portion thereof.

In one embodiment, disclosed herein is a method for treating a muscle condition in a human subject, the method comprising a step of: selecting a human subject who has a target muscle which has intact anabolic capacities, wherein functional neuromuscular signaling between the target muscle and an innervating motor neuron is partially impaired, and administering to the human subject a myostatin inhibitor in an amount effective to enhance function of the target muscle, thereby treating the muscle condition in the human subject. In one embodiment, the target muscle has retained or regained at least partial innervation of the motor neuron. In one embodiment, the target muscle comprises fast-twitch type II fibers. In one embodiment, the human subject is a pediatric subject.

In one embodiment, the method further comprises administering an anabolic stimulator to the subject. In one embodiment, the anabolic stimulator is administered to the subject before the administration of the myostatin inhibitor, at the same time as the administration of the myostatin inhibitor, or after the administration of the myostatin inhibitor. In one embodiment, the muscle condition is associated with a defect in the motor neuron. In one embodiment, the defect is a genetic defect. In one embodiment, the genetic defect is a mutation in Smn1.

In one embodiment, the method further comprises administering an agent that corrects the genetic defect to the human subject. In one embodiment, the agent is a splice modulator. In one embodiment, the agent is a small molecule agent or a nucleic acid agent. In one embodiment, the agent increases motor neuron function. In one embodiment, the motor neuron function includes membrane excitability, axonal transport, vesicle trafficking, neurotransmitter release, mitochondrial function, and/or mitochondrial availability. In one embodiment, the agent is an SMN corrector.

In one embodiment, the muscle condition is associated with a neuromuscular disease. In one embodiment, the neuromuscular disease is spinal muscular atrophy (SMA). In one embodiment, the SMA is type I SMA, type II SMA, or type III SMA. In one embodiment, the type III SMA is ambulatory SMA or non-ambulatory SMA.

According to the invention, any of the myostatin inhibitors described herein may be formulated into a pharmaceutical composition comprising the myostatin inhibitor and optionally an excipient. Such pharmaceutical compositions are used for the treatment of a disease or condition in human subjects either as a monotherapy or combination therapy in accordance with the present disclosure.

The invention encompasses use of any myostatin inhibitor described herein for the manufacture of a medicament suitable for administration in human subjects, in accordance with the present disclosure.

This invention is further illustrated by the following example which should not be construed as limiting.

EXAMPLES

Example 1: SRK-015: Specific Inhibition of Myostatin Activation

Like other TGFβ family members, myostatin is secreted as an inactive precursor, termed proMyostatin, in which presence of the prodomain occludes growth factor access to its receptor. Myostatin activation results from two distinct proteolytic cleavage steps (FIG. 1). ProMyostatin is first cleaved by a proprotein convertase, such as furin, that recognizes an RXXR site between the prodomain and the mature growth factor (30, 62). Following cleavage, the growth factor and prodomain remain associated, forming a latent complex (latent myostatin) which is unable to bind to its receptor. Active growth factor is released following a second cleavage by a member of the BMP/tolloid family (such as TLL-2; tolloid-like protein 2) (63). Following activation, myostatin binds to a receptor complex consisting of a type I receptor (Alk4/5) and a type II receptor (ActRIIA/B), resulting in phosphorylation and activation of Smad2/3. Activation of this signaling pathway ultimately leads to a reduction in protein synthesis and enhancement of protein degradation (64). Myostatin has been detected in two compartments in vivo: in circulation where the latent form predominates, and in muscle primarily as proMyostatin, which associates with extracellular matrix proteins such as perlecan (65-68).

A novel approach has been taken to discover and develop myostatin inhibitors with a unique mechanism of action and vastly improved specificity over most other inhibitors. As described above, the mature forms myostatin and GDF11 are 90% identical, making it difficult to identify antibodies which are specific for myostatin. However, the prodomains of these growth factors are only 43% identical. We have therefore targeted the precursor forms of myostatin and generated antibodies which specifically bind and inhibit activation of mature myostatin from the latent form.

Antibody SRK-015P ("P" for parental) was optimized to generate SRK-015, a fully human monoclonal antibody. SRK-015 differs from its parental clone by five residues in the variable domain outside the complementarity determining region. Both antibodies bind pro- and latent myostatin with high affinity (such as a single digit nanomolar range, e.g., 2-9 nM), while having no detectable binding to any form of GDF11 or Activin A, or to mature BMP9, BMP10, or TGFβ1. When incubated with proMyostatin (expressed and purified in house from a mammalian expression system), furin and mTTL-2 proteases, SRK-015 inhibited release of mature myostatin, as measured by activation of luciferase expression in a Smad2/3 reporter cell line. SRK-015 had no effect in a similar protease activity assay using proGDF11 as a substrate, again demonstrating the specificity of SRK-015 for pro and latent myostatin. SRK-015 did not inhibit the ability of mature myostatin to signal in this assay. Both SRK-015 and SRK-015P had similar functional activity towards human and mouse proMyostatin in the reporter assay such that EC50 values for the two antibodies in proMyostatin activation assay using human and mouse proMyostatin, are similar. The protein fragments produced following cleavage of latent myostatin with mTLL-2 were analyzed to demonstrate that SRK-015 inhibited the second (tolloid-mediated) proteolysis step needed for myostatin activation. The ability of SRK-015 to bind the myostatin prodomain and to inhibit tolloid cleavage has been shown. Purified recombinant latent myostatin was incubated with TLL-2 tolloid protease in the presence of increasing concentrations of SRK-015. Samples were separated by reducing SDS-PAGE and probed by Western blot with an antibody that recognizes the myostatin prodomain. Protease-dependent generation of cleavage fragment was inhibited with increasing amounts of the antibody, indicating that binding of SRK-015 to latent myostatin inhibited the second, tolloid-mediated cleavage step.

Example 2: In Situ Localization of Myostatin Pro Forms

As SRK-015 binds pro- and latent myostatin, the localization of these pro-forms in mouse skeletal muscle was investigated to ensure that these forms of myostatin are present in the extracellular space of muscle where they can be bound and inhibited by the SRK-015 antibody. Cryosections of tibialis anterior muscles from healthy mice were immunostained with antibody GDF8_068, which binds pro- and latent Myostatin, but not the mature growth factor. Tissues were also immunostained with antibodies against laminin, a component of muscle extracellular matrix. Results showed that the majority of myostatin precursors detected in muscle are in the extracellular space with little signal detected intracellularly. Significant co-staining occurred in interstitial extracellular spaces and around interstitial nuclei. To ensure the specificity of antibody staining, samples were immunostained with GDF8-068 which had been pre-incubated with a 100-fold molar excess of purified proMyostatin or proGDF11. Preincubation with proMyostatin completely abolished the signal, while preincubation with pro-GDF11 had no effect on staining. These data indicate that pro- and latent myostatin are present in the extracellular space in skeletal muscle and therefor able to be bound and inhibited by SRK-015.

Example 3: SRK-015 Prevents Dexamethasone-Induced Muscle Atrophy

SRK-015 increased muscle mass in healthy animals and reduced muscle loss in a dexamethasone-induced model of atrophy. As shown in FIG. 2, administration of single 20 mg/kg dose of SRK-015 to healthy male mice (vehicle group) resulted in a significant increase in muscle mass (17.5% versus IgG control) after 15 days Similar increases in muscle mass were also observed in female mice (data not shown). SRK-015 was also effective in preventing muscle loss upon dexamethasone treatment. Chronic administration of dexamethasone resulted in a significant loss of muscle mass by day 8 (16% decrease, IgG vehicle versus IgG Dex). A single 20 mg/kg administration of SRK-015 to dexamethasone treated mice prevented muscle atrophy throughout the course of the study, with no significant difference observed between treated and IgG vehicle control groups (FIG. 2).

Example 4: SRK-015P Enhances Muscle Weight and Function in Healthy Animals

In addition to increasing muscle mass, treatment with SRK-015 resulted in gains in muscle function. To assess SRK-015 mediated functional effects, a murinized version of SRK-015P (muSRK-015P) was used, in which the human IgG4 constant regions were replaced with those of mouse IgG1 to limit immune responses to the antibody over a four-week study. All the three antibodies, muSRK-015, muSRK-015P, and SRK-015, bind murine proMyostatin with similar affinities (Kd of 2.57 nM, 2.88 nM, and 8.35 nM, respectively). Healthy 10-week old C57BL/6 mice were treated with vehicle (PBS) or 20 mg/kg muSRK-015P weekly for four weeks. Following treatment, the nerve evoked function of the plantarflexor muscle group (gastrocnemius, soleus, and plantaris muscles) was examined in vivo across a physiologically relevant range of activation. Treated animals displayed a 19% increase in isometric torque generation at frequencies greater than 60 Hz (P=0.003) (FIG. 3A). A 31% increase in the maximal rate of contraction was observed, with no alterations to the force-frequency response (data not shown). To confirm the direct effects of myostatin inhibition on muscle, independent of nerve function and blood supply, the force in vitro of isolated EDL muscles was measured. In vitro assessment of EDL force generation demonstrated similar increases in function, with a 24% increase at 80 Hz (P=0.024), 28% at 100 Hz (P=0.010), and 27% at 150 Hz (P=0.011) (FIG. 3B). No alterations were observed in contraction and relaxation rates or of force frequency relationships the EDL following treatment (data not shown). As expected, four weeks of treatment with muSRK-015P also affected muscle mass, with the gastrocnemius increasing by 22% (P=0.009; FIG. 3C) and the EDL by 34% (P=0.007; FIG. 3D). When force was normalized to muscle weight, there was no difference between vehicle and treated groups for either the gastrocnemius or EDL muscles, indicating that the hypertrophy induced by muSRK-015P treatment did not negatively impact muscle quality or excitability (data not shown). Histological analysis of the plantarflexor group demonstrated a 27% increase in total cross sectional area (P=0.019, data not shown), the result of a 29% increase in the cross-sectional area of Type IIB muscle fibers (P=0.009; FIG. 3E). There was no change in the cross-sectional area of Type I, IIA, or IIX fibers, nor was there a change in the fiber type distribution following treatment (data not shown).

Example 5: Myostatin Inhibition Improves Muscle Function in SMA Mice Treated with Splice Corrector To assess the ability of SRK-015 to improve muscle function in SMA, a variant of a pharmacological model of SMA in which the severity of the disease can be moderated through administration of varying amounts of the small molecule SMN2 splice modulator SMN-C1 was used (17, 26). The foundation of this model is the Δ7 mouse model of severe SMA. This mouse, which lacks the sole endogenous murine SMN gene, expresses two copies of human SMN2 as well as two copies of SMN lacking exon 7 (Smn−/−; hSMN2; SMNΔ7). Due to the severity of disease in this model, the median survival of this mouse is 13 days, which is an insufficient amount of time to assess efficacy of potential therapeutic agents (70). By administering a low dose (0.1 mg/kg/day) of SMN-C1 from birth to Δ7 mice, survival is extended such that 70% of treated mice survive to post-natal day (PND) 52, although disease severity is still high. Treatment with a high dose of SMN-C1, 3 mg/kg/day, results in a mild form of SMA, with the mice appearing largely healthy and displaying only modest deficits in body weight and function. An intermediate model of severity can be achieved by administering Δ7 mice with 0.1 mg/kg/day of SMN-C1 for the first 24 days after birth, followed by a shift to 3 mg/kg/day thereafter (low-high treatment). In terms of body weight and muscle function, the phenotype of these low-high treated mice is approximately half-way between the low dose and high dose phenotype (17, 26, 71). The low-high SMN-C1 paradigm is also useful for assessing the therapeutic potential of treatments in combination with SMN2 splice modulators, as this mimics severe SMA patients who, once diagnosed, begin treatment with a splice corrector (i.e. nusinersen) months or years after birth. Beginning treatment with a second therapeutic concurrent with high dose SMN-C1 allows the effect of combinations therapy to be determined.

In order to assess the efficacy of inhibition of myostatin activation in combination with SMN2 splice correction, Δ7 mice were on a low-high SMN-C1 regiment were administered vehicle or weekly doses of 20 mg/kg muSRK-015P, beginning at PND24, concurrent with the switch to high dose SMN-C1. Mice were treated for an additional 4 weeks with 3 mg/kg/day SMN-C1 and muSRK-015P or vehicle. Untreated wild-type mice were included as a control. At study termination muscle weights, fiber cross-sectional area, and nerve evoked function of the plantarflexor muscle group and the masseter were assessed. In the Δ7 mouse, the masseter is a severely affected muscle while the gastrocnemius is relatively spared (7).

Figure 4:
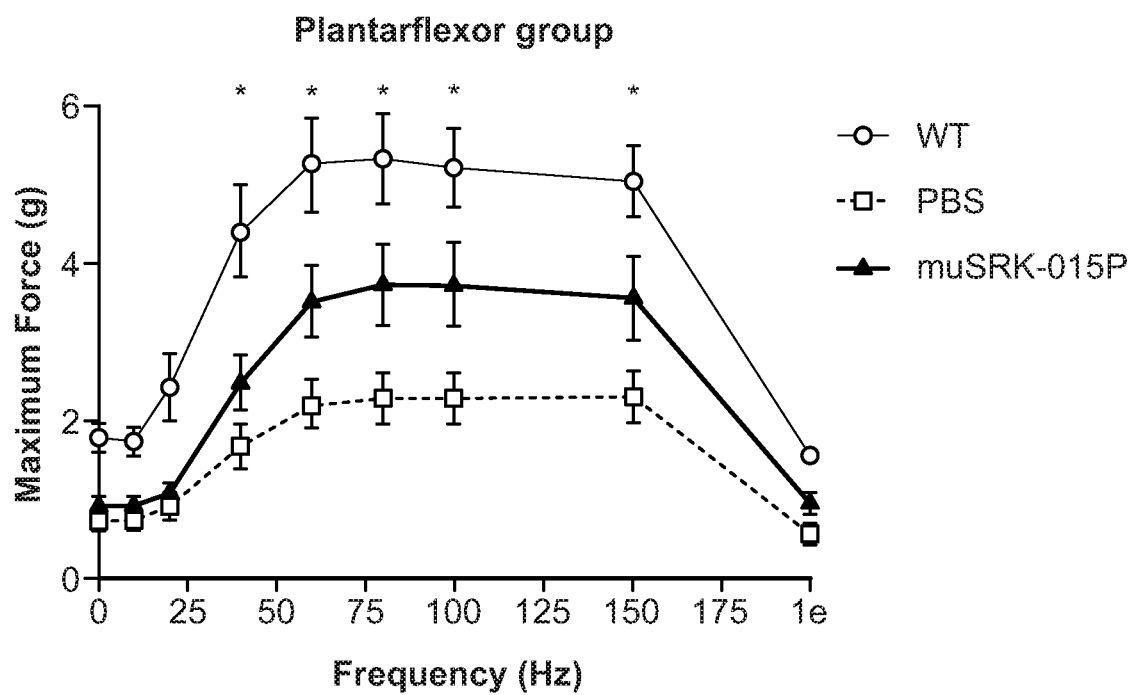
FIG. 4 provides a graph showing effects of muSRK-015P on maximum force of the plantarflexor group (gastrocnemius, soleus, and plantaris muscles) in SMN corrector-treated Δ7 SMA mice and wild type mice.
Figure 5A:
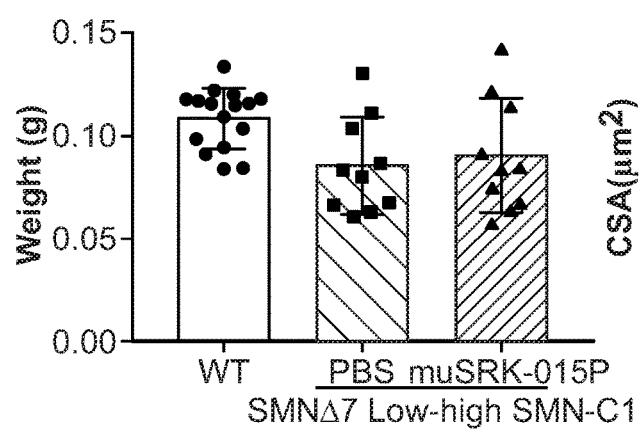
FIGS. 5A-5C provide three graphs showing effects of muSRK-015P on (FIG. 5A) muscle weight.
Figure 5B:
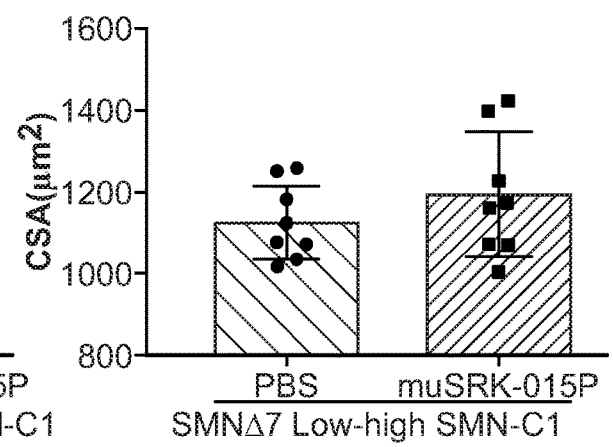
Figure 5C:
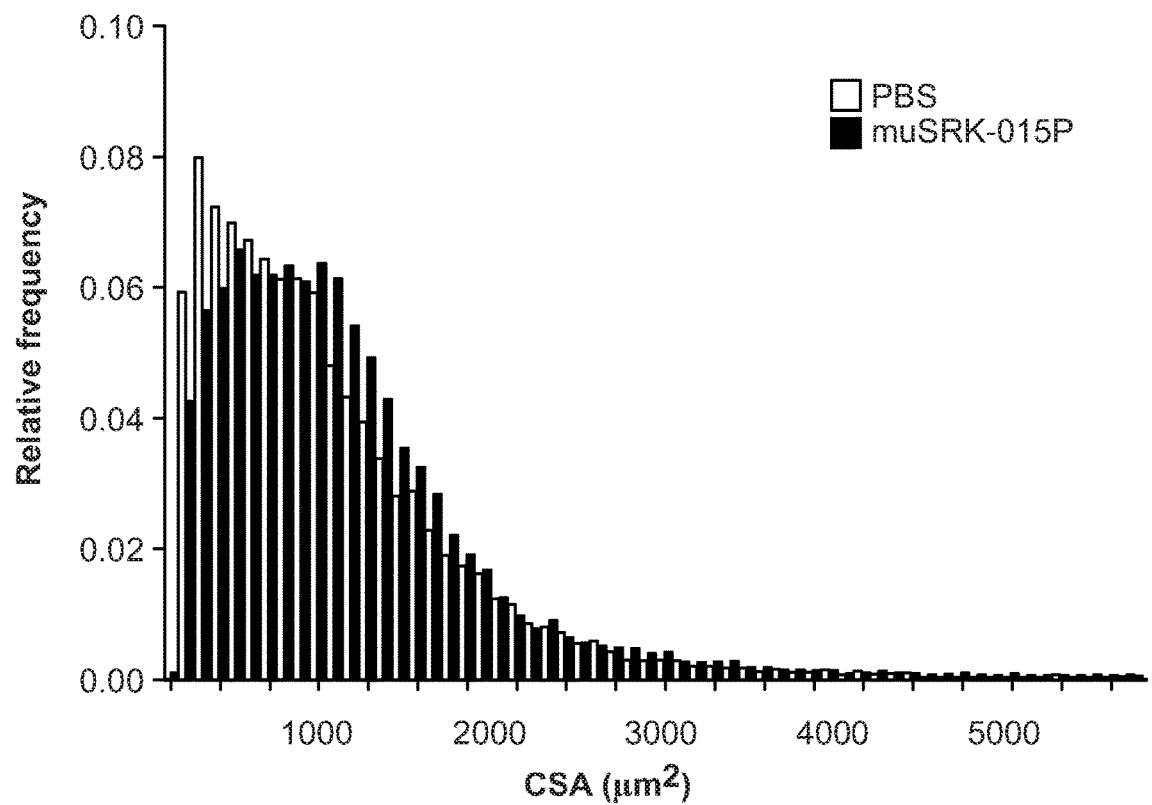

While muSRK-015P did not improve masseter function, muSRK-015P treatment resulted in a significant 60% increase in maximum torque generation by the plantarflexor muscle group (FIG. 4A, FIG. 4B). Interestingly, significant increases in the mass of the gastrocnemius muscle or the mean cross sectional area of the plantarflexor group were not observed (FIG. 5A, FIG. 5B). However, a shift in the frequency distribution of myofiber cross sectional area was observed, in that animals treated with muSRK-015P have more myofibers between 1000-2000 $\mu m^2$, while the vehicle treated mice have a greater number of myofibers smaller than 1000 $\mu m^2$ (FIG. 5C). It is unclear why muscle weight was not increased with treatment in this model while force generation was significantly increased. To date all animal studies conducted with this molecule have resulted in significant increases in muscle weight, and there were no published reports of myostatin inhibition improving muscle function in the absence of mass increases. One possibility is that treatment with muSRK-015P may improve the health and/or quality of the muscle such that expression of neurotrophic factors is increased, and motor neuron survival is improved. Expression of multiple neurotrophic factors by muscle (i.e. HGF, neurotrophin-4, and GDNF) has been shown to support motor neuron survival and outgrowth (73-75).

Figure 6A:
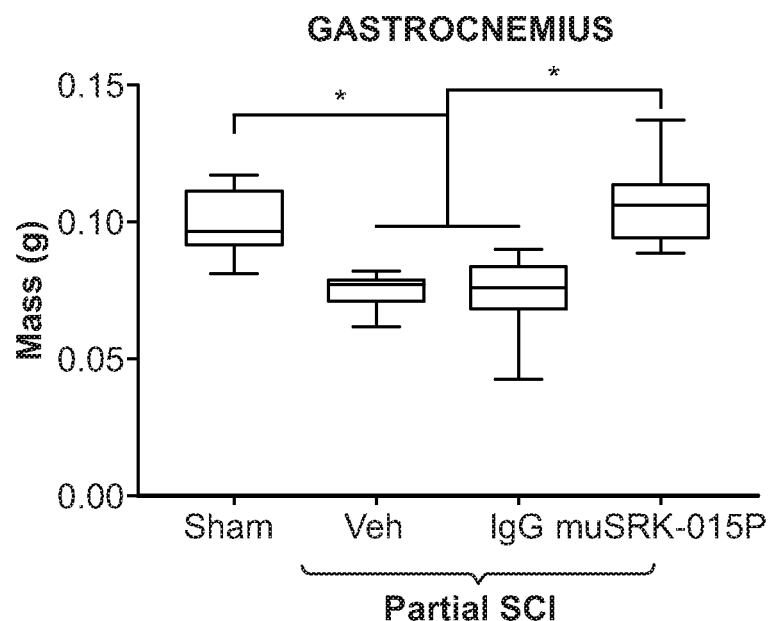
FIGS. 6A-6B provide two graphs showing effects of muSRK-015P on (FIG. 6A) GA muscle mass.
Figure 6B:
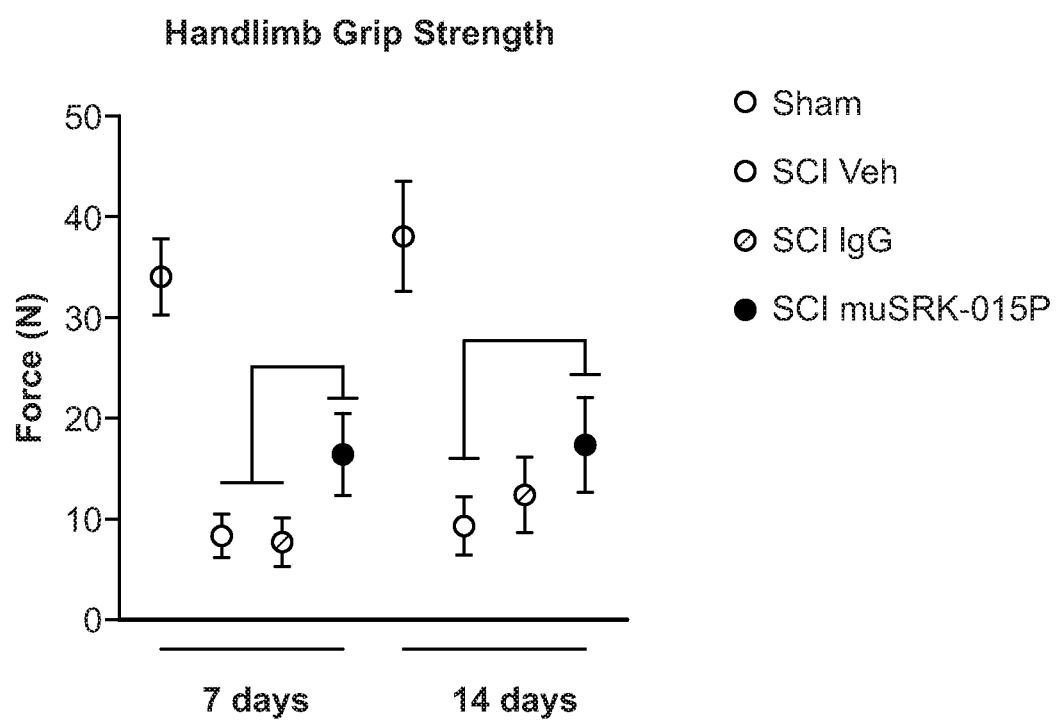

Example 6: Benefits of Myostatin Inhibition Require Sufficient Muscle Innervation The differential efficacy of muSRK-015P on the gastrocnemius (which constitutes the bulk of the plantarflexor group) and the masseter may be attributed to two facets of SMA disease pathology. First, it is known and also demonstrated here that myostatin inhibition preferentially results in hypertrophy of fast glycolytic muscle fibers (Type IIB in the mouse) ((76, 77) and FIG. 3E). While the mouse gastrocnemius muscle consists primarily of Type IIB fibers (~75%), the masseter has significantly fewer, between 10 and 25% (78, 79). Secondly, as a severely affected muscle, the denervation of the masseter is more extensive than that of the gastrocnemius (7). To be effective, myostatin inhibition is dependent on sufficient muscle innervation; treatment with myostatin inhibitors has no effect on muscle below the level of injury in a model of complete spinal cord injury (80). In contrast, significant preservation of muscle mass and function below the level of injury in a contusion model of spinal cord injury was observed using muSRK-015P, in which denervation was only partial (FIG. 6). In this study, female 8 week old C57BL/6 (n=6 to 8) were subjected to laminectomy at thoracic level 9 (T9) followed by severe (65 kDyne) spinal cord contusion using the infinite Horizon Compactor Device. Sham control animals were subjected to laminectomy only. Immediately following injury, mice were administered vehicle (PBS), IgG control, or muSRK-015P at 40 mg/kg. It is noted that PBS and IgG controls are shown to be equivalent in multiple models (data not shown). Treatments were administered weekly, and the study was terminated on day 14. (FIG. 6A) Mice subjected to partial severe SCI displayed significant atrophy of the hindlimb muscles, while animals administered muSRK-015P were protected from this atrophy. P<0.05. (FIG. 6B) Muscle function tests were performed 7 and 14 days following SCI. Hindlimb grip strength was assessed using a digital force gauge. While vehicle and IgG treated mice displayed a profound loss of strength, mice administered muSRK-015P retained a significant degree of strength in limbs below the level of the lesion. P<0.001. Data are presented as mean ±SEM and were analyzed by one-way ANOVA followed by Tukey's post-hoc comparison.

Importantly, SMA patients treated with nusinersen have shown improvements in compound muscle action potential (CMAP) amplitudes. This measure would normally only decline in these patients, indicating that, with SMN2 splice modulation, sufficient muscle innervation is maintained, in at least some muscles, for myostatin inhibition to be effective (25).

The preclinical results, in particular the pronounced effects of muSRK-015P on improving muscle function in two models of partial denervation (SMA and incomplete spinal cord injury), provided support for the potential of SRK-015 to significantly restore muscle function to SMA patients. Treatment with SRK-015 can be in combination with splice correctors or as a monotherapy in patients with milder forms of disease (i.e. Type III SMA) where sufficient innervation remains.

Example 7: Target Engagement in SMNΔ7 Mice

SMNΔ7 mice were treated with 0.1 mg/kg/day SMN-C1, an SMN splice modulator, from birth to post-natal day (PND) 24. At PND24 mice were switched to a high dose of SMN-C1 (3 mg/kg/day) and treatment begun with vehicle or 20 mg/kg/week muSRK-015P. Mice were administered antibody weekly for four weeks. At study termination, serum and TA muscles were collected and analyzed for target engagement by fluorescent western blot. Samples from 3-5 animals per groups were used in these analyses.

Figure 7A:
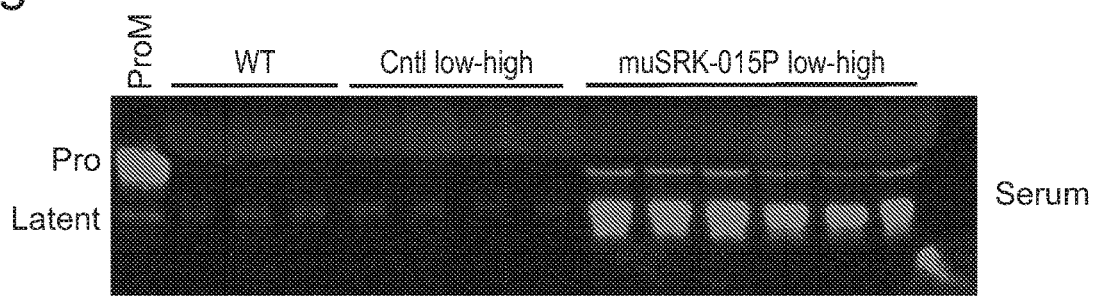
FIGS. 7A-7D present target engagement analyses of serum and muscle from SMNΔ7 mice. Immunoblot to measure latent myostatin in circulation following four weeks of treatment with muSRK-015P is shown in FIG. 7A. Immunoblot in FIG. 7B shows target engagement in muscle.
Figure 7B:
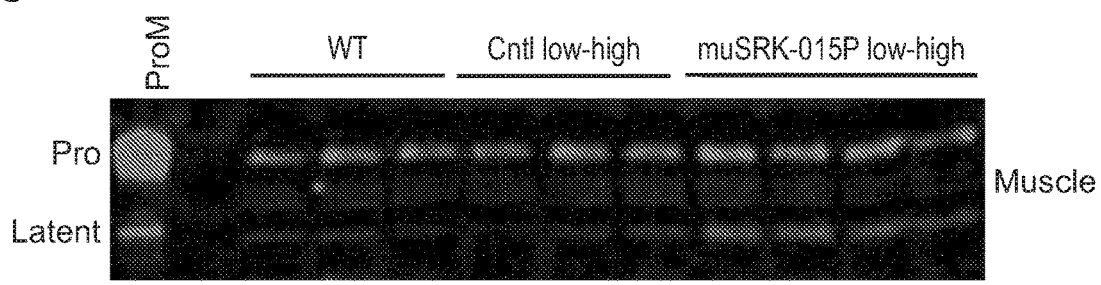
Figure 7C:
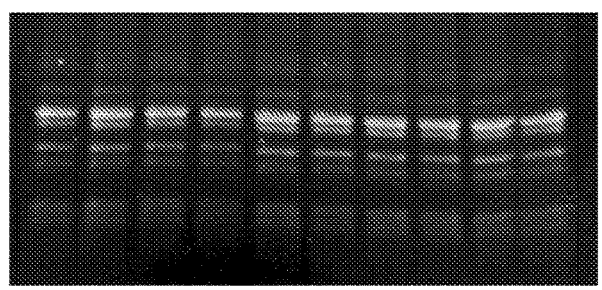
Figure 7D:
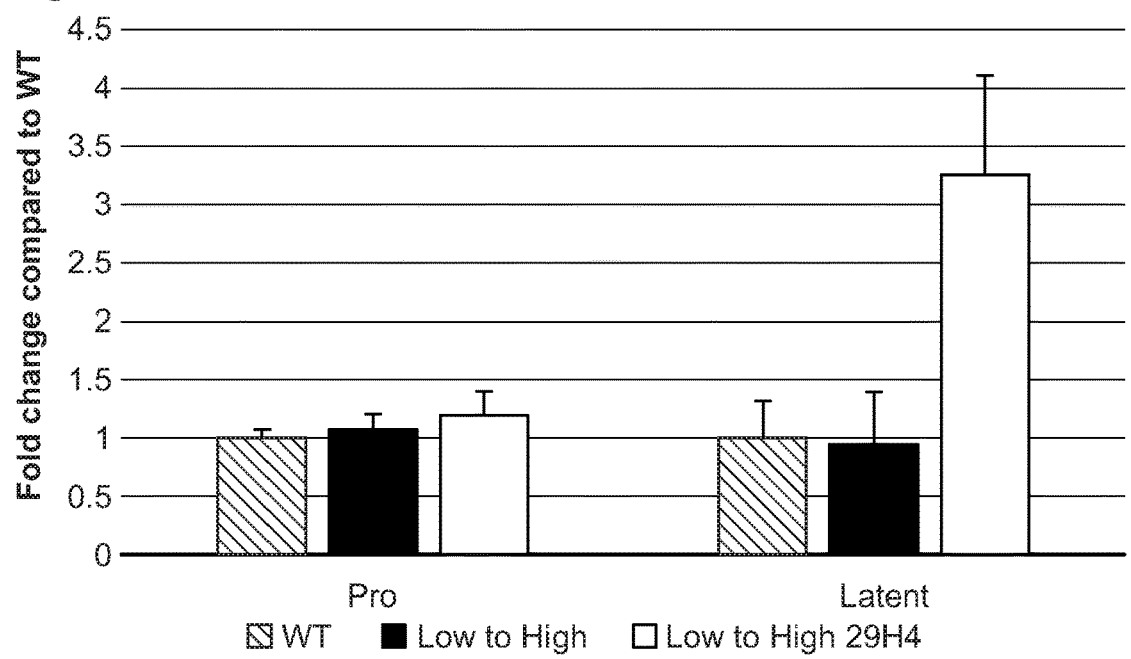

Target engagement was observed in SMNΔ7 mice treated with muSRK-015P. Binding to muSRK-015P results in accumulation of latent myostatin as the bound target assumes the half-life of the antibody and accumulates in circulation and in the target tissues. We developed a western blot assay in which an antibody to the myostatin pro-domain is used to assess latent myostatin levels in serum and muscle following antibody administration. We have previously determined the specificity of the antibody using samples from myostatin knockout animals. As indicated, antibody dosing began at post-natal day 24 concurrently with a switch from low dose to high dose of the SMN-C1 corrector. After four weeks of dosing, serum and tibialis anterior muscle was collected, and target engagement assessed. As shown in FIG. 7, results demonstrated engagement of latent myostatin in circulation (indicated by target accumulation upon antibody binding) following four weeks of treatment with muSRK-015P (see immunoblots in FIG. 7A). Lane 1 is recombinant purified proMyostatin, which contains a small amount of latent myostatin. Similarly, FIG. 7B shows target engagement in muscle. Accumulation of latent myostatin is observed in muscle from muSRK-015P treated mice after four weeks of treatment, indicating binding by the antibody. Lane 1 is recombinant pro/latent myostatin. To allow normalization across lanes, samples were run on TGX stain free gels to allow visualization and quantitation of total lane protein content upon UV imaging (FIG. 7C). Quantitation of the latent myostatin signal in muscle show a 3-fold target accumulation in the muSRK-015P group, demonstrating target engagement. The latent myostatin signal in each lane was normalized to the total protein content of that lane and compared to the latent myostatin present in WT mice (FIG. 7D).

Example 8: Pharmacokinetics and Pharmacodynamics of SRK-015 in Scid Mice

Male scid mice were administered a single 5 mg/kg IV dose of SRK-015. Separate cohorts of mice were sacrificed 4 hours, 2, 8, 15, 22, 29, and 56 days post dose, and serum and TA muscles collected for PK and target engagement assays. N=4 or 8 per group. PK analysis of SRK-015 is shown in FIG. 8A. SRK-015 levels were determined from serum samples taken at the indicated times after dosing. Analysis was performed using an anti-human IgG ELISA. The half-life of SRK-015 in scid mice at 5 mg/kg was ~20.3 days.

Figure 8B:
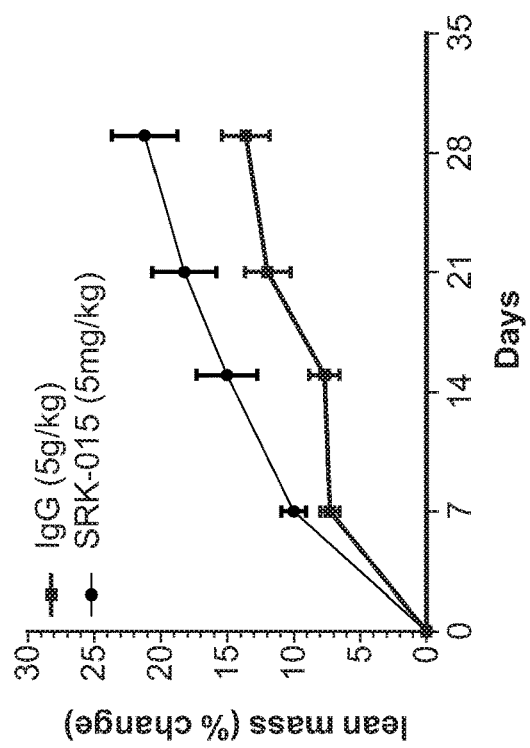
FIGS. 8A-8C provide PK and PD data for SRK-015 in scid mice. PK analysis of SRK-015 is shown in FIG. 8A. Lean mass was measured with qNMR at the indicated timepoints after dosing and increase in lean mass relative to IgG control is shown in FIG. 8B. Target engagement in serum and muscle of SRK-015 was assessed by analyzing levels of latent myostatin in serum and muscle using western blot as shown in FIG. 8C.
Figure 8A:
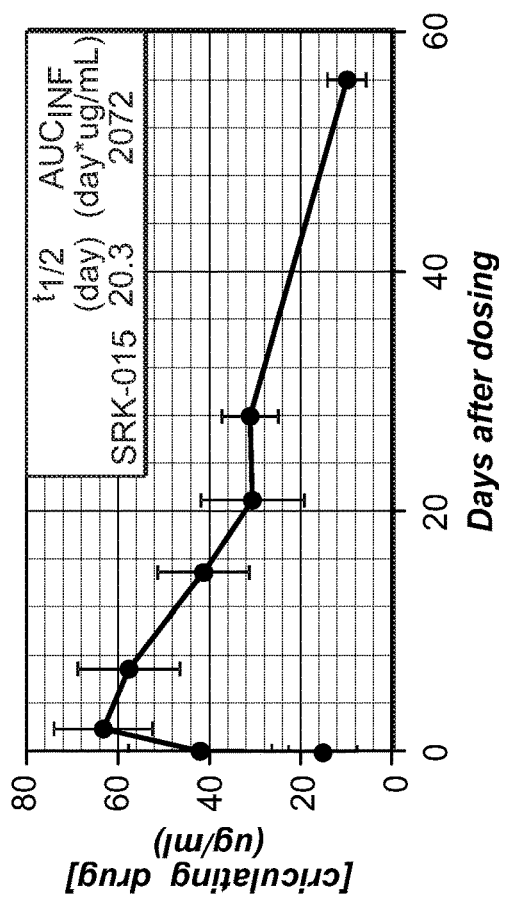
Figure 8C:
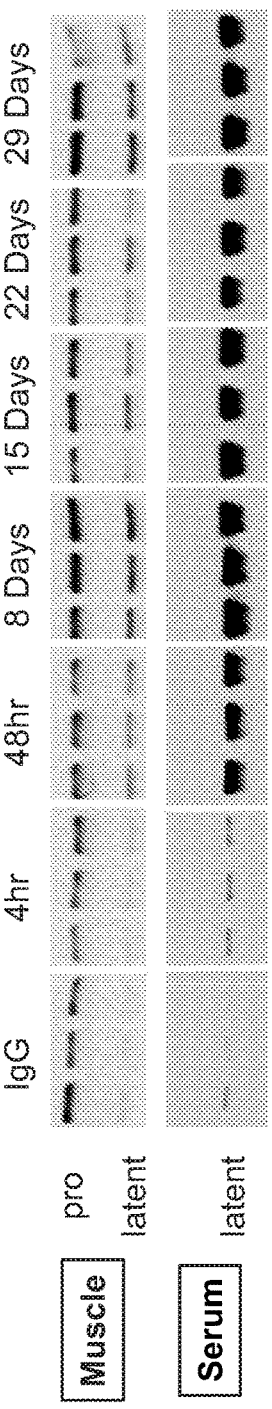

Correspondingly, as shown in FIG. 8B, administration of a single 5 mg/kg dose in these animals resulted in significant increase in lean mass relative to IgG control. Lean mass was measured with qNMR at the indicated timepoints after dosing. Additionally, SRK-015 displays extended target engagement in serum and muscle following a single 5 mg/kg dose (see FIG. 8C). By 56 days post-dosing, target engagement was no longer observed as the majority of SRK-015 has been cleared at this time point (data not shown). Target engagement was assessed by analyzing levels of latent myostatin in serum and muscle using western blot. Binding to SRK-015 results in accumulation of latent myostatin as the bound target assumes the half-life of the antibody and accumulates in circulation and in the target tissues. An antibody to the myostatin pro-domain was used in this assay, after determining the specificity of the antibody using samples from myostatin knockout animals Significant target engagement occurs within two days in the muscle, within four hours in circulation, and is sustained out to 29 days post dose. Samples from three mice from each cohort were analyzed.

Figure 9B:
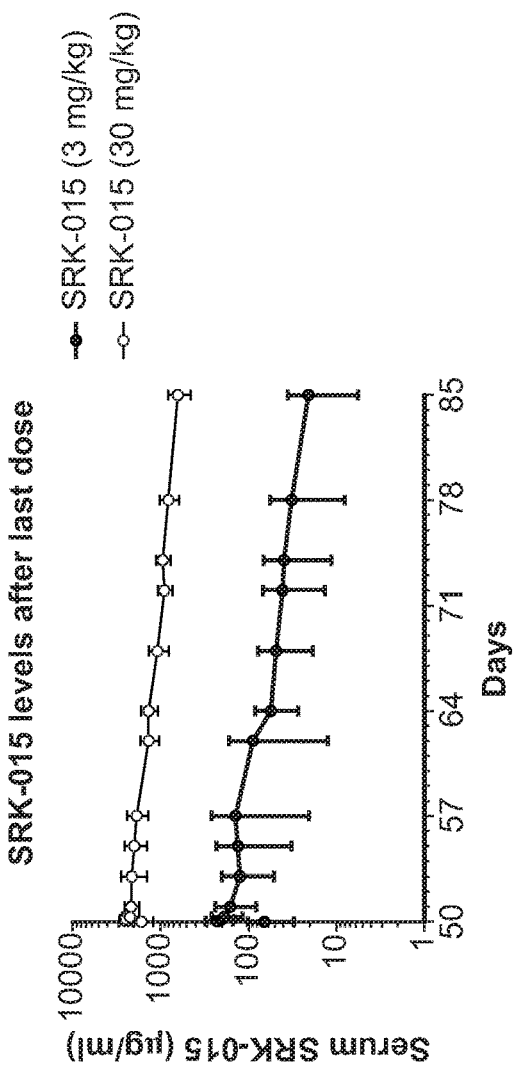
FIGS. 9A-9B provide SRK-015 PK data in cynomolgus monkeys. SRK-015 concentrations were assessed by ELISA.
Figure 9A:
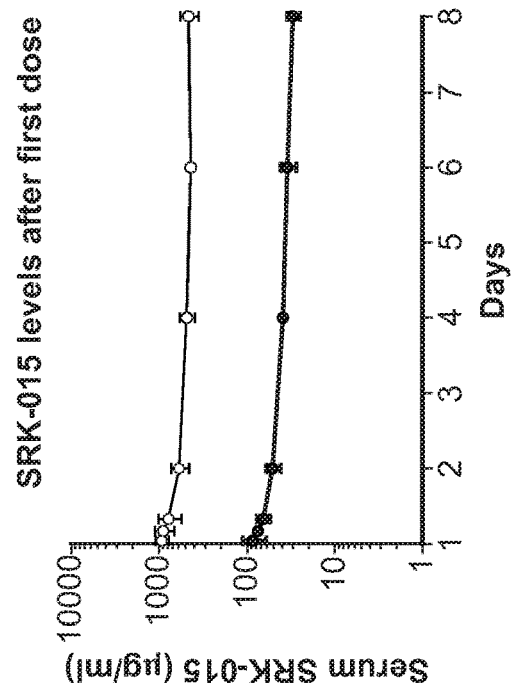

Example 9. Pharmacokinetics and Pharmacodynamics of SRK-015 in Cynomolgus Monkeys SRK-015 PK properties were also determined in cynomolgus monkeys. Two- to three-year old male animals (average age 34 months) were administered weekly doses of 3 mg/kg or 30 mg/kg SRK-015 for 8 weeks. Following the last dose, animals were followed for an additional five weeks in the absence of drug administration. Samples from this post-dosing period were used to calculate PK parameters. FIG. 9A shows SRK-015 concentrations during the week following the first antibody dose. Antibody levels were assessed by ELISA. FIG. 9B shows SRK-015 concentrations during the final five weeks of the study following the last of eight weekly antibody doses, demonstrating saturation at the high dose.

Pharmacokinetics data obtained for SRK-015 in cynomolgus monkeys are summarized in Table 4 below:

TABLE 4

PK parameters of SRK-015 in cynomolgus monkeys. Parameters were determined using WinNonlin software.

| Dose | $T_{1/2}$ (hour) | $T_{max}$ (hour) | $C_{max}$ (ng/ml) | $AUC_{last}$ (hr■ng/ml) |
|---|---|---|---|---|
| 3 mg/kg | 12.4 | 51 | 243 | 60799 |
| 30 mg/kg | 22.2 | 15 | 2648 | 1070638 |

Figure 10B:
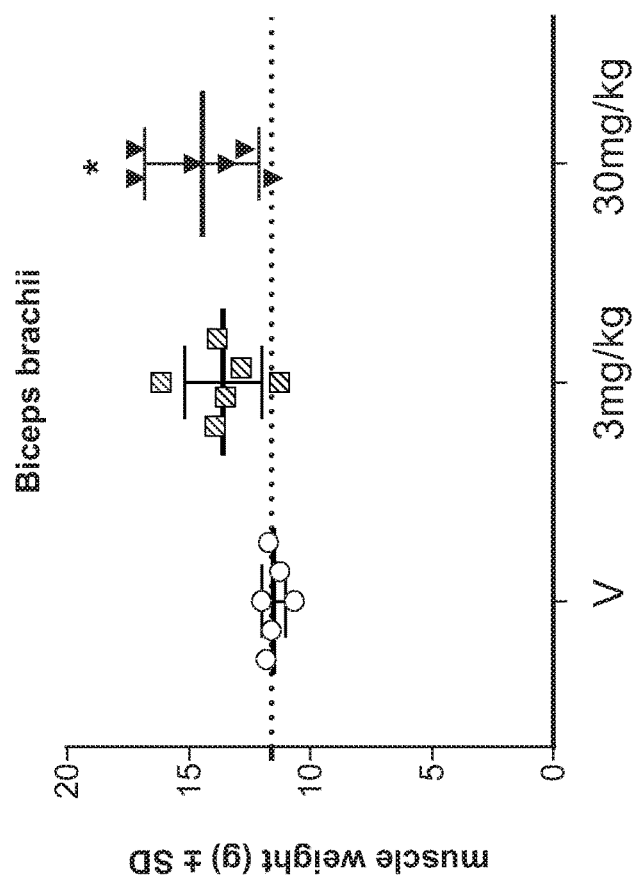
FIGS. 10A-10D provide data showing that SRK-015 is pharmacologically efficacious at multiple doses in cynomolgus monkeys. Muscle weights were determined five weeks after the last dose of SRK-015 in cynomolgus monkeys.
Figure 10A:
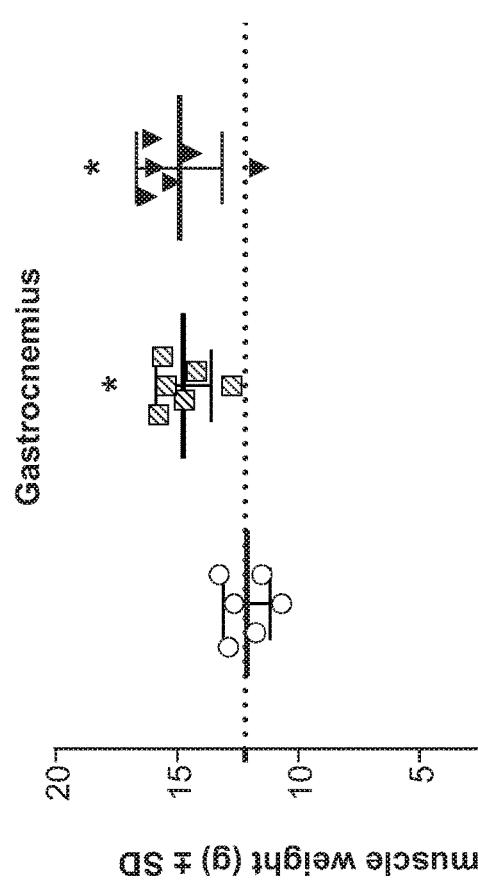
Figure 10C:
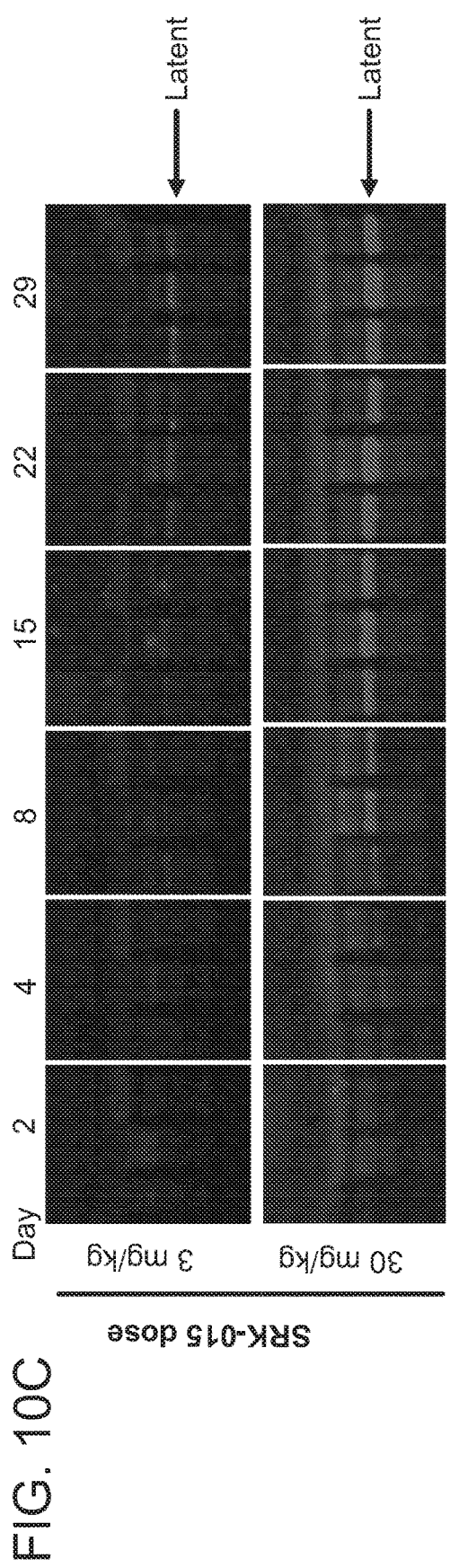
Figure 10D:
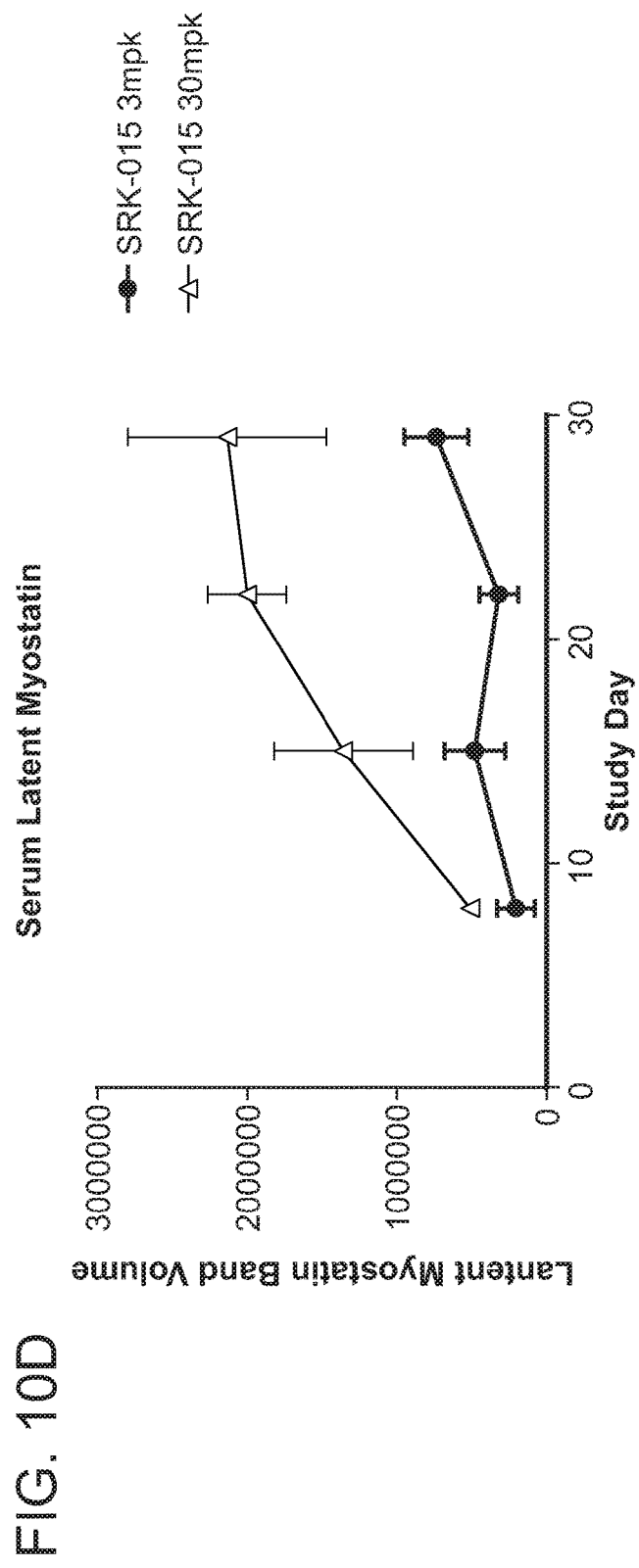

At study termination animals were sacrificed five weeks after the last dose as described in above and muscle weights were determined. Gastrocnemius and Biceps brachii muscles (FIG. 10A and FIG. 10B, respectively) show increased mass following SRK-015 treatment. Gastrocnemius weights increased 21% in the 3 mg/kg groups, and 23% in the 30 mg/kg groups relative to vehicle control. * indicates statistically significant difference from vehicle by one-way ANOVA; P<0.007. Biceps brachii weights increased 18% in the 3 mg/kg groups, and 25% in the 30 mg/kg group relative to vehicle control. * indicates statistically significant difference from vehicle by one-way ANOVA; P<0.02. As shown in FIGS. 10C and 10D, SRK-015 engaged latent myostatin at both doses tested. Time-course of target engagement in serum from monkeys administered 3 mg/kg or 30 mg/kg weekly is shown in FIG. 10C. Serum samples were collected at the indicated study day and analyzed by semi-quantitative western blot analysis. Accumulation of latent myostatin, indicative of SRK-015 binding, is evident by day 8. Target continues to accumulate as additional doses are administered. Latent myostatin levels were quantified as described in Example 7 above. The effects of SRK-015 on muscle weight indicate that even at lower end of dosage (e.g., 3 mg/kg/week) SRK-015 is at or near the level of target engagement necessary for maximal efficacy.

Example 10: Muscle Performance in SMNΔ7 Mice Treated with a Fully Therapeutic Dose of SMN-CJ from Birth SMNΔ7 mice were administered 3 mg/kg/day of the SMN splice modulator SMN-C1 starting at post-natal day (PND)

1. Treatment with this dose of SMN-C1 resulted in significant correction of disease and was intended to mimic mild presentations of SMA, such as ambulatory Type III or Type IV SMA. At PND24 mice began treatment with muSRK-015P (20 mg/kg/week). A control group was administered PBS. At PND52 mice muscle function was assessed in the plantarflexor muscle group (gastrocnemius, soleus, and plantaris muscles) and in the masseter. Individual muscles were isolated and weighed (FIGS. 11A and 11B) following euthanasia. Untreated wild-type mice of the same genetic background were used as controls.

Muscle performance was measured using a 305C muscle lever system (Aurora Scientific Inc., Aurora, CAN) as described above.

Figure 11A:
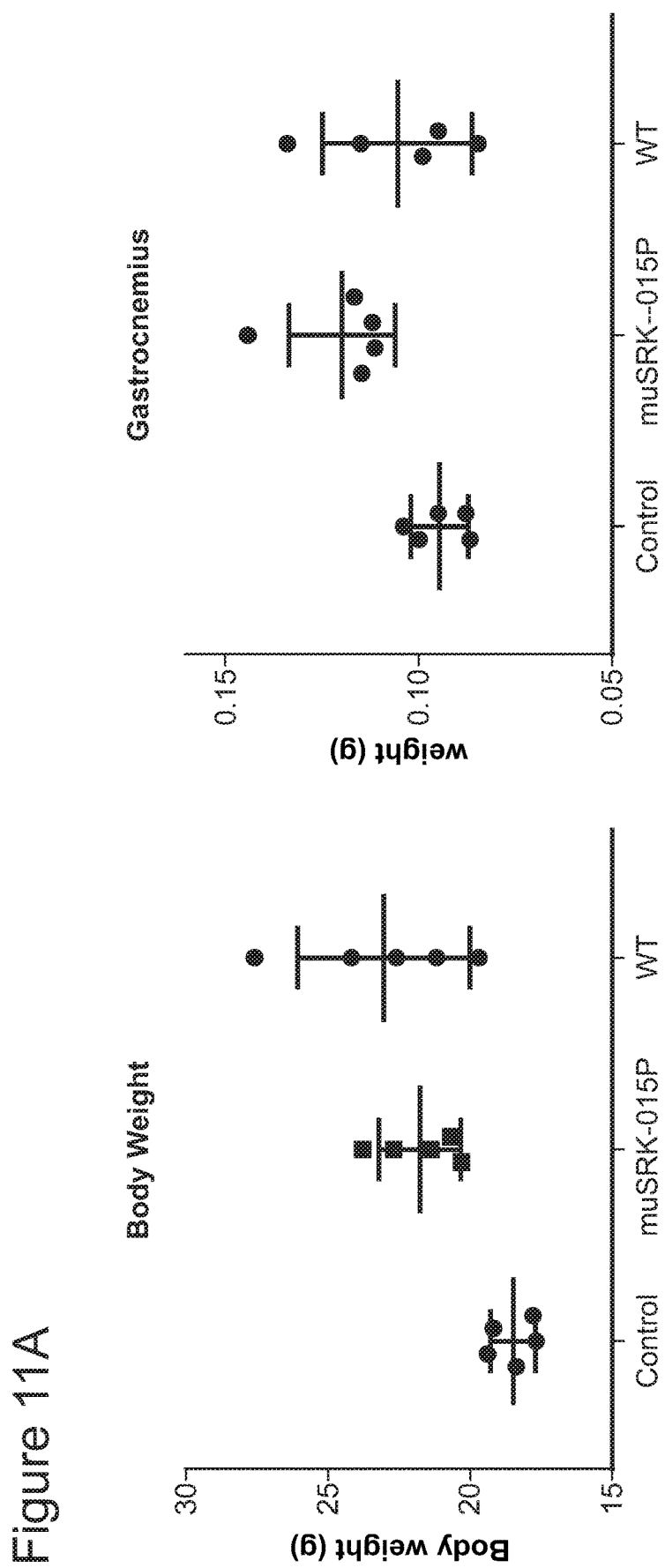
FIGS. 11A-11B provide data showing Muscle performance in SMNΔ7 mice treated with a fully therapeutic dose of SMN-C1 from birth. Following four weeks of treatment with muSRK-015P, increase in body weight relative to PBS control animals (FIG. 11A) and increase in mass of gastrocnemius (FIG. 11A) were measured. Performance of plantarflexor and masseter muscles were measured using a 305C muscle lever system (FIG. 11B).
Figure 11B:
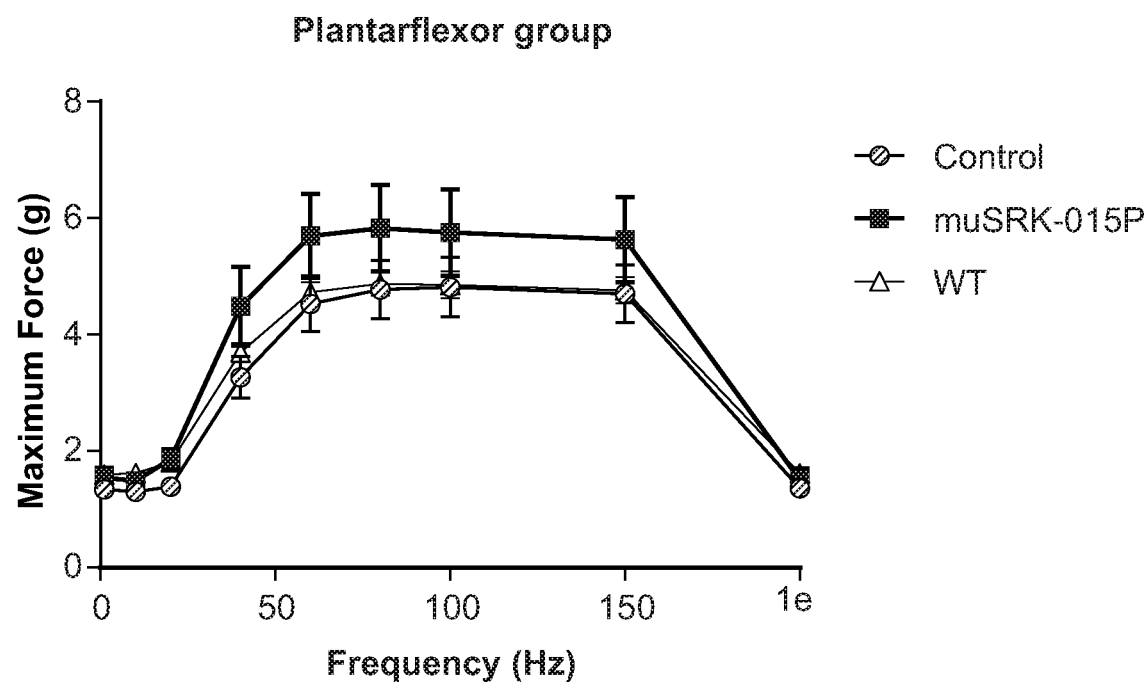

Following four weeks of treatment with muSRK-015P, SMNΔ7 mice displayed a 17.7% increase in body weight relative to PBS control animals (P=0.0021) (FIG. 11A). Treatment with muSRK-015P also resulted in increased mass of multiple hindlimb muscles, including the gastrocnemius (26.5% increase, P=0.0071) (FIG. 11A). This increase in mass was mirrored in functional gains; mice treated with muSRK-015P displayed a 22-37% improvement in force generation of the plantarflexor group over a range of physiologically relevant frequencies (40-80 Hz) (FIG. 11B). No effects of antibody treatment were observed in the masseter, a muscle which is more severely affected in this model than the gastrocnemius.

REFERENCES

1. T. Awano, J. K. Kim, U. R. Monani, Spinal muscular atrophy: journeying from bench to bedside. Neurotherapeutics 11, 786-795 (2014).
2. U. R. Monani, Spinal muscular atrophy: a deficiency in a ubiquitous protein; a motor neuron-specific disease. Neuron 48, 885-896 (2005).
3. L. A. Nash, J. K. Burns, J. W. Chardon, R. Kothary, R. J. Parks, Spinal Muscular Atrophy: More than a Disease of Motor Neurons? Curr Mol Med, (2016).
4. R. Finkel, E. Bertini, F. Muntoni, E. Mercuri, E. S. W. S. Group, 209th ENMC International Workshop: Outcome Measures and Clinical Trial Readiness in Spinal Muscular Atrophy 7-9 Nov. 2014, Heemskerk, The Netherlands. Neuromuscul Disord 25, 593-602 (2015).
5. S. Lefebvre et al., Identification and characterization of a spinal muscular atrophy-determining gene. Cell 80, 155-165 (1995).
6. U. R. Monani et al., A single nucleotide difference that alters splicing patterns distinguishes the SMA gene SMN1 from the copy gene SMN2. Hum Mol Genet 8, 1177-1183 (1999).
7. K. K. Ling, R. M. Gibbs, Z. Feng, C. P. Ko, Severe neuromuscular denervation of clinically relevant muscles in a mouse model of spinal muscular atrophy. Hum Mol Genet 21, 185-195 (2012).
8. V. Le Verche, Sunshine, S. S., Hammers, D., Sweeney, H. L., and Paushkin, S., in Spinal Muscular Atrophy: Disease Mechanisms and Therapy, C. J. Sumner, Paushkin, S., and Ko., C-P, Ed. (Elsevier, 2017), chap. 21, pp. 341-356.
9. V. S. Dubowitz, C.; Oldfors, A.; Lane, R., in Muscle Biopsy, A Practical Approach: (Elsevier, 2013), chap. 9, pp. 235-249.
10. K. J. Swoboda et al., Natural history of denervation in SMA: relation to age, SMN2 copy number, and function. Ann Neurol 57, 704-712 (2005).
11. J. G. Boyer et al., Myogenic program dysregulation is contributory to disease pathogenesis in spinal muscular atrophy. Hum Mol Genet 23, 4249-4259 (2014).
12. M. Hayhurst, A. K. Wagner, M. Cerletti, A. J. Wagers, L. L. Rubin, A cell-autonomous defect in skeletal muscle satellite cells expressing low levels of survival of motor neuron protein. Dev Biol 368, 323-334 (2012).
13. C. Cifuentes-Diaz et al., Deletion of murine SMN exon 7 directed to skeletal muscle leads to severe muscular dystrophy. J Cell Biol 152, 1107-1114 (2001).
14. C. A. Mutsaers et al., Reversible molecular pathology of skeletal muscle in spinal muscular atrophy. Hum Mol Genet 20, 4334-4344 (2011).
15. M. A. Passini et al., CNS-targeted gene therapy improves survival and motor function in a mouse model of spinal muscular atrophy. J Clin Invest 120, 1253-1264 (2010).
16. A. N. Calder, E. J. Androphy, K. J. Hodgetts, Small Molecules in Development for the Treatment of Spinal Muscular Atrophy. J Med Chem 59, 10067-10083 (2016).
17. N. A. Naryshkin et al., Motor neuron disease. SMN2 splicing modifiers improve motor function and longevity in mice with spinal muscular atrophy. Science 345, 688-693 (2014).
18. J. Palacino et al., SMN2 splice modulators enhance U1-pre-mRNA association and rescue SMA mice. Nat Chem Biol 11, 511-517 (2015).
19. H. Ratni et al., Specific Correction of Alternative Survival Motor Neuron 2 Splicing by Small Molecules: Discovery of a Potential Novel Medicine To Treat Spinal Muscular Atrophy. J Med Chem 59, 6086-6100 (2016).
20. Y. Hua et al., Antisense correction of SMN2 splicing in the CNS rescues necrosis in a type III SMA mouse model. Genes Dev 24, 1634-1644 (2010).
21. Y. Hua et al., Peripheral SMN restoration is essential for long-term rescue of a severe spinal muscular atrophy mouse model. Nature 478, 123-126 (2011).
22. M. A. Passini et al., Antisense oligonucleotides delivered to the mouse CNS ameliorate symptoms of severe spinal muscular atrophy. Sci Transl Med 3, 72ra18 (2011).
23. C. A. Chiriboga et al., Results from a phase 1 study of nusinersen (ISIS-SMN(Rx)) in children with spinal muscular atrophy. Neurology 86, 890-897 (2016).
24. R. S. Finkel et al., Treatment of infantile-onset spinal muscular atrophy with nusinersen: a phase 2, open-label, dose-escalation study. Lancet 388, 3017-3026 (2016).
25. FDA, Nusinersen; Office of drug evaluation decisional memorandum (2016).
26. Z. Feng et al., Pharmacologically induced mouse model of adult spinal muscular atrophy to evaluate effectiveness of therapeutics after disease onset. Hum Mol Genet 25, 964-975 (2016).
27. A. M. Glanzman et al., Validation of the Expanded Hammersmith Functional Motor Scale in spinal muscular atrophy type II and III. J Child Neurol 26, 1499-1507 (2011).
28. P. Kaufmann et al., Observational study of spinal muscular atrophy type 2 and 3: functional outcomes over 1 year. Arch Neurol 68, 779-786 (2011).
29. A. C. McPherron, A. M. Lawler, S. J. Lee, Regulation of skeletal muscle mass in mice by a new TGF-beta superfamily member. Nature 387, 83-90 (1997).
30. S. J. Lee, A. C. McPherron, Regulation of myostatin activity and muscle growth. Proc Natl Acad Sci USA 98, 9306-9311 (2001).

31. E. Latres et al., Myostatin blockade with a fully human monoclonal antibody induces muscle hypertrophy and reverses muscle atrophy in young and aged mice. Skelet Muscle 5, 34 (2015).
32. R. C. Smith et al., Myostatin Neutralization Results in Preservation of Muscle Mass and Strength in Preclinical Models of Tumor-Induced Muscle Wasting. Mol Cancer Ther 14, 1661-1670 (2015).
33. J. Wang, X. Wang, W. Feng, Reloading Promotes Recovery of Disuse Muscle Loss by Inhibiting TGFbeta Pathway Activation in Rats After Hind Limb Suspension. Am J Phys Med Rehabil, (2016).
34. X. Zhou et al., Reversal of cancer cachexia and muscle wasting by ActRIIB antagonism leads to prolonged survival. Cell 142, 531-543 (2010).
35. A. C. McPherron, S. J. Lee, Double muscling in cattle due to mutations in the myostatin gene. Proc Natl Acad Sci USA 94, 12457-12461 (1997).
36. D. S. Mosher et al., A mutation in the myostatin gene increases muscle mass and enhances racing performance in heterozygote dogs. PLoS Genet 3, e79 (2007).
37. M. Schuelke et al., Myostatin mutation associated with gross muscle hypertrophy in a child. N Engl J Med 350, 2682-2688 (2004).
38. K. Garber, No longer going to waste. Nat Biotechnol 34, 458-461 (2016).
39. A. A. Amato et al., Treatment of sporadic inclusion body myositis with bimagrumab. Neurology 83, 2239-2246 (2014).
40. C. Becker et al., Myostatin antibody (LY2495655) in older weak fallers: a proof-of-concept, randomised, phase 2 trial. Lancet Diabetes Endocrinol 3, 948-957 (2015).
41. C. Campbell et al., Myostatin inhibitor ACE-031 treatment of ambulatory boys with Duchenne muscular dystrophy: Results of a randomized, placebo-controlled clinical trial. Muscle Nerve, (2016).
42. J. R. Mendell et al., A phase 1/2a follistatin gene therapy trial for becker muscular dystrophy. Mol Ther 23, 192-201 (2015).
43. K. R. Wagner et al., A phase I/IItrial of MYO-029 in adult subjects with muscular dystrophy. Ann Neurol 63, 561-571 (2008).
44. S. J. Lee et al., Regulation of muscle growth by multiple ligands signaling through activin type II receptors. Proc Natl Acad Sci USA 102, 18117-18122 (2005).
45. A. L. Schneyer et al., Differential antagonism of activin, myostatin and growth and differentiation factor 11 by wild-type and mutant follistatin. Endocrinology 149, 4589-4595 (2008).
46. M. A. Egerman et al., GDF11 Increases with Age and Inhibits Skeletal Muscle Regeneration. Cell Metab 22, 164-174 (2015).
47. A. F. Esquela, S. J. Lee, Regulation of metanephric kidney development by growth/differentiation factor 11. Dev Biol 257, 356-370 (2003).
48. D. W. Hammers et al., Supraphysiological levels of GDF11 induce striated muscle atrophy. EMBO Mol Med, (2017).
49. J. Kim et al., GDF11 controls the timing of progenitor cell competence in developing retina. Science 308, 1927-1930 (2005).
50. F. S. Loffredo et al., Growth differentiation factor 11 is a circulating factor that reverses age-related cardiac hypertrophy. Cell 153, 828-839 (2013).
51. A. C. McPherron, A. M. Lawler, S. J. Lee, Regulation of anterior/posterior patterning of the axial skeleton by growth/differentiation factor 11. Nat Genet 22, 260-264 (1999).
52. H. H. Wu et al., Autoregulation of neurogenesis by GDF11. Neuron 37, 197-207 (2003).
53. M. Sinha et al., Restoring systemic GDF11 levels reverses age-related dysfunction in mouse skeletal muscle. Science 344, 649-652 (2014).
54. R. Wijayarathna, D. M. de Kretser, Activins in reproductive biology and beyond. Hum Reprod Update 22, (2016).
55. E. Lach-Trifilieff et al., An antibody blocking activin type II receptors induces strong skeletal muscle hypertrophy and protects from atrophy. Mol Cell Biol 34, 606-618 (2014).
56. K. T. Murphy et al., Antibody-directed myostatin inhibition in 21-mo-old mice reveals novel roles for myostatin signaling in skeletal muscle structure and function. FASEB J 24, 4433-4442 (2010).
57. B. C. Yaden et al., Follistatin: a novel therapeutic for the improvement of muscle regeneration. J Pharmacol Exp Ther 349, 355-371 (2014).
58. P. Singh, H. Rong, T. Gordi, J. Bosley, I. Bhattacharya, Translational Pharmacokinetic/Pharmacodynamic Analysis of MYO-029 Antibody for Muscular Dystrophy. Clin Transl Sci 9, 302-310 (2016).
59. L. Woodhouse et al., A Phase 2 Randomized Study Investigating the Efficacy and Safety of Myostatin Antibody LY2495655 versus Placebo in Patients Undergoing Elective Total Hip Arthroplasty. J Frailty Aging 5, 62-70 (2016).
60. P. Balagopal, 0. E. Rooyackers, D. B. Adey, P. A. Ades, K. S. Nair, Effects of aging on in vivo synthesis of skeletal muscle myosin heavy-chain and sarcoplasmic protein in humans. Am J Physiol 273, E790-800 (1997).
61. S. W. Lamberts, A. W. van den Beld, A. J. van der Lely, The endocrinology of aging. Science 278, 419-424 (1997).
62. S. J. Lee, Extracellular Regulation of Myostatin: A Molecular Rheostat for Muscle Mass. Immunol Endocr Metab Agents Med Chem 10, 183-194 (2010).
63. N. M. Wolfman et al., Activation of latent myostatin by the BMP-1/tolloid family of metalloproteinases. Proc Natl Acad Sci USA 100, 15842-15846 (2003).
64. H. Q. Han, X. Zhou, W. E. Mitch, A. L. Goldberg, Myostatin/activin pathway antagonism: molecular basis and therapeutic potential. Int J Biochem Cell Biol 45, 2333-2347 (2013).
65. S. B. Anderson, A. L. Goldberg, M. Whitman, Identification of a novel pool of extracellular pro-myostatin in skeletal muscle. J Biol Chem 283, 7027-7035 (2008).
66. H. R. Bergen, 3rd et al., Myostatin as a mediator of sarcopenia versus homeostatic regulator of muscle mass: insights using a new mass spectrometry-based assay. Skelet Muscle 5, 21 (2015).
67. G. Sengle, R. N. Ono, T. Sasaki, L. Y. Sakai, Prodomains of transforming growth factor beta (TGFbeta) superfamily members specify different functions: extracellular matrix interactions and growth factor bioavailability. J Biol Chem 286, 5087-5099 (2011).
68. T. A. Zimmers et al., Induction of cachexia in mice by systemically administered myostatin. Science 296, 1486-1488 (2002).
69. J. R. Apgar et al., Beyond CDR-grafting: Structure-guided humanization of framework and CDR regions of an anti-myostatin antibody. MAbs 8, 1302-1318 (2016).

70. T. T. Le et al., SMNDelta7, the major product of the centromeric survival motor neuron (SMN2) gene, extends survival in mice with spinal muscular atrophy and associates with full-length SMN. Hum Mol Genet 14, 845-857 (2005).
71. X. Zhao et al., Pharmacokinetics, pharmacodynamics, and efficacy of a small-molecule SMN2 splicing modifier in mouse models of spinal muscular atrophy. Hum Mol Genet 25, 1885-1899 (2016).
72. M. Liu, D. W. Hammers, E. R. Barton, H. L. Sweeney, Activin Receptor Type IIB Inhibition Improves Muscle Phenotype and Function in a Mouse Model of Spinal Muscular Atrophy. PLoS One 11, e0166803 (2016).
73. H. Funakoshi et al., Muscle-derived neurotrophin-4 as an activity-dependent trophic signal for adult motor neurons. Science 268, 1495-1499 (1995).
74. C. E. Henderson et al., GDNF: a potent survival factor for motoneurons present in peripheral nerve and muscle. Science 266, 1062-1064 (1994).
75. Y. Yamamoto et al., Hepatocyte growth factor (HGF/SF) is a muscle-derived survival factor for a subpopulation of embryonic motoneurons. Development 124, 2903-2913 (1997).
76. J. Yang et al., Expression of myostatin pro domain results in muscular transgenic mice. Mol Reprod Dev 60, 351-361 (2001).
77. B. Zhao, R. J. Wall, J. Yang, Transgenic expression of myostatin propeptide prevents diet-induced obesity and insulin resistance. Biochem Biophys Res Commun 337, 248-255 (2005).
78. V. Augusto, Padovani, C. R., and Campos, G. E. R., Skeletal muscle fiber types in C57BL/6 mice. Braz. J. morphol. Sci 21, 89-94 (2004).
79. J. M. Eason, G. A. Schwartz, G. K. Pavlath, A. W. English, Sexually dimorphic expression of myosin heavy chains in the adult mouse masseter. J Appl Physiol (1985) 89, 251-258 (2000).
80. Z. A. Graham et al., A Soluble Activin Receptor IIB Fails to Prevent Muscle Atrophy in a Mouse Model of Spinal Cord Injury. J Neurotrauma 33, 1128-1135 (2016).

The various features and embodiments of the present invention, referred to in individual sections above apply, as appropriate, to other sections, mutatis mutandis. Consequently features specified in one section may be combined with features specified in other sections, as appropriate.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating a neuromuscular disease in a subject, the method comprising administering to the subject a myostatin inhibitor and a neuronal corrector therapy in amounts effective to treat the neuromuscular disease, wherein:
  i) the neuromuscular disease affects a target muscle that is in an anabolic state;
  ii) the subject has impaired neurological signaling between a motor neuron and a target muscle, wherein the target muscle has retained or regained at least partial functional innervation by the motor neuron; and
  iii) the neuromuscular disease affects a target muscle that is enriched with type II fibers;
  wherein the subject receives the myostatin inhibitor and the neuronal corrector therapy within six months of one another;
  wherein the neuronal corrector therapy comprises an agent capable of correcting a neuronal defect in the motor neuron; and
  wherein the neuromuscular disease is spinal muscular atrophy (SMA).

2. The method of claim 1, wherein the SMA is type I SMA, type II SMA, or type III SMA.

3. The method of claim 1, wherein the subject is a pediatric subject or a young adult who is still growing and anabolically active.

4. The method of claim 1, wherein the myostatin inhibitor inhibits cleavage of a myostatin prodomain, inhibits release of a mature myostatin growth factor, and/or inhibits activation of a pro or latent myostatin to a mature myostatin.

5. The method of claim 1, wherein the myostatin inhibitor is administered in an amount effective to:
  a) delay or alleviate muscle atrophy;
  b) delay loss of α-motor neurons;
  c) prevent or delay expression of immature muscle markers;
  d) prevent, alleviate, or delay intramuscular fat deposits characterized by fatty replacement of muscle tissue;
  e) increase an Expanded Hammersmith Functional Motor Scale score by ≥1 points as compared to untreated control, or, by ≥1 points from baseline measured prior to treatment;

f) delay progressive decrease of an Expanded Hammersmith Functional Motor Scale over a period of 12 months, 24 months, or 36 months;

g) increase a CHOP INTEND score by ≥1 points as compared to untreated control; and/or h) increase a MFM-32 score by at least 1 points as compared to untreated control.

6. The method of claim 1, wherein the neuronal corrector therapy comprises an SMN corrector and/or an anabolic stimulator.

7. The method of claim 1, wherein the neuronal defect in the motor neuron is a genetic defect.

8. A method of treating spinal muscular atrophy (SMA) in a subject, the method comprising:
(i) selecting a subject, wherein the subject has SMA and is a pediatric subject or a young adult who is still growing and anabolically active; and
(ii) administering to the subject a selective myostatin inhibitor and an SMN corrector therapy in amounts effective to treat SMA.

9. The method of claim 8, wherein the SMA is type I SMA, type II SMA, or type III SMA.

10. The method of claim 8, wherein the myostatin inhibitor and the SMN corrector therapy are administered concurrently or within six months of one another.

11. The method of claim 8, wherein the SMN corrector therapy comprises a splice modifier.

12. The method of claim 8, wherein the SMN corrector therapy comprises an SMN gene replacement or gene therapy.

13. The method of claim 8, wherein the SMN corrector therapy comprises an SMN transcription enhancer.

14. The method of claim 8, wherein the SMN corrector therapy comprises an SMN protein translation enhancer.

15. The method of claim 8, wherein the SMN corrector therapy comprises an SMN protein stabilizer.

16. A method of treating spinal muscular atrophy (SMA) in a subject, the method comprising:
(i) selecting a subject, wherein the subject: (a) has SMA and is a pediatric subject or a young adult who is still growing and anabolically active; and (b) is on an SMN corrector therapy; and
(ii) administering to the subject a selective myostatin inhibitor in an amount effective to treat SMA.

17. The method of claim 16, wherein the SMA is type I SMA, type II SMA, or type III SMA.

18. The method of claim 16, wherein the SMN corrector therapy comprises a splice modifier.

19. The method of claim 16, wherein the SMN corrector therapy comprises an SMN gene replacement or gene therapy.

20. The method of claim 16, wherein the SMN corrector therapy comprises an SMN transcription enhancer.

21. The method of claim 16, wherein the SMN corrector therapy comprises an SMN protein translation enhancer.

22. The method of claim 16, wherein the SMN corrector therapy comprises an SMN protein stabilizer.

* * * * *

SEQUENCE LISTING

```
<160> NUMBER OF SEQ ID NOS: 116

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1

Ser Ser Tyr Gly Met His
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Gly Phe Thr Phe Ser Ser Tyr Gly Met His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Gly Phe Ala Phe Ser Ser Tyr Gly Met His
1               5                   10

<210> SEQ ID NO 4
<211> LENGTH: 17
<212> TYPE: PRT
<213> ORGANISM: Artificial Sequence
<220> FEATURE:
```

<223> OTHER INFORMATION: Synthetic

<400> SEQUENCE: 4

Val Ile Ser Tyr Asp Gly Ser Asn Lys Tyr Tyr Ala Asp Ser Val Lys
1               5                   10                  15

Gly

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Ile Ser Tyr Asp Gly Ser Asn
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic

<400> SEQUENCE: 6

Val Ile Ser Tyr Asp Gly Ser Ile Lys Tyr Tyr Ala Asp Ser Val Lys
1               5                   10                  15

Gly

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Ile Ser Tyr Asp Gly Ser Ile
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic

<400> SEQUENCE: 8

Val Ile Ser Tyr Asp Gly Asn Asn Lys Tyr Tyr Ala Asp Ser Val Lys
1               5                   10                  15

Gly

<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

Ile Ser Tyr Asp Gly Asn Asn
1               5

```
<210> SEQ ID NO 10
<211> LENGTH: 17
<212> TYPE: PRT
<213> ORGANISM: Artificial Sequence
<220> FEATURE:
<223> OTHER INFORMATION: Synthetic

<400> SEQUENCE: 10

Asp Leu Leu Val Arg Phe Leu Glu Trp Ser His Tyr Tyr Gly Met Asp
1               5                   10                  15
Val

<210> SEQ ID NO 11
<211> LENGTH: 17
<212> TYPE: PRT
<213> ORGANISM: Artificial Sequence
<220> FEATURE:
<223> OTHER INFORMATION: Synthetic

<400> SEQUENCE: 11

Asp Leu Leu Val Arg Phe Leu Glu Trp Ser His Lys Tyr Gly Met Asp
1               5                   10                  15
Val

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Ser Gly Ser Ser Ser Asn Ile Gly Ser Asn Thr Val His
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Ser Ser Asn Ile Gly Ser Asn Thr
1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic

<400> SEQUENCE: 14

Ser Gly Ser Thr Ser Asn Ile Gly Ser Asn Thr Val His
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Thr Ser Asn Ile Gly Ser Asn Thr
```

```
1               5
```

<210> SEQ ID NO 16
<211> LENGTH: 13
<212> TYPE: PRT
<213> ORGANISM: Artificial Sequence
<220> FEATURE:
<223> OTHER INFORMATION: Synthetic

<400> SEQUENCE: 16

```
Ser Gly Ser Ser Ser Asn Ile Gly Gly Asn Thr Val His
1               5                   10
```

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

```
Ser Ser Asn Ile Gly Gly Asn Thr
1               5
```

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

```
Ser Asp Asn Gln Arg Pro Ser
1               5
```

<210> SEQ ID NO 19
<211> LENGTH: 3
<212> TYPE: PRT
<213> ORGANISM: Artificial Sequence
<220> FEATURE:
<223> OTHER INFORMATION: Synthetic

<400> SEQUENCE: 19

```
Ser Asp Asn
1
```

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

```
Ser Asp Asp Gln Arg Pro Ser
1               5
```

<210> SEQ ID NO 21
<211> LENGTH: 3
<212> TYPE: PRT
<213> ORGANISM: Artificial Sequence
<220> FEATURE:
<223> OTHER INFORMATION: Synthetic

<400> SEQUENCE: 21

```
Ser Asp Asp
1
```

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Ala Ala Trp Asp Asp Ser Leu Asn Gly Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic

<400> SEQUENCE: 23

Ala Ala Trp Asp Glu Ser Leu Asn Gly Val
1               5                   10

<210> SEQ ID NO 24
<211> LENGTH: 126
<212> TYPE: PRT
<213> ORGANISM: Artificial Sequence
<220> FEATURE:
<223> OTHER INFORMATION: Synthetic

<400> SEQUENCE: 24

Gln Ile Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser
        115                 120                 125

<210> SEQ ID NO 25
<211> LENGTH: 126
<212> TYPE: PRT
<213> ORGANISM: Artificial Sequence
<220> FEATURE:
<223> OTHER INFORMATION: Synthetic

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser
            115                 120                 125

<210> SEQ ID NO 26
<211> LENGTH: 126
<212> TYPE: PRT
<213> ORGANISM: Artificial Sequence
<220> FEATURE:
<223> OTHER INFORMATION: Synthetic

<400> SEQUENCE: 26

Gln Ile Gln Leu Val Gln Ser Gly Gly Gly Val Val Gln Pro Gly Arg
 1               5                  10                  15

Ser Leu Arg Leu Ser Cys Ala Ala Ser Gly Phe Ala Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Ile Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
            115                 120                 125

<210> SEQ ID NO 27
<211> LENGTH: 126
<212> TYPE: PRT
<213> ORGANISM: Artificial Sequence
<220> FEATURE:
<223> OTHER INFORMATION: Synthetic

<400> SEQUENCE: 27

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ala Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Ile Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Lys Tyr Gly

```
            100                 105                 110
Met Asp Val Trp Gly Gln Gly Thr Thr Val Thr Val Ser Ser
        115                 120                 125

<210> SEQ ID NO 28
<211> LENGTH: 126
<212> TYPE: PRT
<213> ORGANISM: Artificial Sequence
<220> FEATURE:
<223> OTHER INFORMATION: Synthetic

<400> SEQUENCE: 28

Gln Ile Gln Leu Val Gln Ser Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
        115                 120                 125

<210> SEQ ID NO 29
<211> LENGTH: 126
<212> TYPE: PRT
<213> ORGANISM: Artificial Sequence
<220> FEATURE:
<223> OTHER INFORMATION: Synthetic

<400> SEQUENCE: 29

Gln Val Gln Leu Val Glu Ser Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
        115                 120                 125

<210> SEQ ID NO 30
<211> LENGTH: 109
<212> TYPE: PRT
<213> ORGANISM: Artificial Sequence
<220> FEATURE:
```

<223> OTHER INFORMATION: Synthetic

<400> SEQUENCE: 30

```
Gln Pro Val Leu Thr Gln Pro Ser Ala Ser Gly Thr Pro Gly Gln
1               5                   10                  15
Arg Val Thr Ile Ser Cys Ser Gly Ser Ser Asn Ile Gly Ser Asn
                20                  25                  30
Thr Val His Trp Tyr Gln Gln Leu Pro Gly Thr Ala Pro Lys Leu Leu
            35                  40                  45
Ile Tyr Ser Asp Asn Gln Arg Pro Ser Gly Val Pro Asp Arg Phe Ser
        50                  55                  60
Gly Ser Lys Ser Gly Thr Ser Ala Ser Leu Val Ile Ser Gly Leu Gln
65                  70                  75                  80
Ser Asp Asp Glu Ala Asp Tyr Tyr Cys Ala Ala Trp Asp Asp Ser Leu
                85                  90                  95
Asn Gly Val Phe Gly Gly Gly Thr Lys Leu Thr Val Leu
            100                 105
```

<210> SEQ ID NO 31
<211> LENGTH: 109
<212> TYPE: PRT
<213> ORGANISM: Artificial Sequence
<220> FEATURE:
<223> OTHER INFORMATION: Synthetic

<400> SEQUENCE: 31

```
Gln Ser Val Leu Thr Gln Pro Ser Ala Ser Gly Thr Pro Gly Gln
1               5                   10                  15
Arg Val Thr Ile Ser Cys Ser Gly Ser Ser Asn Ile Gly Ser Asn
                20                  25                  30
Thr Val His Trp Tyr Gln Gln Leu Pro Gly Thr Ala Pro Lys Leu Leu
            35                  40                  45
Ile Tyr Ser Asp Asn Gln Arg Pro Ser Gly Val Pro Asp Arg Phe Ser
        50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Asn Gly Val Phe Gly Gly Gly Thr Lys Leu Thr Val Leu
            100                 105
```

<210> SEQ ID NO 32
<211> LENGTH: 109
<212> TYPE: PRT
<213> ORGANISM: Artificial Sequence
<220> FEATURE:
<223> OTHER INFORMATION: Synthetic

<400> SEQUENCE: 32

```
Gln Pro Val Leu Thr Gln Pro Ser Ala Ser Gly Thr Pro Gly Gln
1               5                   10                  15
Arg Val Thr Ile Ser Cys Ser Gly Ser Thr Ser Asn Ile Gly Ser Asn
                20                  25                  30
Thr Val His Trp Tyr Gln Gln Leu Pro Gly Thr Ala Pro Lys Leu Leu
            35                  40                  45
Ile Tyr Ser Asp Asp Gln Arg Pro Ser Gly Val Pro Asp Arg Phe Ser
        50                  55                  60
Gly Ser Lys Ser Gly Thr Ser Ala Ser Leu Val Ile Ser Gly Leu Gln
```

-continued

```
                65                  70                  75                  80
Ser Asp Asp Glu Ala Asp Tyr Tyr Cys Ala Ala Trp Asp Glu Ser Leu
                    85                  90                  95

Asn Gly Val Phe Gly Gly Gly Thr Lys Leu Thr Val Leu
                100                 105

<210> SEQ ID NO 33
<211> LENGTH: 109
<212> TYPE: PRT
<213> ORGANISM: Artificial Sequence
<220> FEATURE:
<223> OTHER INFORMATION: Synthetic

<400> SEQUENCE: 33

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Ser Asn
                20                  25                  30

Thr Val His Trp Tyr Gln Gln Leu Pro Gly Thr Ala Pro Lys Leu Leu
            35                  40                  45

Ile Tyr Ser Asp Asp Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
                100                 105

<210> SEQ ID NO 34
<211> LENGTH: 109
<212> TYPE: PRT
<213> ORGANISM: Artificial Sequence
<220> FEATURE:
<223> OTHER INFORMATION: Synthetic

<400> SEQUENCE: 34

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Gly Asn
                20                  25                  30

Thr Val His Trp Tyr Gln Gln Leu Pro Gly Thr Ala Pro Lys Leu Leu
            35                  40                  45

Ile Tyr Ser Asp Asp Gln Arg Pro Ser Gly Val Pro Asp Arg Phe Ser
50                  55                  60

Gly Ser Lys Ser Gly Thr Ser Ala Ser Leu Val Ile Ser Gly Leu Gln
65                  70                  75                  80

Ser Asp Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
                100                 105

<210> SEQ ID NO 35
<211> LENGTH: 109
<212> TYPE: PRT
<213> ORGANISM: Artificial Sequence
<220> FEATURE:
<223> OTHER INFORMATION: Synthetic

<400> SEQUENCE: 35
```

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Thr Val His Trp Tyr Gln Gln Leu Pro Gly Thr Ala Pro Lys Leu Leu
        35                  40                  45

Ile Tyr Ser Asp Asp Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
            100                 105

<210> SEQ ID NO 36

<400> SEQUENCE: 36

000

<210> SEQ ID NO 37

<400> SEQUENCE: 37

000

<210> SEQ ID NO 38
<211> LENGTH: 378
<212> TYPE: DNA
<213> ORGANISM: Artificial Sequence
<220> FEATURE:
<223> OTHER INFORMATION: Synthetic

<400> SEQUENCE: 38
cagatccagc tggtgcagtc tgggggaggc gtggtccagc ctggagggtc cctgagactc        60
tcctgtgcag cgtctggatt caccttcagt agctatggca tgcactgggt ccgccaggct       120
ccaggcaagg ggctggagtg ggtggcagtt atatcatatg atggaagtaa taaatactat       180
gcagactccg tgaagggccg attcaccatc tccagagaca attccaagaa cacgctgtat       240
ctgcaaatga acagcctgag agccgaggac acggctgtgt attactgtgc gagagatctc       300
ctggtgcgat ttttggagtg gtcgcactac tacggtatgg acgtctgggg ccaagggacc       360
acggtcaccg tctcctca                                                     378

<210> SEQ ID NO 39
<211> LENGTH: 378
<212> TYPE: DNA
<213> ORGANISM: Artificial Sequence
<220> FEATURE:
<223> OTHER INFORMATION: Synthetic

<400> SEQUENCE: 39
caggtgcagc tggtggagtc tgggggaggc gtggtccagc ctggagggtc cctgagactc        60
tcctgtgcag cgtctggatt caccttcagt agctatggca tgcactgggt ccgccaggct       120
ccaggcaagg ggctggagtg ggtggcagtt atatcatatg atggaagtaa taaatactat       180
gcagactccg tgaagggccg attcaccatc tccagagaca attccaagaa cacgctgtat       240
ctgcaaatga acagcctgag agccgaggac acggctgtgt attactgtgc gagagatctc       300

```
ctggtgcgat ttttggagtg gtcgcactac tacggtatgg acgtctgggg ccaagggacc    360
acggtcaccg tctcctca                                                   378

<210> SEQ ID NO 40
<211> LENGTH: 378
<212> TYPE: DNA
<213> ORGANISM: Artificial Sequence
<220> FEATURE:
<223> OTHER INFORMATION: Synthetic

<400> SEQUENCE: 40
cagatccagc tggtgcagtc tggggaggc gtggtccagc ctgggaggtc cctgagactc     60
tcctgtgcag cgtctggatt cgccttcagt agctatggca tgcactgggt ccgccaggct   120
ccaggcaagg ggctggagtg ggtggcagtt atatcatatg atggaagtat caaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                  378

<210> SEQ ID NO 41
<211> LENGTH: 378
<212> TYPE: DNA
<213> ORGANISM: Artificial Sequence
<220> FEATURE:
<223> OTHER INFORMATION: Synthetic

<400> SEQUENCE: 41
caggtgcagc tggtggagtc tggggaggc gtggtccagc ctgggaggtc cctgagactc     60
tcctgtgcag cgtctggatt cgccttcagt agctatggca tgcactgggt ccgccaggct   120
ccaggcaagg ggctggagtg ggtggcagtt atatcatatg atggaagtat caaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                  378

<210> SEQ ID NO 42
<211> LENGTH: 378
<212> TYPE: DNA
<213> ORGANISM: Artificial Sequence
<220> FEATURE:
<223> OTHER INFORMATION: Synthetic

<400> SEQUENCE: 42
cagatccagc tggtgcagtc tggggaggc gtggtccagc ctgggaggtc cctgagactc     60
tcctgtgcag cgtctggatt cgccttcagt agctatggca tgcactgggt ccgccaggct   120
ccaggcaagg ggctggagtg ggtggcagtt atatcatatg atggaaataa taaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                  378

<210> SEQ ID NO 43
```

<211> LENGTH: 378
<212> TYPE: DNA
<213> ORGANISM: Artificial Sequence
<220> FEATURE:
<223> OTHER INFORMATION: Synthetic

<400> SEQUENCE: 43

| caggtgcagc tggtggagtc tgggggaggc gtggtccagc ctggaggtc cctgagactc | 60 |
| tcctgtgcag cgtctggatt cgccttcagt agctatggca tgcactgggt ccgccaggct | 120 |
| ccaggcaagg ggctggagtg ggtggcagtt atatcatatg atggaaataa taaatactat | 180 |
| gcagactccg tgaagggccg attcaccatc tccagagaca attccaagaa cacgctgtat | 240 |
| ctgcaaatga acagcctgag agccgaggac acggctgtgt attactgtgc gagagatctc | 300 |
| ctggtgcgat ttttggagtg gtcgcacaag tacggtatgg acgtctgggg ccaagggacc | 360 |
| acggtcaccg tctcctca | 378 |

<210> SEQ ID NO 44
<211> LENGTH: 327
<212> TYPE: DNA
<213> ORGANISM: Artificial Sequence
<220> FEATURE:
<223> OTHER INFORMATION: Synthetic

<400> SEQUENCE: 44

| cagcctgtgc tgactcagcc accctcagcg tctgggaccc ccgggcagag ggtcaccatc | 60 |
| tcttgttctg gaagcagctc caacatcgga agtaatactg tccactggta ccagcaactc | 120 |
| ccaggaacgg cccccaaact cctcatctat agtgataatc agcgcccctc agggttccct | 180 |
| gaccgattct ctggctccaa gtctggcacc tcagcctccc tggtcatcag tgggctccag | 240 |
| tctgacgatg aggctgatta ttactgtgca gcatgggatg acagcctgaa tggggtgttc | 300 |
| ggcggaggga ccaagctgac cgtccta | 327 |

<210> SEQ ID NO 45
<211> LENGTH: 327
<212> TYPE: DNA
<213> ORGANISM: Artificial Sequence
<220> FEATURE:
<223> OTHER INFORMATION: Synthetic

<400> SEQUENCE: 45

| cagtctgtgc tgactcagcc accctcagcg tctgggaccc ccgggcagag ggtcaccatc | 60 |
| tcttgttctg gaagcagctc caacatcgga agtaatactg tccactggta ccagcaactc | 120 |
| ccaggaacgg cccccaaact cctcatctat agtgataatc agcgcccctc agggttccct | 180 |
| gaccgattct ctggctccaa gtctggcacc tcagcctccc tggccatcag tgggctccag | 240 |
| tctgaggatg aggctgatta ttactgtgca gcatgggatg acagcctgaa tggggtgttc | 300 |
| ggcggaggga ccaagctgac cgtccta | 327 |

<210> SEQ ID NO 46
<211> LENGTH: 327
<212> TYPE: DNA
<213> ORGANISM: Artificial Sequence
<220> FEATURE:
<223> OTHER INFORMATION: Synthetic

<400> SEQUENCE: 46

| cagcctgtgc tgactcagcc accctcagcg tctgggaccc ccgggcagag ggtcaccatc | 60 |
| tcttgttctg gaagcacctc caacatcgga agtaatactg tccactggta ccagcaactc | 120 | ccaggaacgg cccccaaact cctcatctat agtgatgatc agcgcccctc agggtccct    180 gaccgattct ctggctccaa gtctggcacc tcagcctccc tggtcatcag tgggctccag    240 tctgacgatg aggctgatta ttactgtgca gcatgggatg agagcctgaa tggggtgttc    300 ggcggaggga ccaagctgac cgtccta                                        327

<210> SEQ ID NO 47
<211> LENGTH: 327
<212> TYPE: DNA
<213> ORGANISM: Artificial Sequence
<220> FEATURE:
<223> OTHER INFORMATION: Synthetic

<400> SEQUENCE: 47
cagtctgtgc tgactcagcc accctcagcg tctgggaccc ccgggcagag ggtcaccatc     60
tcttgttctg gaagcacctc caacatcgga agtaatactg tccactggta ccagcaactc    120
ccaggaacgg cccccaaact cctcatctat agtgatgatc agcgcccctc agggtccct    180 gaccgattct ctggctccaa gtctggcacc tcagcctccc tggccatcag tgggctccag    240
tctgaggatg aggctgatta ttactgtgca gcatgggatg agagcctgaa tggggtgttc    300
ggcggaggga ccaagctgac cgtccta                                        327

<210> SEQ ID NO 48
<211> LENGTH: 327
<212> TYPE: DNA
<213> ORGANISM: Artificial Sequence
<220> FEATURE:
<223> OTHER INFORMATION: Synthetic

<400> SEQUENCE: 48
cagcctgtgc tgactcagcc accctcagcg tctgggaccc ccgggcagag ggtcaccatc     60
tcttgttctg gaagcagctc caacatcgga ggaaatactg tccactggta ccagcaactc    120
ccaggaacgg cccccaaact cctcatctat agtgatgatc agcgcccctc agggtccct    180 gaccgattct ctggctccaa gtctggcacc tcagcctccc tggtcatcag tgggctccag    240
tctgacgatg aggctgatta ttactgtgca gcatgggatg agagcctgaa tggggtgttc    300
ggcggaggga ccaagctgac cgtccta                                        327

<210> SEQ ID NO 49
<211> LENGTH: 327
<212> TYPE: DNA
<213> ORGANISM: Artificial Sequence
<220> FEATURE:
<223> OTHER INFORMATION: Synthetic

<400> SEQUENCE: 49
cagtctgtgc tgactcagcc accctcagcg tctgggaccc ccgggcagag ggtcaccatc     60
tcttgttctg gaagcagctc caacatcgga ggaaatactg tccactggta ccagcaactc    120
ccaggaacgg cccccaaact cctcatctat agtgatgatc agcgcccctc agggtccct    180 gaccgattct ctggctccaa gtctggcacc tcagcctccc tggccatcag tgggctccag    240
tctgaggatg aggctgatta ttactgtgca gcatgggatg agagcctgaa tggggtgttc    300
ggcggaggga ccaagctgac cgtccta                                        327

<210> SEQ ID NO 50
<211> LENGTH: 452
<212> TYPE: PRT

<213> ORGANISM: Artificial Sequence
<220> FEATURE:
<223> OTHER INFORMATION: Synthetic

<400> SEQUENCE: 50

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
```

```
                385                 390                 395                 400
            Pro Pro Val Leu Asp Ser Asp Gly Ser Phe Phe Leu Tyr Ser Arg Leu
                            405                 410                 415

Thr Val Asp Lys Ser Arg Trp Gln Glu Gly Asn Val Phe Ser Cys Ser
                            420                 425                 430

Val Met His Glu Ala Leu His Asn His Tyr Thr Gln Lys Ser Leu Ser
                    435                 440                 445

Leu Ser Leu Gly
                450

<210> SEQ ID NO 51
<211> LENGTH: 215
<212> TYPE: PRT
<213> ORGANISM: Artificial Sequence
<220> FEATURE:
<223> OTHER INFORMATION: Synthetic

<400> SEQUENCE: 51

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 52

<400> SEQUENCE: 52

000

<210> SEQ ID NO 53

<400> SEQUENCE: 53

000
```

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71
<211> LENGTH: 17
<212> TYPE: PRT
<213> ORGANISM: Artificial Sequence
<220> FEATURE:
<223> OTHER INFORMATION: Synthetic

<400> SEQUENCE: 71

Glu Ser Leu Ile Arg Phe Leu Glu Asp Pro Gln Gln Gly Gly Met Asp
1               5                   10                  15

Val

<210> SEQ ID NO 72
<211> LENGTH: 10
<212> TYPE: PRT
<213> ORGANISM: Artificial Sequence
<220> FEATURE:
<223> OTHER INFORMATION: Synthetic

<400> SEQUENCE: 72

Asn Ser Trp Thr Arg Ser Asn Asn Tyr Ile
1               5                   10

<210> SEQ ID NO 73
<211> LENGTH: 126
<212> TYPE: PRT
<213> ORGANISM: Artificial Sequence
<220> FEATURE:
<223> OTHER INFORMATION: Synthetic

<400> SEQUENCE: 73

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Leu Ile Arg Phe Leu Glu Asp Pro Gln Gln Gly Gly
            100                 105                 110

Met Asp Val Trp Gly Gln Gly Thr Thr Val Thr Val Ser Ser
        115                 120                 125

<210> SEQ ID NO 74
<211> LENGTH: 121
<212> TYPE: PRT
<213> ORGANISM: Artificial Sequence
<220> FEATURE:
<223> OTHER INFORMATION: Synthetic

<400> SEQUENCE: 74

Gln Ser Ala Leu Thr Gln Pro Ala Ser Val Ser Gly Ser Pro Gly Gln
1               5                   10                  15

Ser Leu Thr Ile Ser Cys Thr Gly Thr Ser Ser Asp Ile Gly Gly Tyr
                20                  25                  30

Asn Tyr Val Ser Trp Tyr Gln Gln His Pro Gly Lys Ala Pro Lys Leu
            35                  40                  45

Ile Ile Tyr Asp Val Thr Asp Arg Pro Ser Gly Val Ser Gly Arg Phe
        50                  55                  60

Ser Gly Ser Lys Ser Gly Asn Thr Ala Ser Leu Thr Ile Ser Gly Leu
65                  70                  75                  80

Gln Thr Glu Asp Glu Ala Glu Tyr Phe Cys Asn Ser Trp Thr Arg Ser
                85                  90                  95

Asn Asn Tyr Ile Phe Gly Gly Gly Thr Lys Leu Thr Val Leu Gly Gln
            100                 105                 110

Pro Lys Ala Ala Pro Ser Val Thr Leu
        115                 120

<210> SEQ ID NO 75
<211> LENGTH: 273
<212> TYPE: PRT
<213> ORGANISM: Artificial Sequence
<220> FEATURE:
<223> OTHER INFORMATION: Synthetic

<400> SEQUENCE: 75

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

```
Gln Gly Arg Val Thr Met Thr Arg Asp Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Ser Leu Ile Arg Phe Leu Glu Asp Pro Gln Gly Gly
            100                 105                 110

Met Asp Val Trp Gly Gln Gly Thr Thr Val Thr Val Ser Ser Gly Ser
        115                 120                 125

Ala Ser Ala Pro Thr Leu Gly Gly Gly Ser Gly Gly Gly Gly Ser
130                 135                 140

Ala Ala Ala Gln Ser Ala Leu Thr Gln Pro Ala Ser Val Ser Gly Ser
145                 150                 155                 160

Pro Gly Gln Ser Leu Thr Ile Ser Cys Thr Gly Thr Ser Ser Asp Ile
                165                 170                 175

Gly Gly Tyr Asn Tyr Val Ser Trp Tyr Gln Gln His Pro Gly Lys Ala
            180                 185                 190

Pro Lys Leu Ile Ile Tyr Asp Val Thr Asp Arg Pro Ser Gly Val Ser
        195                 200                 205

Gly Arg Phe Ser Gly Ser Lys Ser Gly Asn Thr Ala Ser Leu Thr Ile
210                 215                 220

Ser Gly Leu Gln Thr Glu Asp Glu Ala Glu Tyr Phe Cys Asn Ser Trp
225                 230                 235                 240

Thr Arg Ser Asn Asn Tyr Ile Phe Gly Gly Gly Thr Lys Leu Thr Val
                245                 250                 255

Leu Gly Gln Pro Lys Ala Ala Pro Ser Val Thr Leu Phe Pro Pro Ser
            260                 265                 270

Ser

<210> SEQ ID NO 76
<211> LENGTH: 13
<212> TYPE: PRT
<213> ORGANISM: Artificial Sequence
<220> FEATURE:
<223> OTHER INFORMATION: Synthetic

<400> SEQUENCE: 76

Asp Arg Tyr Ser Ser Ser Trp Gly Gly Gly Phe Asp Tyr
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic

<400> SEQUENCE: 77

Gln Ser Tyr Asp Ala Ser Ser Leu Trp Val
1               5                   10

<210> SEQ ID NO 78
<211> LENGTH: 122
<212> TYPE: PRT
<213> ORGANISM: Artificial Sequence
<220> FEATURE:
<223> OTHER INFORMATION: Synthetic

<400> SEQUENCE: 78

Glu Val Gln Leu Val Gln Ser Gly Gly Gly Val Val Gln Ser Gly Arg
```

-continued

```
                 1               5                  10                 15
            Ser Leu Arg Leu Ser Cys Val Ala Ser Gly Phe Ser Phe Ser Asn Tyr
                             20                 25                 30
            Gly Met His Trp Val Arg Gln Ala Pro Gly Lys Gly Leu Glu Trp Leu
                         35                 40                 45
            Ala Phe Ile Trp Tyr Asp Gly Ser Asn Lys Trp Tyr Ala Asp Ser Val
                     50                 55                 60
            Lys Gly Arg Phe Thr Ile Ser Arg Asp Asn Ser Lys Asn Ala Leu Tyr
            65                 70                 75                 80
            Leu Gln Met Asn Ser Leu Arg Ala Glu Asp Thr Ala Val Tyr Tyr Cys
                             85                 90                 95
            Ala Arg Asp Arg Tyr Ser Ser Trp Gly Gly Phe Asp Tyr Trp
                            100                105                110
            Gly Gln Gly Thr Val Leu Thr Val Ser Ser
                        115                120
```

<210> SEQ ID NO 79
<211> LENGTH: 122
<212> TYPE: PRT
<213> ORGANISM: Artificial Sequence
<220> FEATURE:
<223> OTHER INFORMATION: Synthetic

<400> SEQUENCE: 79

```
Asn Phe Met Leu Thr Gln Pro His Ser Val Ser Glu Ser Pro Gly Arg
1               5                  10                 15
Thr Val Thr Ile Pro Cys Ser Gly Arg Gly Gly Ser Ile Ala Ser Asp
            20                 25                 30
Ser Val Gln Trp Tyr Gln Gln Arg Pro Gly Ser Ala Pro Thr Thr Ile
        35                 40                 45
Ile Tyr Glu Asp Asn Gln Arg Pro Ser Gly Val Pro Asp Arg Phe Ser
    50                 55                 60
Gly Ser Val Asp Ser Ser Ser Asn Ser Ala Ser Leu Thr Ile Ser Gly
65                 70                 75                 80
Leu Arg Thr Glu Asp Glu Ala Asp Tyr Tyr Cys Gln Ser Tyr Asp Ala
            85                 90                 95
Ser Ser Leu Trp Val Phe Gly Gly Lys Thr Lys Leu Thr Val Leu Gly
        100                105                110
Gln Pro Lys Ala Ala Pro Ser Val Thr Leu
        115                120
```

<210> SEQ ID NO 80
<211> LENGTH: 275
<212> TYPE: PRT
<213> ORGANISM: Artificial Sequence
<220> FEATURE:
<223> OTHER INFORMATION: Synthetic

<400> SEQUENCE: 80

```
Glu Val Gln Leu Val Gln Ser Gly Gly Gly Val Val Gln Ser Gly Arg
1               5                  10                 15
Ser Leu Arg Leu Ser Cys Val Ala Ser Gly Phe Ser Phe Ser Asn Tyr
            20                 25                 30
Gly Met His Trp Val Arg Gln Ala Pro Gly Lys Gly Leu Glu Trp Leu
        35                 40                 45
Ala Phe Ile Trp Tyr Asp Gly Ser Asn Lys Trp Tyr Ala Asp Ser Val
    50                 55                 60
```

```
Lys Gly Arg Phe Thr Ile Ser Arg Asp Asn Ser Lys Asn Ala Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Tyr Ser Ser Ser Trp Gly Gly Phe Asp Tyr Trp
            100                 105                 110

Gly Gln Gly Thr Val Leu Thr Val Ser Ser Gly Ser Ala Ser Ala Pro
            115                 120                 125

Thr Leu Gly Gly Gly Ser Gly Gly Gly Ser Ala Ala Ala Asn
            130                 135                 140

Phe Met Leu Thr Gln Pro His Ser Val Ser Glu Ser Pro Gly Arg Thr
145                 150                 155                 160

Val Thr Ile Pro Cys Ser Gly Arg Gly Ser Ile Ala Ser Asp Ser
                165                 170                 175

Val Gln Trp Tyr Gln Gln Arg Pro Gly Ser Ala Pro Thr Thr Ile Ile
            180                 185                 190

Tyr Glu Asp Asn Gln Arg Pro Ser Gly Val Pro Asp Arg Phe Ser Gly
            195                 200                 205

Ser Val Asp Ser Ser Ser Asn Ser Ala Ser Leu Thr Ile Ser Gly Leu
210                 215                 220

Arg Thr Glu Asp Glu Ala Asp Tyr Tyr Cys Gln Ser Tyr Asp Ala Ser
225                 230                 235                 240

Ser Leu Trp Val Phe Gly Gly Lys Thr Lys Leu Thr Val Leu Gly Gln
                245                 250                 255

Pro Lys Ala Ala Pro Ser Val Thr Leu Phe Pro Pro Ser Ser Lys Ala
            260                 265                 270

Ser Gly Ala
        275

<210> SEQ ID NO 81
<211> LENGTH: 10
<212> TYPE: PRT
<213> ORGANISM: Artificial Sequence
<220> FEATURE:
<223> OTHER INFORMATION: Synthetic

<400> SEQUENCE: 81

Asp Arg His Ser Leu Gly Asp Phe Asp Tyr
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Synthetic

<400> SEQUENCE: 82

Gln Ala Trp Asp Ser Thr Thr Val Val
1               5

<210> SEQ ID NO 83
<211> LENGTH: 121
<212> TYPE: PRT
<213> ORGANISM: Artificial Sequence
<220> FEATURE:
<223> OTHER INFORMATION: Synthetic

<400> SEQUENCE: 83

Gln Leu Gln Leu Gln Gln Ser Gly Gly Gly Leu Val Lys Pro Gly Gly
```

```
1               5                   10                  15
Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Arg His Ser Leu Gly Asp Phe Asp Tyr Trp Gly Gln Gly
            100                 105                 110

Thr Leu Val Thr Val Ser Ser Gly Ser
            115                 120
```

<210> SEQ ID NO 84
<211> LENGTH: 121
<212> TYPE: PRT
<213> ORGANISM: Artificial Sequence
<220> FEATURE:
<223> OTHER INFORMATION: Synthetic

<400> SEQUENCE: 84

```
Ser Ser Glu Leu Thr Gln Pro Ser Val Ser Val Ser Pro Gly Gln Thr
1               5                   10                  15

Ala Thr Ile Thr Cys Ser Gly Asp Lys Leu Gly Asp Lys Tyr Ala Ser
                20                  25                  30

Trp Tyr Gln Gln Lys Pro Gly Gln Ser Pro Val Leu Val Ile Tyr Gln
            35                  40                  45

Asp Thr Lys Arg Pro Ser Gly Ile Pro Ala Arg Phe Ser Gly Ser Asn
        50                  55                  60

Ser Gly Asn Thr Ala Thr Leu Thr Ile Ser Gly Thr Gln Ala Met Asp
65                  70                  75                  80

Glu Ala Ala Tyr Tyr Cys Gln Ala Trp Asp Ser Thr Val Val Phe
                85                  90                  95

Gly Gly Gly Thr Lys Leu Thr Val Leu Gly Gln Pro Lys Ala Ala Pro
            100                 105                 110

Ser Val Thr Leu Phe Pro Pro Ser Ser
        115                 120
```

<210> SEQ ID NO 85
<211> LENGTH: 201
<212> TYPE: PRT
<213> ORGANISM: Artificial Sequence
<220> FEATURE:
<223> OTHER INFORMATION: Synthetic

<400> SEQUENCE: 85

```
Gln Leu Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
        50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Val Arg Asp Arg His Ser Leu Gly Asp Phe Asp Tyr Trp Gly Gln Gly
            100                 105                 110

Thr Leu Val Thr Val Ser Ser Gly Ser Ala Ser Ala Pro Thr Leu Gly
        115                 120                 125

Gly Gly Gly Ser Gly Gly Gly Ser Ala Ala Ala Ser Ser Glu Leu
    130                 135                 140

Thr Gln Pro Pro Ser Val Ser Val Ser Pro Gly Gln Thr Ala Thr Ile
145                 150                 155                 160

Thr Cys Ser Gly Asp Lys Leu Gly Asp Lys Tyr Ala Ser Trp Tyr Gln
                165                 170                 175

Gln Lys Pro Gly Gln Ser Pro Val Leu Val Ile Tyr Gln Asp Thr Lys
            180                 185                 190

Arg Pro Ser Gly Ile Pro Ala Arg Phe
        195                 200
```

<210> SEQ ID NO 86
<211> LENGTH: 18
<212> TYPE: PRT
<213> ORGANISM: Artificial Sequence
<220> FEATURE:
<223> OTHER INFORMATION: Synthetic

<400> SEQUENCE: 86

```
His Gly Leu Met Asp Asp Ser Ser Gly Tyr Tyr Leu Ser Asn Ala Phe
 1               5                  10                  15

Asp Ile
```

<210> SEQ ID NO 87
<211> LENGTH: 11
<212> TYPE: PRT
<213> ORGANISM: Artificial Sequence
<220> FEATURE:
<223> OTHER INFORMATION: Synthetic

<400> SEQUENCE: 87

```
Ala Thr Trp Asp Asp Ser Leu Thr Gly Val Val
 1               5                  10
```

<210> SEQ ID NO 88
<211> LENGTH: 129
<212> TYPE: PRT
<213> ORGANISM: Artificial Sequence
<220> FEATURE:
<223> OTHER INFORMATION: Synthetic

<400> SEQUENCE: 88

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80
```

```
Met Glu Leu Ser Ser Leu Arg Ser Glu Asp Thr Ala Val Tyr Tyr Cys
                85                  90                  95

Ala Asn His Gly Leu Met Asp Asp Ser Ser Gly Tyr Tyr Leu Ser Asn
            100                 105                 110

Ala Phe Asp Ile Trp Gly Gln Gly Thr Met Val Thr Val Ser Ser Gly
        115                 120                 125

Ser

<210> SEQ ID NO 89
<211> LENGTH: 126
<212> TYPE: PRT
<213> ORGANISM: Artificial Sequence
<220> FEATURE:
<223> OTHER INFORMATION: Synthetic

<400> SEQUENCE: 89

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Glu Trp Tyr Gln Gln Leu Pro Gly Thr Ala Pro Lys Leu Leu
        35                  40                  45

Ile His Ser Asn Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Phe Cys Ala Thr Trp Asp Asp Ser Leu
                85                  90                  95

Thr Gly Val Val Phe Gly Gly Gly Thr Thr Leu Thr Val Leu Gly Gln
            100                 105                 110

Pro Lys Ala Ala Pro Ser Val Thr Leu Phe Pro Pro Ser Ser
        115                 120                 125

<210> SEQ ID NO 90
<211> LENGTH: 274
<212> TYPE: PRT
<213> ORGANISM: Artificial Sequence
<220> FEATURE:
<223> OTHER INFORMATION: Synthetic

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn His Gly Leu Met Asp Asp Ser Ser Gly Tyr Tyr Leu Ser Asn
            100                 105                 110

Ala Phe Asp Ile Trp Gly Gln Gly Thr Met Val Thr Val Ser Ser Gly
        115                 120                 125
```

```
Ser Ala Ser Ala Pro Thr Leu Gly Gly Gly Ser Gly Gly Gly
    130                 135                 140

Ser Ala Ala Ala Gln Pro Val Leu Thr Gln Pro Pro Ser Ala Ser Gly
145                 150                 155                 160

Thr Pro Gly Gln Arg Val Thr Ile Ser Cys Ser Gly Ser Ser Ser Asn
                165                 170                 175

Ile Gly Ser Asn Thr Val Glu Trp Tyr Gln Gln Leu Pro Gly Thr Ala
            180                 185                 190

Pro Lys Leu Leu Ile His Ser Asn Asn Gln Arg Pro Ser Gly Val Pro
        195                 200                 205

Asp Arg Phe Ser Gly Ser Arg Ser Gly Thr Ser Ala Ser Leu Ala Ile
    210                 215                 220

Ser Gly Leu Gln Ser Glu Asp Glu Ala Asp Tyr Phe Cys Ala Thr Trp
225                 230                 235                 240

Asp Asp Ser Leu Thr Gly Val Val Phe Gly Gly Gly Thr Thr Leu Thr
                245                 250                 255

Val Leu Gly Gln Pro Lys Ala Ala Pro Ser Val Thr Leu Phe Pro Pro
            260                 265                 270

Ser Ser

<210> SEQ ID NO 91
<211> LENGTH: 12
<212> TYPE: PRT
<213> ORGANISM: Artificial Sequence
<220> FEATURE:
<223> OTHER INFORMATION: Synthetic

<400> SEQUENCE: 91

Val Gly Thr Ala Ala Gly Asp Ala Phe Asp Ile
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic

<400> SEQUENCE: 92

Ala Ala Trp Asp Asp Ser Leu Ser Gly Trp Val
1               5                   10

<210> SEQ ID NO 93
<211> LENGTH: 123
<212> TYPE: PRT
<213> ORGANISM: Artificial Sequence
<220> FEATURE:
<223> OTHER INFORMATION: Synthetic

<400> SEQUENCE: 93

Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Val Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Leu Tyr Tyr Cys
                85                  90                  95

Ala Lys Val Gly Thr Ala Ala Ala Gly Asp Ala Phe Asp Ile Trp Gly
            100                 105                 110

Gln Gly Thr Met Val Thr Val Ser Ser Gly Ser
            115                 120
```

<210> SEQ ID NO 94
<211> LENGTH: 126
<212> TYPE: PRT
<213> ORGANISM: Artificial Sequence
<220> FEATURE:
<223> OTHER INFORMATION: Synthetic

<400> SEQUENCE: 94

```
Gln Pro Val Leu Thr Gln Pro Pro Ser Ala Ser Gly Thr Pro Gly Gln
1               5                   10                  15

Arg Val Thr Ile Ser Cys Phe Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser
        115                 120                 125
```

<210> SEQ ID NO 95
<211> LENGTH: 268
<212> TYPE: PRT
<213> ORGANISM: Artificial Sequence
<220> FEATURE:
<223> OTHER INFORMATION: Synthetic

<400> SEQUENCE: 95

```
Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Val Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Val Gly Thr Ala Ala Ala Gly Asp Ala Phe Asp Ile Trp Gly
            100                 105                 110

Gln Gly Thr Met Val Thr Val Ser Ser Gly Ser Ala Ser Ala Pro Thr
        115                 120                 125
```

```
Leu Gly Gly Gly Ser Gly Gly Gly Ser Ala Ala Gln Pro
    130             135             140

Val Leu Thr Gln Pro Pro Ser Ala Ser Gly Thr Pro Gly Gln Arg Val
145                 150                 155                 160

Thr Ile Ser Cys Phe Gly Ser Ser Ser Asn Ile Gly Ser Asn Tyr Val
                165                 170                 175

Tyr Trp Tyr Gln Gln Leu Pro Gly Thr Ala Pro Lys Leu Leu Ile Tyr
                180                 185                 190

Arg Asn Asn Gln Arg Pro Ser Gly Val Pro Asp Arg Phe Ser Gly Ser
                195                 200                 205

Lys Ser Gly Thr Ser Ala Ser Leu Ala Ile Ser Gly Leu Arg Ser Glu
    210                 215                 220

Asp Glu Ala Asp Tyr Tyr Cys Ala Ala Trp Asp Ser Leu Ser Gly
225                 230                 235                 240

Trp Val Phe Gly Gly Gly Thr Lys Leu Thr Val Leu Gly Gln Pro Lys
                245                 250                 255

Ala Ala Pro Ser Val Thr Leu Phe Pro Pro Ser Ser
            260                 265
```

<210> SEQ ID NO 96
<211> LENGTH: 18
<212> TYPE: PRT
<213> ORGANISM: Artificial Sequence
<220> FEATURE:
<223> OTHER INFORMATION: Synthetic

<400> SEQUENCE: 96

```
Val Gly Phe Tyr Asp Tyr Val Trp Gly Ser Tyr Pro Tyr Asp Ala Phe
1               5                   10                  15

Asp Ile
```

<210> SEQ ID NO 97
<211> LENGTH: 9
<212> TYPE: PRT
<213> ORGANISM: Artificial Sequence
<220> FEATURE:
<223> OTHER INFORMATION: Synthetic

<400> SEQUENCE: 97

```
Gln Gln Tyr Gly Thr Ser Pro Leu Thr
1               5
```

<210> SEQ ID NO 98
<211> LENGTH: 127
<212> TYPE: PRT
<213> ORGANISM: Artificial Sequence
<220> FEATURE:
<223> OTHER INFORMATION: Synthetic

<400> SEQUENCE: 98

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Arg Val Gly Phe Tyr Asp Tyr Val Trp Gly Ser Tyr Pro Tyr Asp
            100                 105                 110

Ala Phe Asp Ile Trp Gly Gln Gly Thr Met Val Thr Val Ser Ser
        115                 120                 125

<210> SEQ ID NO 99
<211> LENGTH: 108
<212> TYPE: PRT
<213> ORGANISM: Artificial Sequence
<220> FEATURE:
<223> OTHER INFORMATION: Synthetic

<400> SEQUENCE: 99

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Asp Ala Ser Asn Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Leu Tyr Tyr Cys Gln Gln Tyr Gly Thr Ser Pro
                85                  90                  95

Leu Thr Phe Gly Gly Gly Thr Lys Leu Glu Ile Lys
            100                 105

<210> SEQ ID NO 100
<211> LENGTH: 265
<212> TYPE: PRT
<213> ORGANISM: Artificial Sequence
<220> FEATURE:
<223> OTHER INFORMATION: Synthetic

<400> SEQUENCE: 100

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Phe Tyr Asp Tyr Val Trp Gly Ser Tyr Pro Tyr Asp
            100                 105                 110

Ala Phe Asp Ile Trp Gly Gln Gly Thr Met Val Thr Val Ser Ser Gly
        115                 120                 125

Ser Ala Ser Ala Pro Thr Leu Gly Gly Gly Ser Gly Gly Gly Gly
    130                 135                 140

Ser Ala Ala Ala Glu Ile Val Met Thr Gln Ser Pro Gly Thr Leu Ser

```
            145                 150                 155                 160
Leu Ser Pro Gly Glu Arg Ala Thr Leu Ser Cys Arg Ala Ser Gln Ser
                165                 170                 175

Val Ser Ser Asn Tyr Leu Ala Trp Tyr Gln Gln Lys Pro Gly Gln Ala
                180                 185                 190

Pro Arg Leu Leu Ile Tyr Asp Ala Ser Asn Arg Ala Thr Gly Ile Pro
                195                 200                 205

Ala Arg Phe Ser Gly Ser Gly Ser Gly Thr Asp Phe Thr Leu Thr Ile
            210                 215                 220

Ser Ser Leu Glu Pro Glu Asp Phe Ala Leu Tyr Tyr Cys Gln Gln Tyr
225                 230                 235                 240

Gly Thr Ser Pro Leu Thr Phe Gly Gly Thr Lys Leu Glu Ile Lys
                245                 250                 255

Arg Thr Val Ala Ala Pro Ser Val Phe
                260                 265

<210> SEQ ID NO 101
<211> LENGTH: 14
<212> TYPE: PRT
<213> ORGANISM: Artificial Sequence
<220> FEATURE:
<223> OTHER INFORMATION: Synthetic

<400> SEQUENCE: 101

Asp Thr Ser Asn Gly Gly Tyr Ser Ser Ser Ser Phe Asp Tyr
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic

<400> SEQUENCE: 102

Ser Ser Tyr Thr Ser Ser Ser Thr Leu Val
1               5                   10

<210> SEQ ID NO 103
<211> LENGTH: 123
<212> TYPE: PRT
<213> ORGANISM: Artificial Sequence
<220> FEATURE:
<223> OTHER INFORMATION: Synthetic

<400> SEQUENCE: 103

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Thr Ser Asn Gly Gly Tyr Ser Ser Ser Phe Asp Tyr
                100                 105                 110
```

```
Trp Gly Gln Gly Thr Leu Val Thr Val Ser Ser
        115                 120

<210> SEQ ID NO 104
<211> LENGTH: 110
<212> TYPE: PRT
<213> ORGANISM: Artificial Sequence
<220> FEATURE:
<223> OTHER INFORMATION: Synthetic

<400> SEQUENCE: 104

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Thr Ala Pro Lys Leu
        35                  40                  45

Met Ile Tyr Asp Val Ser Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Thr Gly Thr Lys Val Thr Val Leu
            100                 105                 110

<210> SEQ ID NO 105
<211> LENGTH: 270
<212> TYPE: PRT
<213> ORGANISM: Artificial Sequence
<220> FEATURE:
<223> OTHER INFORMATION: Synthetic

<400> SEQUENCE: 105

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Thr Ser Asn Gly Gly Tyr Ser Ser Ser Ser Phe Asp Tyr
            100                 105                 110

Trp Gly Gln Gly Thr Leu Val Thr Val Ser Ser Gly Ser Ala Ser Ala
        115                 120                 125

Pro Thr Leu Gly Gly Gly Gly Ser Gly Gly Gly Ser Ala Ala Ala
    130                 135                 140

Gln Ser Ala Leu Thr Gln Pro Ala Ser Val Ser Gly Ser Pro Gly Gln
145                 150                 155                 160

Ser Ile Thr Ile Ser Cys Thr Gly Thr Ser Ser Asp Val Gly Gly Tyr
                165                 170                 175

Asn Tyr Val Ser Trp Tyr Gln Gln His Pro Gly Thr Ala Pro Lys Leu
```

```
            180                 185                 190
Met Ile Tyr Asp Val Ser Tyr Arg Pro Ser Gly Val Ser Asn Arg Phe
                195                 200                 205

Ser Gly Ser Lys Ser Gly Asn Thr Ala Ser Leu Thr Ile Ser Gly Leu
    210                 215                 220

Gln Ala Glu Asp Glu Ala Asp Tyr Tyr Cys Ser Ser Tyr Thr Ser Ser
225                 230                 235                 240

Ser Thr Leu Val Phe Gly Thr Gly Thr Lys Val Thr Val Leu Gly Gln
                245                 250                 255

Pro Lys Ala Asn Pro Thr Val Thr Leu Phe Pro Pro Ser Ser
            260                 265                 270

<210> SEQ ID NO 106
<211> LENGTH: 15
<212> TYPE: PRT
<213> ORGANISM: Artificial Sequence
<220> FEATURE:
<223> OTHER INFORMATION: Synthetic

<400> SEQUENCE: 106

Leu Val Tyr Gly Gly Tyr Asp Glu Pro Gly Tyr Tyr Phe Asp Tyr
1               5                   10                  15

<210> SEQ ID NO 107
<211> LENGTH: 11
<212> TYPE: PRT
<213> ORGANISM: Artificial Sequence
<220> FEATURE:
<223> OTHER INFORMATION: Synthetic

<400> SEQUENCE: 107

Ala Ala Trp Asp Asp Ser Leu Asn Gly Trp Val
1               5                   10

<210> SEQ ID NO 108
<211> LENGTH: 124
<212> TYPE: PRT
<213> ORGANISM: Artificial Sequence
<220> FEATURE:
<223> OTHER INFORMATION: Synthetic

<400> SEQUENCE: 108

Glu Val Gln Leu Leu Glu Ser Arg Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Pro Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Val Tyr Gly Gly Tyr Asp Glu Pro Gly Tyr Tyr Phe Asp
            100                 105                 110

Tyr Trp Gly Gln Gly Thr Leu Val Thr Val Ser Ser
        115                 120

<210> SEQ ID NO 109
```

<211> LENGTH: 110
<212> TYPE: PRT
<213> ORGANISM: Artificial Sequence
<220> FEATURE:
<223> OTHER INFORMATION: Synthetic

<400> SEQUENCE: 109

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Arg Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110

<210> SEQ ID NO 110
<211> LENGTH: 276
<212> TYPE: PRT
<213> ORGANISM: Artificial Sequence
<220> FEATURE:
<223> OTHER INFORMATION: Synthetic

<400> SEQUENCE: 110

Glu Val Gln Leu Leu Glu Ser Arg Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Pro Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Val Tyr Gly Gly Tyr Asp Glu Pro Gly Tyr Tyr Phe Asp
            100                 105                 110

Tyr Trp Gly Gln Gly Thr Leu Val Thr Val Ser Ser Gly Ser Ala Ser
        115                 120                 125

Ala Pro Thr Leu Gly Gly Gly Ser Gly Gly Gly Ser Ala Ala
    130                 135                 140

Ala Gln Ser Val Leu Thr Gln Pro Pro Ser Ala Ser Gly Thr Pro Gly
145                 150                 155                 160

Gln Arg Val Thr Ile Ser Cys Ser Gly Ser Ser Ser Asn Ile Arg Ser
                165                 170                 175

Asn Thr Val Asn Trp Tyr Gln Gln Leu Pro Gly Thr Ala Pro Lys Leu
            180                 185                 190

Leu Ile Tyr Ser Asn Asn Gln Arg Pro Ser Gly Val Pro Asp Arg Phe
        195                 200                 205

Ser Gly Ser Lys Ser Gly Thr Ser Ala Ser Leu Ala Ile Ser Gly Leu

```
                  210                 215                 220

Gln Ser Glu Asp Glu Ala Asp Tyr Tyr Cys Ala Ala Trp Asp Asp Ser
225                 230                 235                 240

Leu Asn Gly Trp Val Phe Gly Gly Thr Lys Leu Thr Val Leu Gly
                245                 250                 255

Gln Pro Lys Ala Ala Pro Ser Val Thr Leu Phe Pro Pro Ser Ser Lys
                260                 265                 270

Ala Ser Gly Ala
        275

<210> SEQ ID NO 111
<211> LENGTH: 14
<212> TYPE: PRT
<213> ORGANISM: Artificial Sequence
<220> FEATURE:
<223> OTHER INFORMATION: Synthetic

<400> SEQUENCE: 111

Val Asp Gly Leu Glu Tyr Ser Ser Gly His Asn Phe Asp Tyr
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic

<400> SEQUENCE: 112

Ser Ser Tyr Ala Gly Ser Tyr Thr Trp Val
1               5                   10

<210> SEQ ID NO 113
<211> LENGTH: 123
<212> TYPE: PRT
<213> ORGANISM: Artificial Sequence
<220> FEATURE:
<223> OTHER INFORMATION: Synthetic

<400> SEQUENCE: 113

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Leu Glu Tyr Ser Ser Gly His Asn Phe Asp Tyr
            100                 105                 110

Trp Gly Gln Gly Thr Leu Val Thr Val Ser Ser
        115                 120

<210> SEQ ID NO 114
<211> LENGTH: 110
<212> TYPE: PRT
<213> ORGANISM: Artificial Sequence
```

<220> FEATURE:
<223> OTHER INFORMATION: Synthetic

<400> SEQUENCE: 114

```
Gln Ser Ala Leu Thr Gln Pro Pro Ser Val Ser Gly Ser Pro Gly Gln
1               5                   10                  15

Ser Val Thr Ile Ser Cys Thr Gly Ser Ser Asp Val Gly Tyr Tyr
            20                  25                  30

Asp His Val Ser Trp Tyr Gln His Pro Gly Arg Ala Pro Lys Val
        35                  40                  45

Ile Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Ala Gly Ser
                85                  90                  95

Tyr Thr Trp Val Phe Gly Gly Gly Thr Glu Leu Thr Val Leu
            100                 105                 110
```

<210> SEQ ID NO 115
<211> LENGTH: 270
<212> TYPE: PRT
<213> ORGANISM: Artificial Sequence
<220> FEATURE:
<223> OTHER INFORMATION: Synthetic

<400> SEQUENCE: 115

```
Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Val Asp Gly Leu Glu Tyr Ser Ser Gly His Asn Phe Asp Tyr
                100                 105                 110

Trp Gly Gln Gly Thr Leu Val Thr Val Ser Ser Gly Ser Ala Ser Ala
            115                 120                 125

Pro Thr Leu Gly Gly Gly Gly Ser Gly Gly Gly Ser Ala Ala Ala
            130                 135                 140

Gln Ser Ala Leu Thr Gln Pro Pro Ser Val Ser Gly Ser Pro Gly Gln
145                 150                 155                 160

Ser Val Thr Ile Ser Cys Thr Gly Ser Ser Asp Val Gly Tyr Tyr
            165                 170                 175

Asp His Val Ser Trp Tyr Gln His Pro Gly Arg Ala Pro Lys Val
        180                 185                 190

Ile Ile Tyr Asp Val Thr Lys Arg Pro Ser Gly Val Pro Asp Arg Phe
            195                 200                 205

Ser Gly Ser Lys Ser Gly Asn Thr Ala Ser Leu Thr Ile Ser Gly Leu
    210                 215                 220

Gln Ala Glu Asp Glu Ala Asp Tyr Tyr Cys Ser Ser Tyr Ala Gly Ser
```

```
                225                 230                 235                 240

Tyr Thr Trp Val Phe Gly Gly Thr Glu Leu Thr Val Leu Gly Gln
                245                 250                 255

Pro Lys Ala Ala Pro Ser Val Thr Leu Phe Pro Pro Ser Ser
                260                 265                 270

<210> SEQ ID NO 116
<211> LENGTH: 179
<212> TYPE: PRT
<213> ORGANISM: Artificial Sequence
<220> FEATURE:
<223> OTHER INFORMATION: Synthetic

<400> SEQUENCE: 116

Arg Glu Leu Ile Asp Gln Tyr Asp Val Gln Arg Asp Asp Ser Ser Asp
  1               5                  10                  15

Gly Ser Leu Glu Asp Asp Asp Tyr His Ala Thr Thr Glu Thr Ile Ile
                 20                  25                  30

Thr Met Pro Thr Glu Ser Asp Phe Leu Met Gln Val Asp Gly Lys Pro
             35                  40                  45

Lys Cys Cys Phe Phe Lys Phe Ser Ser Lys Ile Gln Tyr Asn Lys Val
         50                  55                  60

Val Lys Ala Gln Leu Trp Ile Tyr Leu Arg Pro Val Glu Thr Pro Thr
 65                  70                  75                  80

Thr Val Phe Val Gln Ile Leu Arg Leu Ile Lys Pro Met Lys Asp Gly
                 85                  90                  95

Thr Arg Tyr Thr Gly Ile Arg Ser Leu Lys Leu Asp Met Asn Pro Gly
            100                 105                 110

Thr Gly Ile Trp Gln Ser Ile Asp Val Lys Thr Val Leu Gln Asn Trp
        115                 120                 125

Leu Lys Gln Pro Glu Ser Asn Leu Gly Ile Glu Ile Lys Ala Leu Asp
130                 135                 140

Glu Asn Gly His Asp Leu Ala Val Thr Phe Pro Gly Pro Gly Glu Asp
145                 150                 155                 160

Gly Leu Asn Pro Phe Leu Glu Val Lys Val Thr Asp Thr Pro Lys Arg
                165                 170                 175

Ser Arg Arg
```